(12) United States Patent
Kim

(10) Patent No.: US 10,383,926 B2
(45) Date of Patent: Aug. 20, 2019

(54) BIOLOGICAL MARKERS USEFUL IN CANCER IMMUNOTHERAPY

(71) Applicants: GEMVAX & KAEL CO., LTD., Daejeon (KR); Sang Jae Kim, Seoul (KR)

(72) Inventor: Sang Jae Kim, Seoul (KR)

(73) Assignee: GemVax & KAEL Co., Ltd., Daejeon (KR)

( * ) Notice: Subject to any disclaimer, the term of this patent is extended or adjusted under 35 U.S.C. 154(b) by 0 days.

(21) Appl. No.: 14/896,358

(22) PCT Filed: Jun. 5, 2014

(86) PCT No.: PCT/KR2014/005031
§ 371 (c)(1),
(2) Date: Dec. 4, 2015

(87) PCT Pub. No.: WO2014/196841
PCT Pub. Date: Dec. 11, 2014

(65) Prior Publication Data
US 2016/0120966 A1 May 5, 2016

(30) Foreign Application Priority Data

Jun. 7, 2013 (EP) ..................................... 13171068
Feb. 4, 2014 (EP) ..................................... 14153819

(51) Int. Cl.
| | |
|---|---|
| A61K 38/08 | (2019.01) |
| A61K 38/10 | (2006.01) |
| A61K 39/00 | (2006.01) |
| A61K 31/7068 | (2006.01) |
| G01N 33/574 | (2006.01) |
| G01N 33/68 | (2006.01) |

(52) U.S. Cl.
CPC ...... *A61K 39/0011* (2013.01); *A61K 31/7068* (2013.01); *A61K 38/08* (2013.01); *A61K 38/10* (2013.01); *G01N 33/57438* (2013.01); *G01N 33/57488* (2013.01); *G01N 33/6893* (2013.01); *G01N 2333/4737* (2013.01); *G01N 2333/521* (2013.01); *G01N 2333/523* (2013.01); *G01N 2800/24* (2013.01); *G01N 2800/52* (2013.01); *G01N 2800/7095* (2013.01)

(58) Field of Classification Search
None
See application file for complete search history.

(56) References Cited

U.S. PATENT DOCUMENTS

| | | |
|---|---|---|
| 6,967,211 B2 | 11/2005 | Inoue |
| 7,030,211 B1 | 4/2006 | Gaudernack et al. |
| 7,786,084 B2 | 8/2010 | Benner et al. |
| 7,794,723 B2 | 9/2010 | Gaudernack et al. |
| 8,828,403 B2 | 9/2014 | Filaci et al. |
| 8,933,197 B2 | 1/2015 | Bogin et al. |
| 9,023,987 B2 | 5/2015 | Chung et al. |
| 9,540,419 B2 | 1/2017 | Kim et al. |
| 9,572,858 B2 | 2/2017 | Kim et al. |
| 2002/0042401 A1 | 4/2002 | Ferguson et al. |
| 2003/0027769 A1 | 2/2003 | Scialdone et al. |
| 2003/0143228 A1 | 7/2003 | Chen et al. |
| 2006/0106196 A1 | 5/2006 | Gaudernack et al. |
| 2007/0190561 A1 | 8/2007 | Morin et al. |
| 2008/0025986 A1 | 1/2008 | Ozes et al. |
| 2009/0136917 A1 | 5/2009 | Szalay et al. |
| 2009/0186802 A1 | 7/2009 | Alluis et al. |
| 2009/0215852 A1 | 8/2009 | Bascomb et al. |
| 2011/0135692 A1 | 6/2011 | Filaci et al. |
| 2011/0150873 A1 | 6/2011 | Grainger |
| 2011/0183925 A1 | 7/2011 | Sato et al. |
| 2012/0053134 A1 | 3/2012 | Jung et al. |
| 2012/0065124 A1 | 3/2012 | Morishita et al. |
| 2012/0208755 A1 | 8/2012 | Leung |
| 2012/0277290 A1 | 11/2012 | Collard et al. |
| 2013/0129760 A1 | 5/2013 | Gaudernack et al. |
| 2013/0230591 A1 | 9/2013 | Fellous et al. |
| 2015/0099692 A1 | 4/2015 | Kim et al. |
| 2015/0099693 A1 | 4/2015 | Kim et al. |
| 2015/0175978 A1 | 6/2015 | Kim |
| 2015/0307859 A1 | 10/2015 | Kim |
| 2015/0343095 A1 | 12/2015 | Kim |
| 2015/0353903 A1 | 12/2015 | Kim |
| 2016/0002613 A1 | 1/2016 | Kim |
| 2016/0008438 A1 | 1/2016 | Kim |
| 2016/0082089 A1 | 3/2016 | Kim |
| 2016/0137695 A1 | 5/2016 | Kim |
| 2016/0151512 A1 | 6/2016 | Kim |
| 2016/0250279 A1 | 9/2016 | Kim et al. |
| 2016/0296604 A1 | 10/2016 | Kim |
| 2016/0375091 A1 | 12/2016 | Kim |
| 2017/0028035 A1 | 2/2017 | Kim |
| 2017/0058001 A1 | 3/2017 | Kim |
| 2017/0081376 A1 | 3/2017 | Kim et al. |
| 2017/0128557 A1 | 5/2017 | Kim et al. |
| 2017/0143806 A1 | 5/2017 | Kim et al. |
| 2017/0275603 A1 | 9/2017 | Kim et al. |
| 2017/0360870 A1 | 9/2017 | Kim et al. |

FOREIGN PATENT DOCUMENTS

| | | |
|---|---|---|
| EP | 1020190 A3 | 10/2000 |
| EP | 1093381 B2 | 7/2009 |

(Continued)

OTHER PUBLICATIONS

Middleton et al., Lancet Oncology, 15(8):829-40, Jul. 2014.*

(Continued)

*Primary Examiner* — Marianne P Allen
(74) *Attorney, Agent, or Firm* — Sterne, Kessler, Goldstein & Fox P.L.L.C.

(57) ABSTRACT

Methods are disclosed that are based on the finding that serum and plasma levels of eotaxin, MIP1α, and CRP act as important biomarkers that are useful for determining the feasibility in instigating immunotherapeutic treatment of cancer when immunizing with the GV1001 peptide (EARPALLTSRLRFIPK; derived from human telomerase protein), optionally when combined with state of the art combination treatment with Gemcitabine and Capecitabine. In particular, the present invention provides methods for determining whether patients should be treated GV1001 and for determining whether instigated treatment should be continued.

7 Claims, 47 Drawing Sheets

Specification includes a Sequence Listing.

(56) References Cited

FOREIGN PATENT DOCUMENTS

| | | |
|---|---|---|
| EP | 1817337 B1 | 1/2011 |
| EP | 3372613 A1 | 9/2018 |
| JP | 2002522373 A | 7/2002 |
| JP | 2010252810 A | 11/2010 |
| JP | 2012526524 A | 11/2012 |
| JP | 5577472 B2 | 8/2014 |
| KR | 19930001915 A | 2/1993 |
| KR | 20010012613 A | 2/2001 |
| KR | 20010020601 A | 3/2001 |
| KR | 20040015087 A | 2/2004 |
| KR | 20040045400 A | 6/2004 |
| KR | 20040107492 A | 12/2004 |
| KR | 20050020987 A | 3/2005 |
| KR | 20050040517 A | 5/2005 |
| KR | 20060109903 A | 10/2006 |
| KR | 20070083218 A | 8/2007 |
| KR | 20080084818 A | 9/2008 |
| KR | 20090033878 A | 4/2009 |
| KR | 20090103957 A | 10/2009 |
| KR | 20100058541 A | 6/2010 |
| KR | 2010008552 A | 7/2010 |
| KR | 20110057049 A | 5/2011 |
| KR | 20110060940 A | 6/2011 |
| KR | 20110062943 A | 6/2011 |
| KR | 20110130943 A | 12/2011 |
| KR | 20120018188 A | 2/2012 |
| KR | 20120026408 A | 3/2012 |
| KR | 20120035150 A | 4/2012 |
| KR | 20120087885 A | 8/2012 |
| KR | 20120121196 A | 11/2012 |
| KR | 20120130996 A | 12/2012 |
| KR | 20120133661 A | 12/2012 |
| KR | 20130004949 A | 1/2013 |
| KR | 20130041896 A | 4/2013 |
| KR | 20140037698 A | 3/2014 |
| KR | 20060065588 A | 6/2016 |
| WO | WO-0002581 A1 | 1/2000 |
| WO | WO-2010003520 A2 | 1/2010 |
| WO | WO-2010012850 A1 | 2/2010 |
| WO | WO-2010128807 A2 | 11/2010 |
| WO | WO-2011101173 A1 | 8/2011 |
| WO | WO-2011150494 A1 | 12/2011 |
| WO | WO-2013100500 A1 | 7/2013 |
| WO | WO-2013118899 A1 | 8/2013 |
| WO | WO-2013135266 A1 | 9/2013 |
| WO | WO-2013167574 A1 | 11/2013 |
| WO | WO-2013169060 A1 | 11/2013 |
| WO | WO-2013169067 A1 | 11/2013 |
| WO | WO-2013169077 A1 | 11/2013 |
| WO | WO-2014010971 A1 | 1/2014 |
| WO | WO-2014012683 A1 | 1/2014 |
| WO | WO-2014046478 A1 | 3/2014 |
| WO | WO-2014046481 A1 | 3/2014 |
| WO | WO 2014046490 A1 | 3/2014 |
| WO | WO-2014171792 A1 | 10/2014 |
| WO | WO-2014204281 A1 | 12/2014 |
| WO | WO-2015060673 A1 | 4/2015 |
| WO | WO-2015076621 A1 | 5/2015 |
| WO | WO-2015093854 A1 | 6/2015 |
| WO | WO-2015156649 A1 | 10/2015 |
| WO | WO-2015167067 A1 | 11/2015 |
| WO | WO-2016105086 A1 | 6/2016 |
| WO | WO-2016137162 A1 | 9/2016 |
| WO | WO-2017078440 A1 | 5/2017 |

OTHER PUBLICATIONS

ClinicalTrials.gov/archive/NCT00425360/2007_01_22 (accessed Jan. 12, 2017).*

Shay, J.W., and Wright, W.E., "Telomerase Therapeutics for Cancer: Challenges and New Directions," Nature Reviews. Drug Discovery 5(7):577-584, Nature Publishing Group, England (2006).

Altschul, S.F., et al., "Basic Local Alignment Search Tool," Journal of Molecular Biology 215(3):403-410, Elsevier, England (1990).

Bernhardt, S.L., et al., "Telomerase Peptide Vaccination of Patients with Non-Resectable Pancreatic Cancer: A Dose Escalating Phase I/II Study," British Journal of Cancer 95(11): 1474-1482, Nature Publishing Group on behalf of Cancer Research, England (2006).

Bonaldi, T., et al., "Monocytic Cells Hyperacetylate Chromatin Protein HMGB1 to Redirect it Towards Secretion," The EMBO Journal 22(20):5551-5560, Wiley Blackwell, England (2003).

Brandenburg, K., et al., "Peptide-based Treatment of Sepsis," Applied Microbiology and Biotechnology 90(3):799-808, Springer International, Germany (2011).

Brunsvig, P.F., et al., "Telomerase Peptide Vaccination in NSCLC: A Phase II Trial in Stage III Patients Vaccinated after Chemoradiotherapy and An 8-year Update on a Phase I/II Trial," Clinical Cancer Research 17(21):6847-6857, The Association, United States (2011).

Cho, Y.J., "GemVax & Kael (082270)," Hana Daetoo Securities, Company Report, Sep. 10, 2012, pp. 1-9.

Choi, S.G., "Recent Advances in Cancer Cachexia," Journal of Korean Oncology Nursing 11(1):20-25 (2011).

Co-pending U.S. Appl. No. 14/413,732, inventor Sang Jae Kim, filed Jul. 11, 2013 (Not Published).

Co-pending U.S. Appl. No. 14/896,358, inventor Sang Jae Kim, filed Dec. 4, 2015 (Not Published).

Co-pending U.S. Appl. No. 14/899,746, inventor Sang Jae Kim, filed Apr. 12, 2015 (Not Published).

Dahlgren, K.N., et al., "Oligomeric and Fibrillar Species of Amyloid-beta Peptides Differentially Affect Neuronal Viability," Journal of Biological Chemistry 277(35):32046-32053, American Society for Biochemistry and Molecular Biology, United States (2002).

Dinarello, C.A., "Interleukin-1 in the Pathogenesis and Treatment of Inflammatory Diseases," Blood 117(14):3720-3732, American Society of Hematology, United States (2011).

Engineer, D.R. and Garcia, J.M., "Leptin in Anorexia and Cachexia Syndrome," International Journal of Peptides 2012:Article ID 287457, pp. 1-13, Hindawi Publishing Corporation, United States (2012).

Fire, A., et al., "Potent and Specific Genetic Interference by Double-stranded RNA in Caenorhabditis Elegans," Nature 391(6669):806-811, Nature Publishing Group, England (1998).

Fittipaldi, A., et al., "Cell Membrane Lipid Rafts Mediate Caveolar Endocytosis of HIV-1 Tat Fusion Proteins," Journal of Biological Chemistry 278(36): 34141-34149, American Society for Biochemistry and Molecular Biology, United States (2003).

Fonseca, S.B., et al., "Recent Advances in the Use of Cell-Penetrating Peptides for Medical and Biological Applications," Advanced Drug Delivery Reviews 61(11):953-964, Elsevier Science Publishers, Netherlands (2009).

Fujii, H., et al., "Telomerase Insufficiency in Rheumatoid Arthritis," Proceedings of the National Academy of Sciences USA 106(11):4360-4365, National Academy of Sciences, United States (2009).

GemVax Receives Report on Anti-Inflammatory Mechanism, The Asia Economy Daily, 1 page, Article written on May 7, 2013.

Ghaneh, P., et al., "Biology and Management of Pancreatic Cancer," Gut 56(8):1134-1152, British Medical Association, England (2007).

Granger, D.N. and Korthuis, R.J., "Physiologic Mechanisms of Postischemic Tissue Injury," Annual Review of Physiology 57:311-332, Annual Reviews, United States (1995).

Gunturu, K.S., et al., "Immunotherapy Updates in Pancreatic Cancer: Are we there yet?," Therapeutic Advances in Medical Oncology 5(1): 81-89, Sage, England (2013).

Heitz, F., et al., "Twenty Years of Cell-Penetrating Peptides: From Molecular Mechanisms to Therapeutics," British Journal of Pharmacology 157(2):195-206, Wiley, England (2009).

Hse, "Rheumatoid arthritis," http://www.hse.ie/portal/eng, accessed at http://www.hse.ie/portal/eng/health/az/R/Rheumatoid-arthritis/, 14 pages (2013).

Kern, K.A. and Norton, J.A., "Cancer Cachexia," Journal of Parenteral and Enteral Nutrition 12(3):286-298, Sage Publications, United States (1988).

Kim, H.O. and Lee, S.I., "Experimental Animal Models for Rheumatoid Arthritis: Methods and Applications," Journal of Rheumatic Diseases 19(4):189-195 (2012).

(56) References Cited

OTHER PUBLICATIONS

Kyte, J.A., "Cancer Vaccination with Telomerase Peptide GV1001," Expert Opinion on Investigational Drugs 18(5):687-694, Taylor & Francis, England (2009).

Lahdevirta, J., et al., "Elevated Levels of Circulating Cachectin/tumor Necrosis Factor in Patients with Acquired Immunodeficiency Syndrome," American Journal of Medicine 85(3):289-291, Excerpta Medica, United States (1988).

Laviano, A., et al., "Therapy Insight: Cancer Anorexia-cachexia Syndrome—When All You Can Eat is Yourself," Nature Clinical Practice. Oncology 2(3):158-165, Nature Publishing Group, England (2005).

Lee, S.A., et al., "Heat Shock Protein-Mediated Cell Penetration and Cytosolic Delivery of Macromolecules by a Telomerase-Derived Peptide Vaccine," Biomaterials 34(30):7495-7505, Elsevier Science, Netherlands (2013).

Luft, R., et al., "A Case of Severe Hypermetabolism of Nonthyroid Origin with a Defect in the Maintenance of Mitochondrial Respiratory Control: A Correlated Clinical, Biochemical, and Morphological Study," Journal of Clinical Investigation 41:1776-1804, American Society for Clinical Investigation, United States (1962).

Martinez, P. and Blasco, M.A., "Telomeric and Extra-telomeric Roles for Telomerase and the Telomere-binding Proteins," Nature Reviews Cancer 11(3):161-176, Nature Publishing Group, England (2011).

Modica-Napolitano, J.S. and Singh, K.K., "Mitochondria as Targets for Detection and Treatment of Cancer," Expert Reviews in Molecular Medicine 4(9):1-19, Cambridge University Press, England (2002).

Myers, L.K., et al., "Collagen-Induced Arthritis, an Animal Model of Autoimmunity," Life Sciences 61(19):1861-1878, Elsevier, Netherlands (1997).

National Horizon Scanning Centre of the National Institute for Health Research, University of Birmingham, "GV1001 for Advanced and/or Metastatic Pancreatic Cancer," News on Emerging Technologies in Healthcare, 5 pages, Published Apr. 2008.

Novina, C.D. And Sharp, P.A., "The RNAi Revolution," Nature 430(6996):161-164, Nature Publishing Group, England (2004).

Oh, H., et al., "Telomerase Reverse Transcriptase Promotes Cardiac Muscle Cell Proliferation, Hypertrophy, and Survival," Proceedings of the National Academy of Sciences 98(18): 10308-10313, National Academy of Sciences, United States (2001).

Pearson, W.R. and Lipman, D.J., "Improved Tools for Biological Sequence Comparison,"Proceedings of the National Academy of Sciences USA 85(8):2444-2448, National Academy of Sciences, United States (1988).

Rana, T.M., "Illuminating the Silence: Understanding the Structure and Function of Small RNAs," Nature Reviews. Molecular Cell Biology 8(1):23-36, Nature Publishing Group, England (2007).

Roubenoff, R., et al., "Adjuvant Arthritis as a Model of Inflammatory Cachexia," Arthritis and Rheumatism 40(3):534-539, Wiley-Blackwell, United States (1997).

Smith, D.B. and Johnson, K.S., "Single-step Purification of Polypeptides Expressed in *Escherichia coli* as Fusions with Glutathione S-transferase," Gene 67(1):31-40, Elsevier, Netherlands (1988).

Smith, T.F. and Waterman, M.S., "Comparison of Biosequences," Advances in Applied Mathematics 2(4):482-489, Academic Press, Inc., United States (1981).

Southern Cross, "Rheumatoid arthritis—causes, symptoms, and treatment," https://www.southerncross.co.nz/, accessed at https://www.southerncross.co.nz/AboutTheGroup/HealthResources/MedicalLibrary/tabid/178/vw/1/itemID/124/Rheumatoid-arthritis-causes-symptoms-treatment.aspx, last reviewed on May 31, 2013, 5 pages.

Stevenson, C.L., "Advances in Peptide Pharmaceuticals," Current Pharmaceutical Biotechnology 10(1):122-137, Bentham Science Publishers, Netherlands (2009).

Taylor, P.C. and Feldmann, M., "Anti-TNF Biologic Agents: Still the Therapy of Choice for Rheumatoid Arthritis," Nature Reviews. Rheumatology 5(10):578-582, Macmillan Publishers Limited, England (2009).

Thompson, J.D., et al., "Clustal W: Improving the Sensitivity of Progressive Multiple Sequence Alignment Through Sequence Weighting, Position-specific Gap Penalties and Weight Matrix Choice," Nucleic Acids Research 22(22):4673-4680, Oxford University Press, England (1994).

Tisdale, M.J., "Mechanisms of Cancer Cachexia," Physiological Reviews 89(2):381-410, American Physiological Society, United States (2009).

Tomari Y. and Zamore, P.D., "Perspective: Machines for RNAi," Genes and Development 19(5):517-529, Cold Spring Harbor Laboratory Press, United States (2005).

Walsmith, J. and Roubenoff, R., "Cachexia in Rheumatoid Arthritis," International Journal of Cardiology 85(1):89-99, Elsevier, Netherlands (2002).

Yankner, B.A., et al., "Neurotrophic and Neurotoxic Effects of Amyloid Beta Protein: Reversal by Tachykinin Neuropeptides," Science 250(4978):279-282, American Association for the Advancement of Science, United States (1990).

Inderberg-Suso, E.M., et al., "Widespread CD4+ T-cell Reactivity to Novel hTERT Epitopes following Vaccination of Cancer Patients with a Single hTERT Peptide GV1001," Oncoimmunology 1(5):670-686, Taylor & Francis, United States (2012).

Kokhaei, P., et al., "Telomerase (hTERT 611-626) Serves as a Tumor Antigen in B-cell Chronic Lymphocytic Leukemia and Generates Spontaneously Antileukemic, Cytotoxic T Cells," Experimental Hematology 35(2):297-304, Elsevier Science Inc., Netherlands (2007).

Schlapbach, C., et al., "Telomerase-specific GV1001 Peptide Vaccination Fails to Induce Objective Tumor Response in Patients with Cutaneous T Cell Lymphoma," Journal of Dermatological Science 62(2):75-83, Elsevier, Netherlands (2011).

Vennela, B., et al., "Current and Future Strategies for Therapy of Pancreatic Cancer," International Journal of Research in Pharmacy and Medicine 2(3):728-740 (2012).

Beer, T.M., et al., "Phase II Study of Weekly Docetaxel in Symptomatic Androgen-independent Prostate Cancer," Annals of Oncology 12(9):1273-1279, Oxford University Press, England (2001).

Bohonowych, J.E., et al., "Comparative Analysis of Novel and Conventional HSP90 inhibitors on HIF Activity and Angiogenic Potential in Clear Cell Renal Cell Carcinoma: Implications for Clinical Evaluation," BMC Cancer 11:520, BioMed Central, England (2011).

Bruns, A.F., et al., "A Heat-shock Protein Axis Regulates VEGFR2 Proteolysis, Blood Vessel Development and Repair," PloS One 7(11):e48539, Public Library of Science, United States (2012).

Calderwood, S.K., et al., "Heat Shock Proteins in Cancer: Chaperones of Tumorigenesis," Trends in Biochemical Sciences 31(3):164-172, Elsevier Trends Journals, England (2006).

Dempsey, N.C., et al., "Differential Heat Shock Protein Localization in Chronic Lymphocytic Leukemia," Journal of Leukocyte Biology 87(3):467-476, Society for Leukocyte Biology, United States (2010).

Du, R., et al., "HIF1alpha Induces the Recruitment of Bone Marrow-derived Vascular Modulatory Cells to Regulate Tumor Angiogenesis and Invasion," Cancer Cell 13(3):206-220, Cell Press, United States (2008).

Eustace, B.K. and Jay, D.G., "Extracellular Roles for the Molecular Chaperone, Hsp90," Cell Cycle 3(9):1098-1100, Taylor & Francis, United States (2004).

Eustace, B.K. and Jay, D.G., "Functional Proteomic Screens Reveal an Essential Extracellular Role for Hsp90 Alpha in Cancer Cell Invasiveness," Nature Cell Biology 6(6):507-514, Macmillan Magazines Ltd., England (2004).

Evans, C.G., et al., "Heat Shock Protein 70 (Hsp70) as an Emerging Drug Target," Journal of Medicinal Chemistry 53(12):4585-4602, American Chemical Society, United States (2010).

Ferrarini, M., et al., "Unusual Expression and Localization of Heat-shock Proteins in Human Tumor Cells," International Journal of Cancer 51(4):613-619, Wiley-Liss, United States (1992).

Garcia-Carbonero, R., et al., "Inhibition of HSP90 Molecular Chaperones: Moving Into the Clinic," The Lancet Oncology 14(9):e358-e369, Lancet Publishing Group, England (2013).

(56) References Cited

OTHER PUBLICATIONS

Henry, J.Y., et al., "Lenalidomide Enhances the Anti-prostate Cancer Activity of Docetaxel in vitro and in vivo," The Prostate 72(8):856-867, Wiley-Liss, United States (2012).
Jaattela, M., "Over-expression of Hsp70 Confers Tumorigenicity to Mouse Fibrosarcoma Cells," International Journal of Cancer 60(5):689-693, Wiley-Liss, United States (1995).
Jemal, A., el al., "Cancer Statistics, 2008," CA: A Cancer Journal for Clinicians 58(2):71-96, Wiley, United States (2008).
Kim, B.K., et al., "Tumor-suppressive Effect of a Telomerase-derived Peptide by Inhibiting Hypoxia-induced HIF-1α-VEGF Signaling Axis," Biomaterials 35(9):2924-2933, Elsevier Science, Netherlands (2014).
Kocsis, J., et al., "Serum Level of Soluble 70-kD Heat Shock Protein Is Associated With High Mortality in Patients With Colorectal Cancer Without Distant Metastasis," Cell Stress & Chaperones 15(2):143-151, Springer, Netherlands (2010).
Liu, Q.J., et al., "Rapamycin Enhances the Susceptibility of Both Androgen-dependent and -independent Prostate Carcinoma Cells to Docetaxel," Chinese Medical Journal 123(3):356-360, Chinese Medical Association, China (2010).
Mattson, M.P., "Pathways Towards and Away From Alzheimer's Disease," Nature 430(7000):631-639, Nature Publishing Group, England (2004).
McConnell, J.D., et al., "The Effect of Finasteride on the Risk of Acute Urinary Retention and the Need for Surgical Treatment Among Men with Benign Prostatic Hyperplasia. Finasteride Long-term Efficacy and Safety Study Group," The New England Journal of Medicine 338(9):557-563, Massachusetts Medical Society, United States (1998).
Morano, K.A., "New Tricks for an Old Dog: the Evolving World of Hsp70," Annals of the New York Academy of Sciences 1113:1-14, Blackwell, United States (2007).
Murphy, M.E., "The Hsp70 Family and Cancer," Carcinogenesis 34(6):1181-1188, Irl Press, England (2013).
Nagaraju, G.P., et al., "Antiangiogenic Effects of Ganetespib in Colorectal Cancer Mediated Through Inhibition of HIF-1α and STAT-3," Angiogenesis 16(4):903-917, Springer, Germany (2013).
Perez, R.G., et al., "The Beta-amyloid Precursor Protein of Alzheimer's Disease Enhances Neuron Viability and Modulates Neuronal Polarity," The Journal of Neuroscience 17(24):9407-9414, Society for Neuroscience, United States (1997).
Pfosser, A., et al., "Liposomal HSP90 Cdna Induces Neovascularization via Nitric Oxide in Chronic Ischemia," Cardiovascular Research 65(3):728-736, Oxford Journals, England (2005).
Powers, M.V., et al., "Targeted HSP70: the Second Potentially Druggable Heat Shock Protein and Molecular Chaperone?," Cell Cycle 9(8): 1542-1550, Taylor & Francis, United States (2010).
Sayers, S., et al., "Vaxjo: A Web-based Vaccine Adjuvant Database and its Application for Analysis of Vaccine Adjuvants and their Uses in Vaccine Development," Journal of Biomedicine and Biotechnology 2012:1-13, Article ID 831486, Hindawi Publishing Corporation, United States (2012).
Schenk, D., et al,, "Immunization with Amyloid-beta Attenuates Alzheimer-disease-like Pathology in the PDAPP Mouse," Nature 400(6740)173-177, Nature Publishing Group, England (1999).
Seo, J.S., et al., "T Cell Lymphoma in Transgenic Mice Expressing the Human Hsp70 Gene," Biochemical and Biophysical Research Communications 218(2):582-587, Elsevier, United States (1996).
Sun, J., et al., "Induction of Angiogenesis by Heat Shock Protein 90 Mediated by Protein Kinase Akt and Endothelial Nitric Oxide Synthase," Arteriosclerosis, Thrombosis, and Vascular biology 24(12):2238-2244, Lippincott Williams & Wilkins, United States (2004).
Uehara, Y., "Natural Product Origins of Hsp90 Inhibitors," Current Cancer Drug Targets 3(5):325-330, Bentham Science Publishers, Netherlands (2003).
Van Coppenolle, F., et al., "Effects of Hyperprolactinemia on Rat Prostate Growth: Evidence of Androgeno-dependence," American Journal of Physiology. Endocrinology and Metabolism 280(1):E120-E129, American Physiological Society, United States (2001).
Vanbuskirk, A., et al., "A Peptide Binding Protein Having a Role in Antigen Presentation Is a Member of the HSP70 Heat Shock Family," The Journal of Experimental Medicine 170(6):1799-1809, Rockefeller University Press, United States (1989).
Volloch, V.Z. and Sherman, M.Y., "Oncogenic Potential of Hsp72," Oncogene 18(24):2648-3651, Nature Publishing Group, England (1999).
Yeh, C.H., et al., "Clinical Correlation of Circulating Heat Shock Protein 70 in Acute Leukemia," Leukemia Research 34(5):605-609, Pergamon Press, England (2010).
Zhou, J., et al., "PI3K/Akt Is Required for Heat Shock Proteins to Protect Hypoxia-inducible Factor 1alpha From pVHL-independent Degradation," The Journal of Biological Chemistry 279(14):13596-13513, American Society for Biochemistry and Molecular Biology, United States (2004).
Kyte, J.A., et al., "Telomerase Peptide Vaccination Combined with Temozolornide: A Clinical Trial in Stage IV Melanoma Patients," Clinical Cancer Research 17(13):4568-4580, The Association, United States (2011).
Eisenegger, C., et al., "The Role of Testosterone in Social Interaction," Trends in Cognitive Sciences 15(6):263-271, Elsevier Science, England (2011).
Gong, W., et al., "Invasion Potential of H22 Hepatocarcinoma Cells is Increased by HMGB1-induced Tumor NF-κB Signaling via inititatin of HSP70," Oncology Reports 30(3):1249-1256, D.A. Spandidos, Greece (2013).
Guo, R.F., et al., "Regulatory Effects of Eotaxin on Acute Lung Inflammatory Injury," Journal of Immunology 166(8):5208-5218, American Association of Immunologists, United States (2001).
Heldin, C.H., et al., "TGF-Beta Signalling from Cell Membrane to Nucleus through SMAD Proteins," Nature 390(6659):465-471, Nature Publishing Group, England (1997).
Kawasaki, H., et al., "Detection and Evaluation of Activation of Various Cancer Antigenic Peptide-specific CTLs in Mature Dendritic Cells Used for Dendritic Cell Therapy," The21st International Congress of Personalized Medicine, Conference Program and Abstracts, Personalized Medicine Universe (Japanese edition) 4(Supplement 2): 2 pages, Oct. 17, 2015.
Massague, J., "Tgf-Beta Signal Transduction," Annual Review of Biochemistry 67:753-791, Annual Reviews, United States (1998).
Morishita, M., and Peppas, N.A., "Is the Oral Route Possible for Peptide and Protein Drug Delivery?," Drug Discovery Today 11(19-20):905-910, Elsevier Science Ltd., England (2006).
Sasada, A., et al., "A Case of Elderly Patient With Lung Cancer Efficiently Treated With Dendritic Cell Immunotherapy" The 20th International Congress of Personalized Medicine, Conference Program and Abstracts, Personalized Medicine Universe (Japanese edition) 4(Supplernent 1): 2 pages, May 24, 2015.
Shaw, V.E., et al., "Current Status of GV1001 and Other Telomerase Vaccination Strategies in the Treatment of Cancer," Expert Review of Vaccines 9(9):1007-1016, Taylor & Francis, England (2010).
Song, J., et al., "Characterization and Fate of Telomerase-Expressing Epithelia during Kidney Repair," Journal of the American Society of Nephrology 22(12)2256-2265, American Society of Nephrology, United States (2011).
Wang, W., et al., "Alleviating the Ischemia-Reperfusion Injury of Donor Liver by Transfection of Exogenous hTERT Genes," Transplantation Proceedings 41(5):1499-1503, Elsevier Science, United States (2009).
Yi, A., et al., "Radiation-induced Complications after Breast Cancer Radiation Therapy: a Pictorial Review of Multimodality Imaging Findings," Korean Journal of Radiology 10(5):496-507, Korean Society of Radiology, Korea (2009).
Zhang, H., et al., "Inhibiting TGFβ1 has a Protective Effect on Mouse Bone Marrow Suppression Following Ionizing Radiation Exposure in Vitro," Journal of Radiation Research 54(4):630-636, Oxford University Press, England (2013).

(56) References Cited

OTHER PUBLICATIONS

Berendsen, H.J., "A Glimpse of the Holy Grail?," Science 282(5389):642-643, American Association for the Advancement of Science, United States (1998).
ClinicalTrials.gov, "Adjuvant Leuprolide with or without Docetaxel in High Risk Prostate Cancer After Radical Prostatectomy," Identifier NCT00283062, first received on Jan. 26, 2006, accessed at https://clinaltrials.gov/ct2/show/study/NCT00283062, last accessed on May 12, 2017, 7 pages.
Co-pending U.S. Appl. No. 15/553,689, inventor Kim, S.J., et al., I.A. filed Feb. 18, 2016 (Not Published).
De Araujo, J.G., et al., "The Potential Use of Melatonin for Preventing Cisplatin Ototoxicity: An Insight for a Clinical Approach," Advances in Otolaryngology 2014:8 pages, Hindawi Publishing Corporation (2014).
Delves, P.J., "Allergic Rhinitis," Merck manual, accessed at http://www.merckmanuals.com/professional/immunology-allergic-disorders/allergic,-autoimmune,-and-other-hypersensitivity-disorders/allergic-rhinitis, accessed on Nov. 2, 2017, pp. 1-6.
Du, C., et al., "Conformational and Topological Requirements of Cell-permeable Peptide Function," The Journal of Peptide Research 51(3):235-243, Munksgaard, Denmark (1998).
Fried, M.P., "Nonallergic Rhinitis," Merck manual, accessed at http://www.msdmanuals.com/professional/ear,-nose,-and-throat-disorders/nose-and-paranasal-sinus-disorders/nonallergic-rhinitis, accessed on Nov. 2, 2017, pp. 1-3.
International Preliminary Report on Patentability and Written Opinion for International Application No. PCT/KR2015/014099, The International Bureau of WIPO, dated Jun. 27, 2017, 16 pages.
International Preliminary Report on Patentability and Written Opinion for International Application No. PCT/KR2016/001646, Korean Intellectual Property Office, Republic of Korea, dated May 20, 2016, 13 pages.
International Search Report for International Application No. PCT/KR2015/014099, Korean Intellectual Property Office, Republic of Korea, dated May 4, 2016, 8 pages.
International Search Report for International Application No. PCT/KR2016/001646, Korean Intellectual Property Office, Republic of Korea, dated May 20, 2016, 8 pages.
Kalnins, A., et al., "Sequence of the Lacz Gene of *Escherichia coli*," The EMBO Journal 2(4):593-597, Wiley Blackwell, England (1983).
Kim, B.H, "Presbycusis: Review for its Environmental Risk Factors," Korean Journal of Otorhinolaryngology—Head and Neck Surgery 49(10):962-967, Korean Society of Otolaryngology—Head and Neck Surgery, Korea (2006).
Lee, E.K., et al., "Inhibition of Experimental Choroidal Neovascularization by Telomerase-derived Peptide GV1001," Investigative Ophthalmology & Visual Science 56(7):Abstract 2291, ARVO Annual Meeting Abstract (Jun. 2015).
Mandal, A., "Types of Fibrosis," Retrieved from the internet on Jul. 3, 2014, pp. 1-3.
Merck, "Obesity, The Merck Manual Professsional Edition," accessed at http://www.merckmanuals.com/professional/nutritional-disorders/obesity-and-the-metabolic-syndrome/obesity, accessed on October 6, 2014, 9 pages.
National Center for Biotechnology Information, "Hormones," MeSH Database, Bethesda, accessed at http://www.ncbi.nlm.nih.gov/mesh/68006728, accessed on May 8, 2017, 3 pages.
National Institute of Diabetes and Digestive and Kidney Diseases, "Prostate Enlargement: Benign Prostatic Hyperplasia," accessed at https://www.niddk.nih.gov/health-information/urologic-diseases/prostate-problems/prostate-enlargernent-benign-prostatic-hyperplasia, accessed Sep. 2014, 14 pages.
Nawroth, I., et al., "Intraperitoneal Administration of Chitosan/DsiRNA Nanoparticles Targeting TNFα Prevents Radiation-induced Fibrosis," Radiotherapy and Oncology 97(1)143-148, Elsevier Scientific Publishers, Ireland (2010).

Ngo. et al., "Computational Complexity, Protein Structure Prediction, and the Levinthal Paradox," in The Protein Folding Problem and Tertiary Structure Prediction, Merz, Jr., K.M., and Le Grand, S.M., eds., pp. 491-494, Birkhauser Boston, United States (1994).
Ortega, V.E., "Asthma," Merck manual, accessed at http://www.merckmanuals.com/professional/pulmonary-disorders/asthma-and-related- disorders/asthma, accessed on Nov. 2, 2017, pp. 1-19.
Priya, S.G., et al., "Skin Tissue Engineering for Tissue Repair and Regeneration," Tissue Engineering, Part B, Reviews 14(1):105-118, Mary Ann Liebert, Inc., United States (2008).
Rosenbloom, J., et al., "Strategies for Anti-fibrotic Therapies," Biochimica et Biophysica Acta 1832(7):1088-1103, Elsevier Pub, Co., Netherlands (2013).
Rosenstein, B.J., "Cystic Fibrosis," Merck manual, accessed at http://www.msdmanuals.com/professional/pediatrics/cystic-fibrosis-cf/cystic-fibrosis, accessed on Nov. 2, 2017, pp. 1-15.
Rowe-Rendleman, C. and Glickman, R.D., "Possible therapy for age-related macular degeneration using human telomerase," Brain Research Bulletin 62(6):549-553, Elsevier Science Inc., United States (2004).
Rudinger, J., "Characteristics of the Amino Acids as Components of a Peptide Hormone Sequence," in Peptide Hormones, Parsons, J.A., ed., University Park Press, United States (1976).
Schwarze, S.R., et al., "In Vivo Protein Transduction: Delivery of a Biologically Active Protein Into the Mouse," Science 285(5433):1569-1572, American Association for the Advancement of Science, United States (1999).
SIGMA Genosys, "Designing Custom Peptides," accessed at http://www.sigma-genosys.com/peptide_design.asp, Accessed on Dec. 16, 2004, 2 pages.
Tisdale, M.J., "Catabolic Mediators of Cancer Cachexia," Current Opinion in Supportive and Palliative Care, 2(4):256-261, Lippincott Williams & Wilkins, United States (2008).
Voet, D. and Voet, J.G., "Abnormal Hemoglobins," in Biochemistry, 2nd Edition, Chapter 9, pp. 235-241, John Wiley & Sons, Inc., United States (1995).
Westin, E.R., et al., "The p53/p21(WAF/CIP) Pathway Mediates Oxidative Stress and Senescence in Dyskeratosis Congenita Cells With Telomerase Insufficiency," Antioxidants & Redox Signaling 14(6):985-997, Mary Ann Liebert, Inc., United States (2011).
Wynn, T.A. and Ramalingam, T.R., "Mechanisms of Fibrosis: Therapeutic Translation for Fibrotic Disease," Nature Medicine 18(7):1028-1040, Nature Publishing Company, United States (2012).
International Search Report for International Application No. PCT/KR2016/007192, Korean Intellectual Property Office, Republic of Korea, dated Sep. 12, 2016, 12 pages.
Written Opinion for International Application No. PCT/KR2016/007192, Korean Intellectual Property Office, Republic of Korea, dated Sep. 12, 2016, 16 pages.
Fauce, et al., Telomerase-based Pharmacologic Enhancement of Antiviral Function of Human CD8+ T Lymphocytes, The Journal of immunology 181(10):7400-7406, American Association of Immunologist, United States (2008).
Fontanes, V., et aL "A Cell permeable Peptide inhibits Hepatitis C Virus Replication by Sequestering IRES Transacting Factors," Virology 394:82-90, Elsevier, United States (2009).
Kim et al., "Inhibition of HIV-1 Reactivation by a Telomerase-derived Peptide in a HSP90-dependent Manner", Scientific Reports 6:1-10, Nature Publishing Group, United States (2016).
Lee, et al., "A Telomerase-derived Peptide Regulates Reactive oxygen Species and Hepatitis C Virus RNA Replication in HCV-infected Cells Via Heat Shock Protein 90," Biochemical and Biophysical Research Communications 471(1):156-162, Elsevier, Netherlands (2016).
Leem, G., et al., "Immunotherapy in Pancreatic Cancer; the Road Less Traveled," Immunological Disorders and Immunotherapy 1(2):1-6 (2016).
Supplementary European Search Report for EP Application No. EP 14808179.7, Munich, Germany, dated Jan. 10, 2017, 13 pages.
Extended European Search Report for EP Application No. EP 14808179.7, Munich, Germany, dated May 24, 2017, 24 pages.

(56) References Cited

OTHER PUBLICATIONS

Middleton, G., et al., "Gemcitabine and capecitabine with or without telomerase peptide vaccine GV1001 in patients with locally advanced or metastatic pancreatic cancer (TeloVac): an open-label, randomised, phase 3 trial," Lancet Oncol 15(8):829-840, Elsevier, Netherlands (2014).

Middleton, G., et al., "Poster: Predictive cytokine biomarkers for survival in patients with advanced pancreatic cancer randomized to sequential chemoimmunotherapy comprising gemcitabine and capecitabine (GemCap) followed by the telomerase vaccine GV1001 compared to concurrent chemoimmunotherapy in the TeloVac phase III tr," ASCO 2014. May 30, 2014 (May 30, 2014). —Jun. 3, 2014 (Jun. 3, 2014). pp. 1-1. XP055328448. Retrieved from the Internet: http://media4.asco.org/144/8599/93976/93976posterpvhr.jpg>.

Middleton, G., et al., "A phase III randomized trial of chemoimmunotherapy comprising gemcitabine and capecitabine with or without telomerase vaccine GV1001 in patients with locally advanced or metastatic pancreatic cancer." Presented at conference ASCO 2013. Jun. 4, 2013 (Jun. 4, 2013). p. 26 pp. .XP054977010. Retrieved from the internet:URL:http://meetinglibrary.asco.orgjcontent /82894?media=vm.

Middleton, G., et al., LBA4004: A phase III randomized trial of chemoimmunotherapy comprising gemcitabine and capecitabine with or without telomerase vaccine GV1001 in patients with locally advanced or metastatic pancreatic cancer. 2013 ASCO Annual Meeting. vol. 31. May 31, 2013 (May 31, 2013). —Jun. 4, 2013 (Jun. 4, 2013). pp. 1-3.XP055328310. p. 2.

Neoptolemos, J.P., et al., "Predictive cytokine biomarkers for survival in patients with advanced pancreatic cancer randomized to sequential chemoimmunotherapy comprising gemcitabine and capecitabine (GemCap) followed by the telomerase vaccine GV1001 compared to concurrent chemoimmunotherapy in the TeloVac phase III trial." 2014 ASCO Annual Meeting. May 30, 2014 (May 30, 2014). —Jun. 3, 2014 (Jun. 3, 2014). pp. 1-3.

Albini, A., et al., "Cancer Prevention by Targeting Angiogenesis," Nature reviews Clinical oncology 9(9):498-509, Nature Pub Group (2012).

Auerbach, R., et al., "Angiogenesis Assays: Problems and Pitfalls," Cancer Metastasis Reviews 19(1-2):167-172, Kluwer Academic, Netherlands (2000).

International Search Report and Written Opinion for International Application No. PCT/KR2016/012613, Korean Intellectual Property Office, Republic of Korea, dated Feb. 2, 2017, 14 pages .

Jain, R.K., "Barriers to Drug Delivery in Solid Tumors," Scientific American 271(1):58-65, Scientific American, Inc., United States (Jul. 1994).

Kirino, T, "Delayed Neuronal Death in the Gerbil Hippocampus Following Ischemia," Brain Research 239(1):57-69, Amsterdam Elsevier/North-Holland Biomedical Press, Netherlands (May 1982).

O'Beirne, J., et al., "Generation of Functional CD8+ T Cells by Human Dendritic Cells Expressing Glypican-3 Epitopes," in: Journal of Experimental and Clinical Cancer Research 29:48, BioMed Central, London (May 2010).

Olney, J.W., et al., "Pathological Changes Induced in Cerebrocortical Neurons by Phencyclidine and Related Drugs," Science 244(4910):1360-1362, American Association for the Advancement of Science, United States (Jun. 1989).

Varma, N., et al., "Role of hTERT and WT1 Gene Expression in Disease Progression and Imatinib Responsiveness of Patients with BCR-ABL Positive Chronic Myeloid Leukemia," in: Leukemia and Lymphoma 52(4):687-693, Informa Healthcare, London (Apr. 2011).

* cited by examiner

[Fig. 1a]
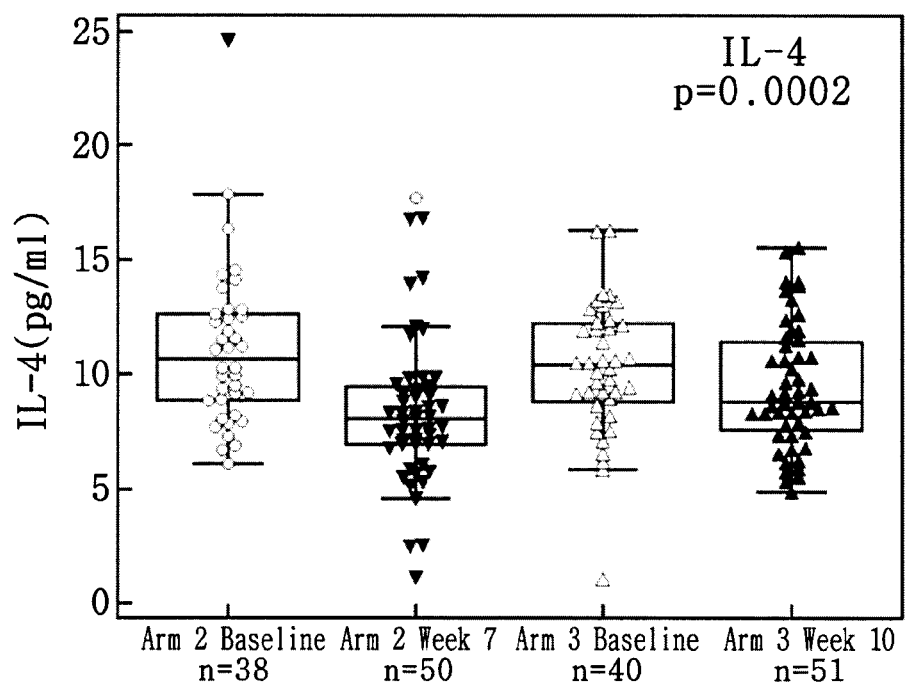
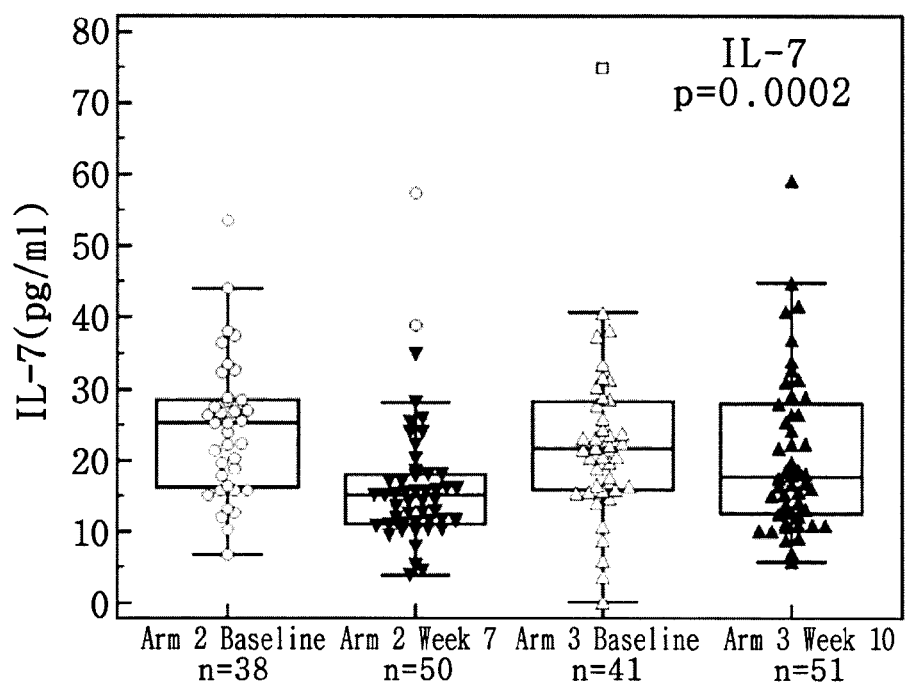

[Fig. 1b]
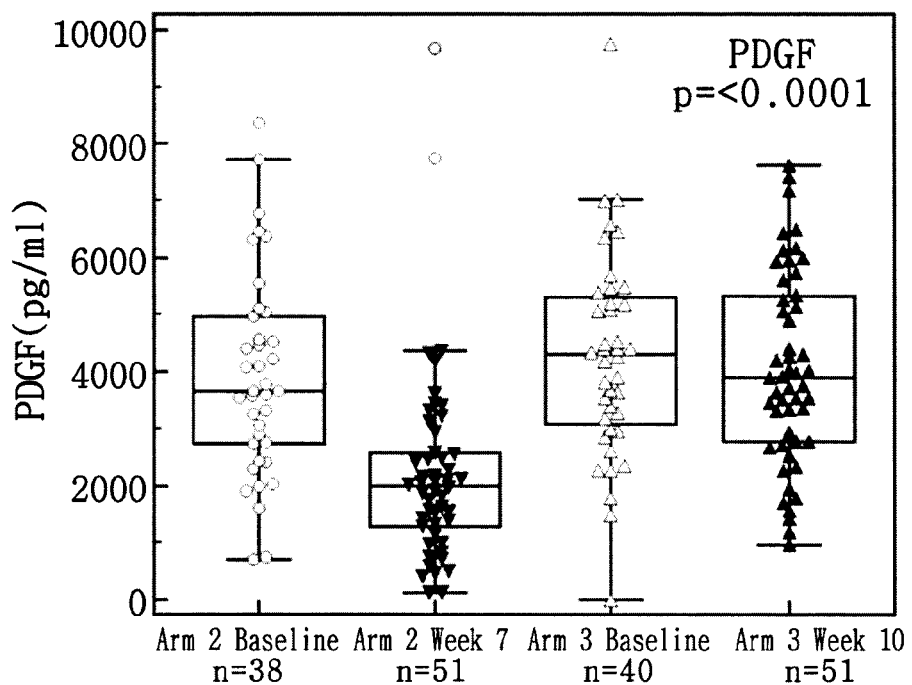
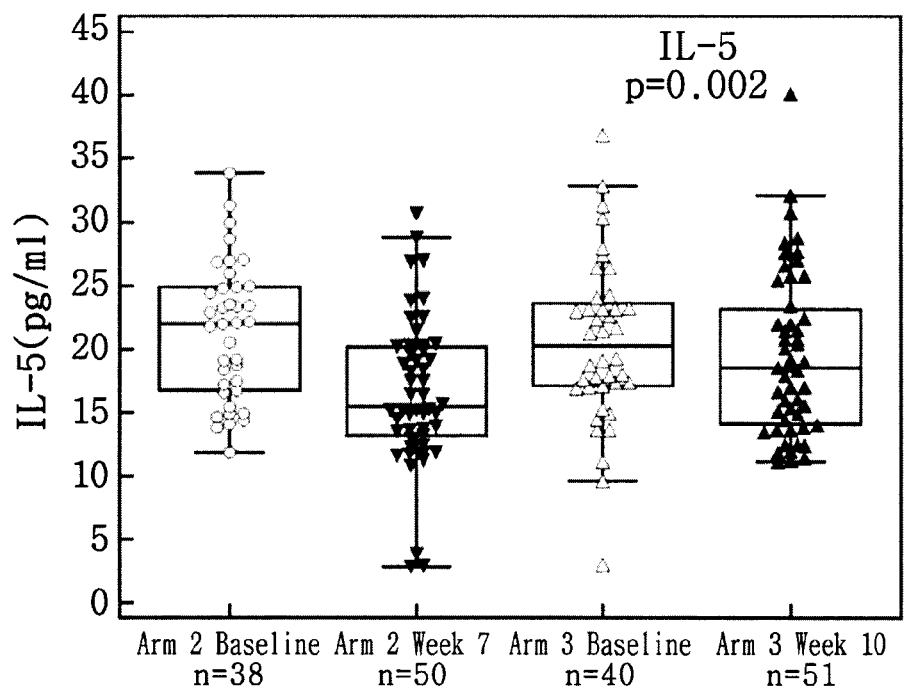

[Fig. 1c]
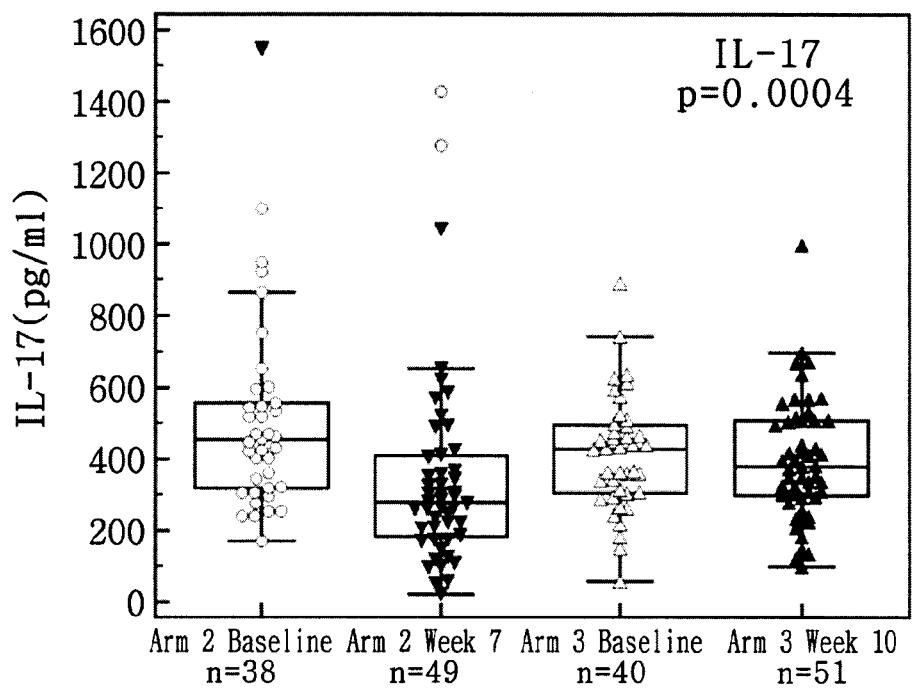
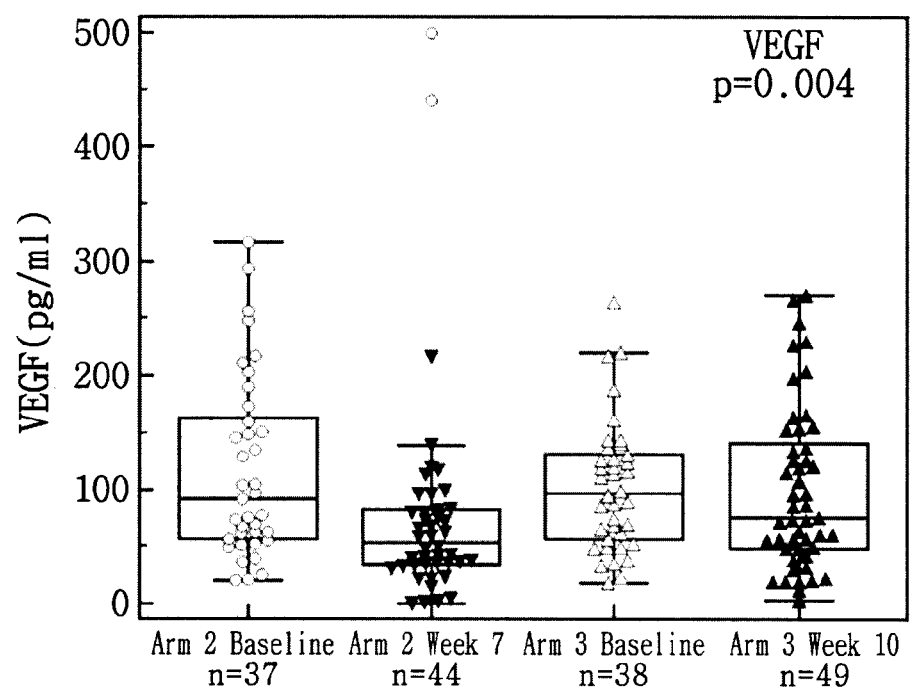

[Fig. 2a]
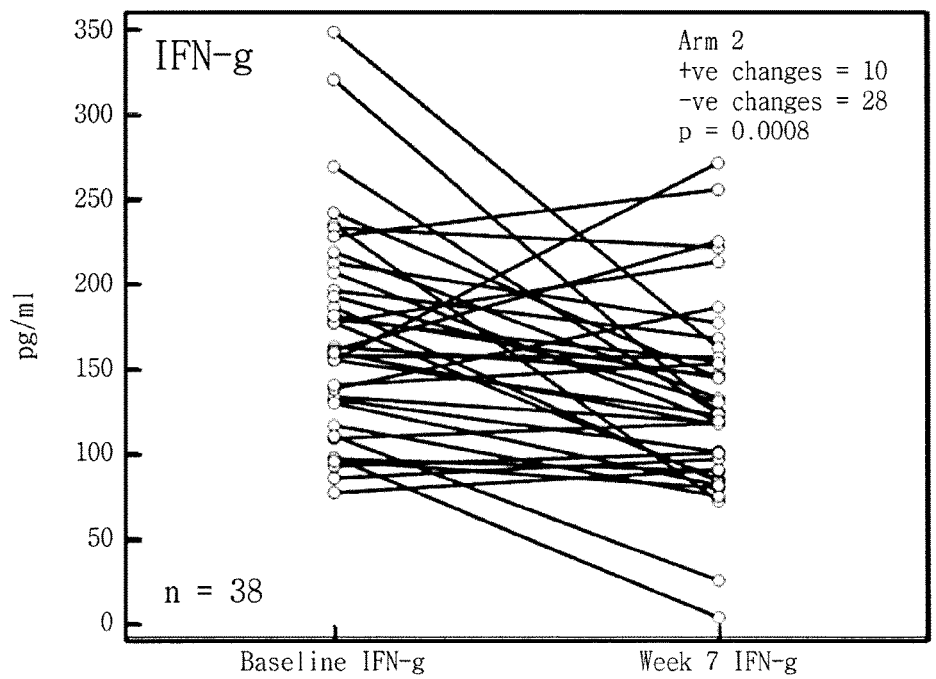
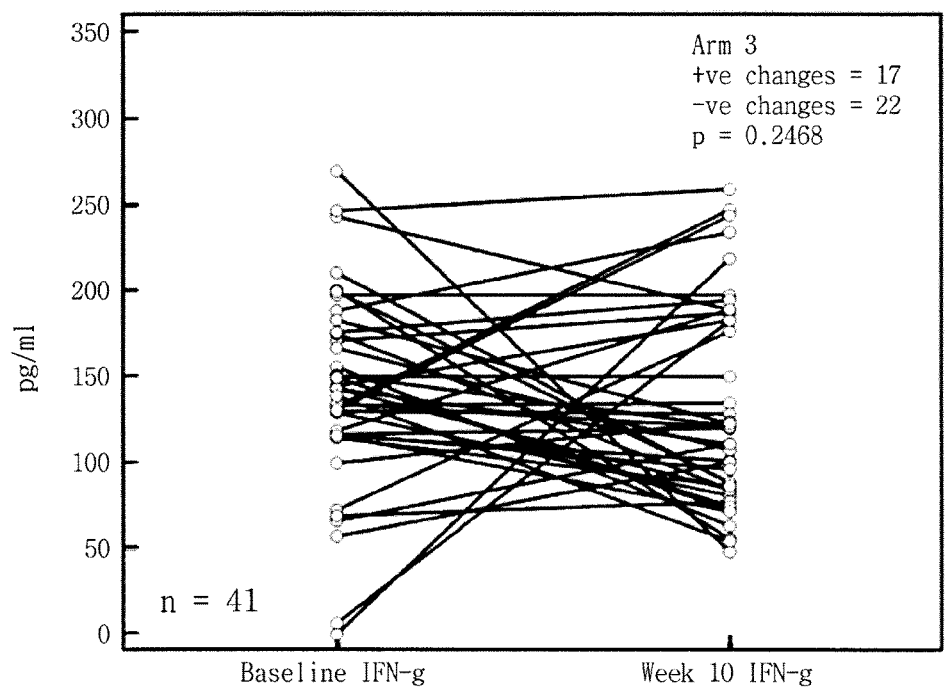

[Fig. 2b]
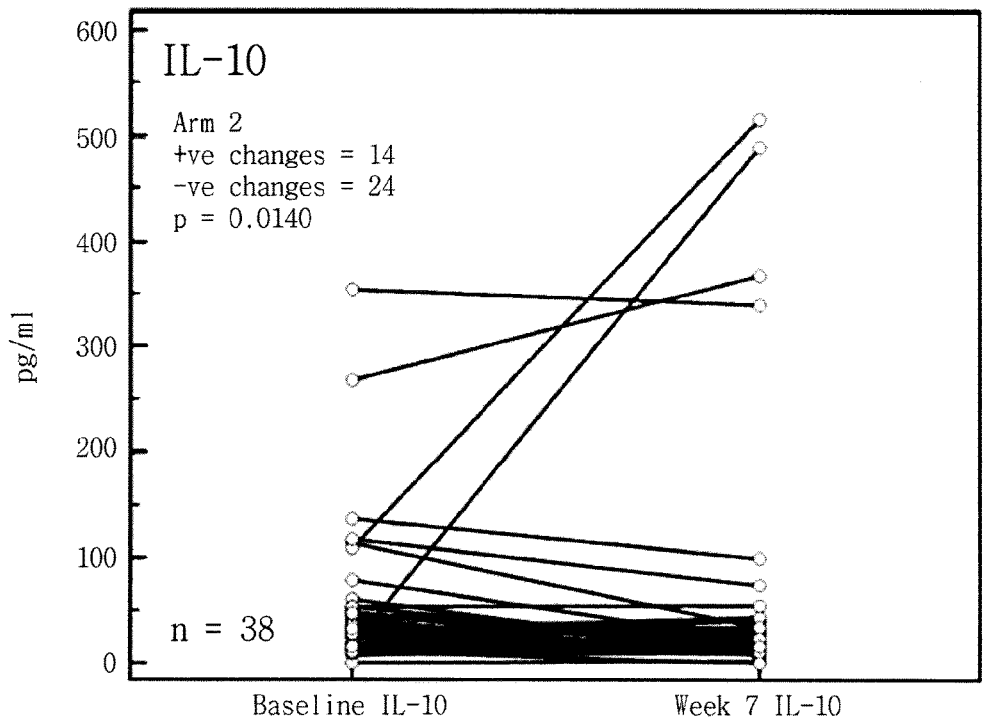
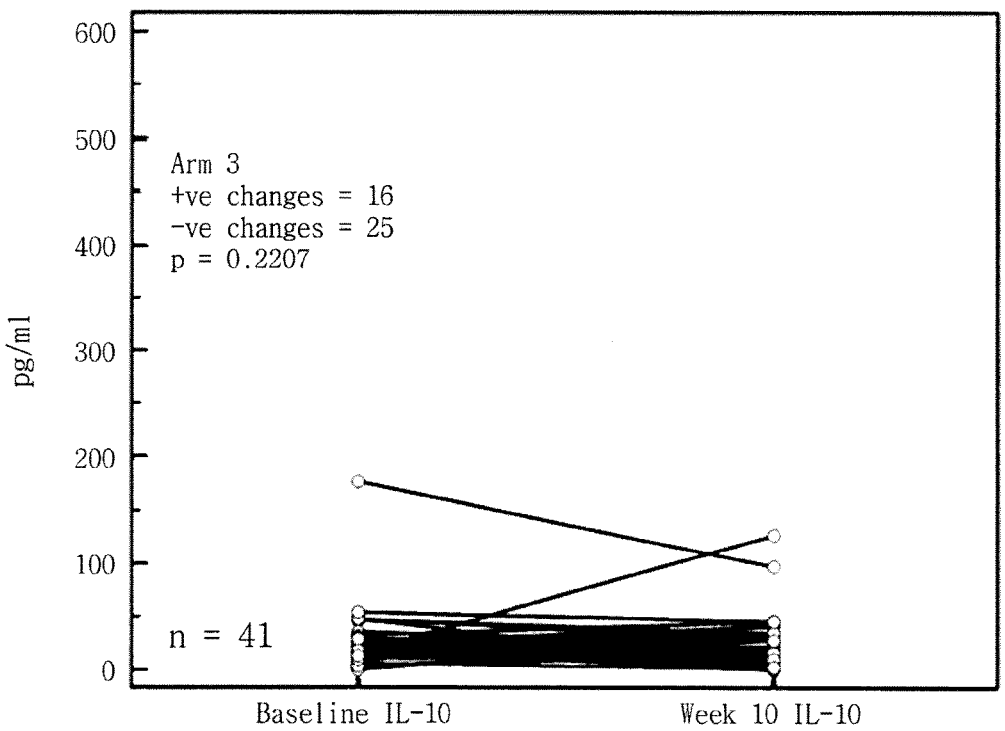

[Fig. 2c]
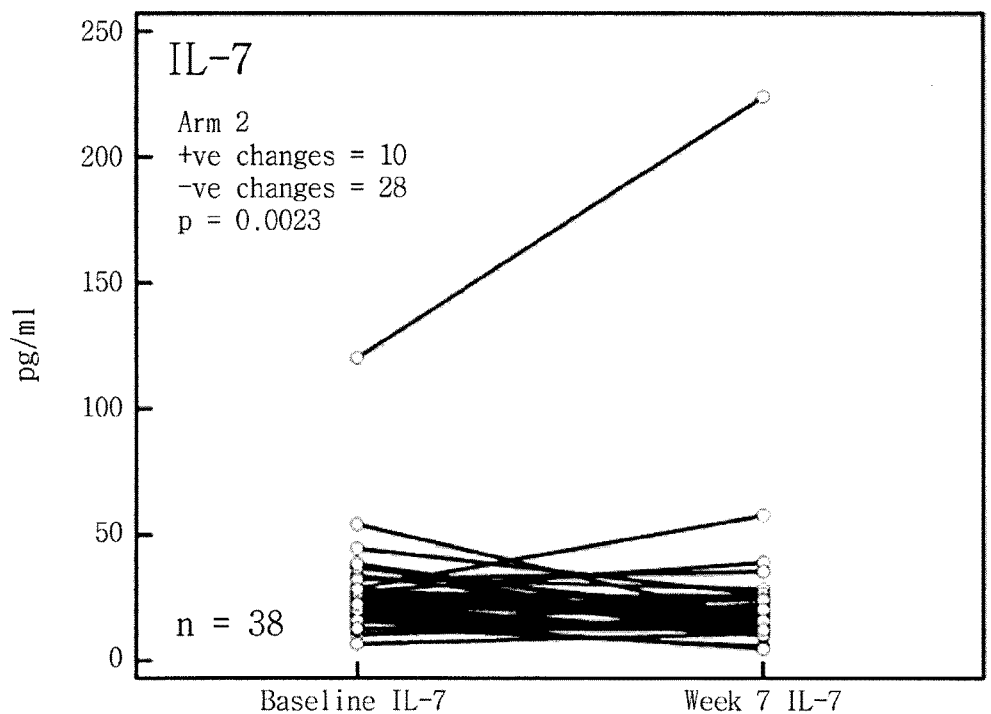
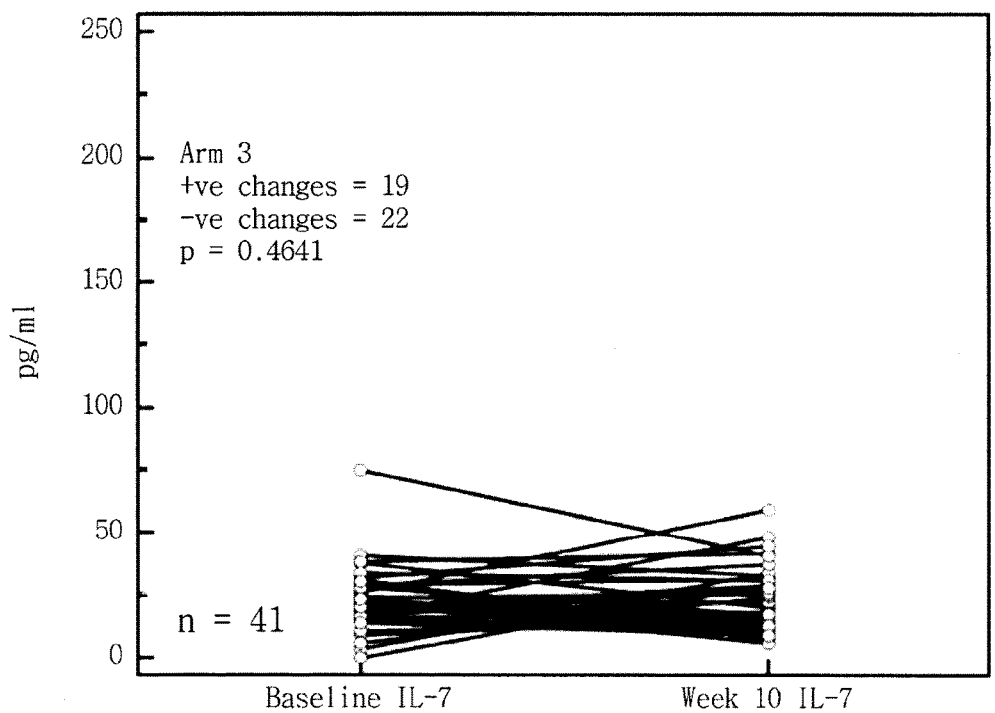

[Fig. 2d]
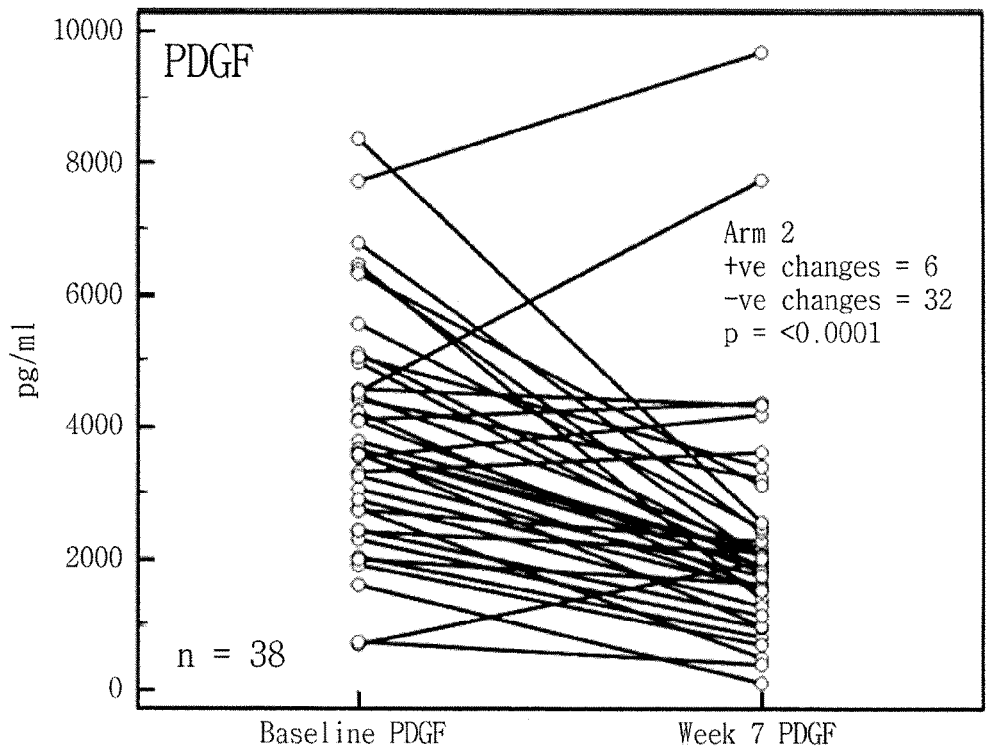
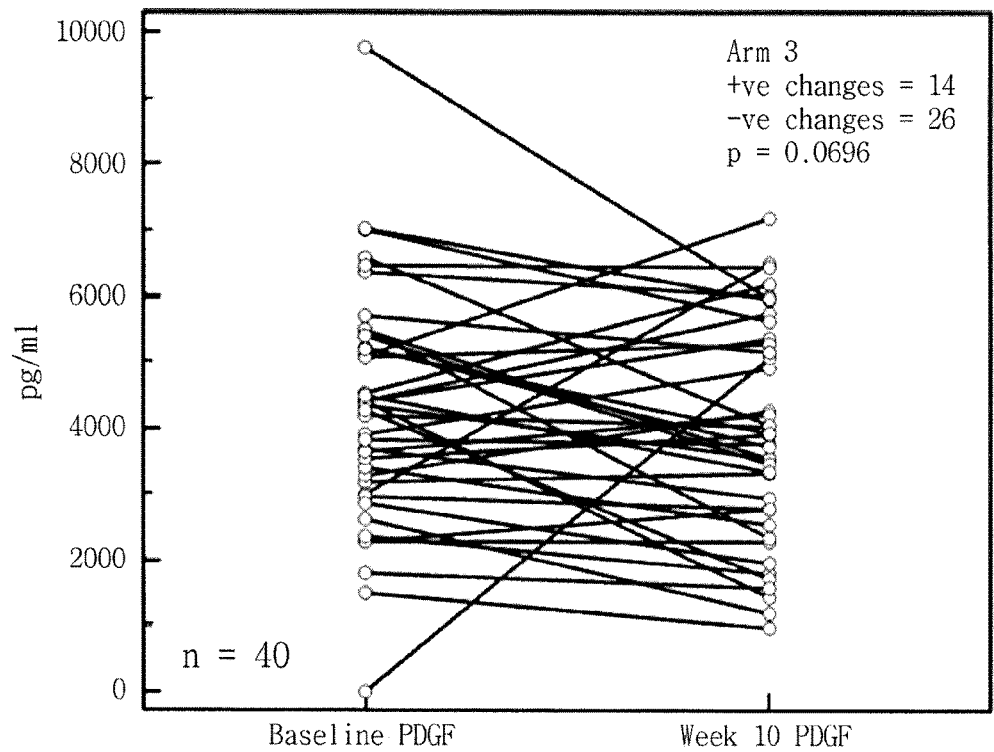

[Fig. 2e]
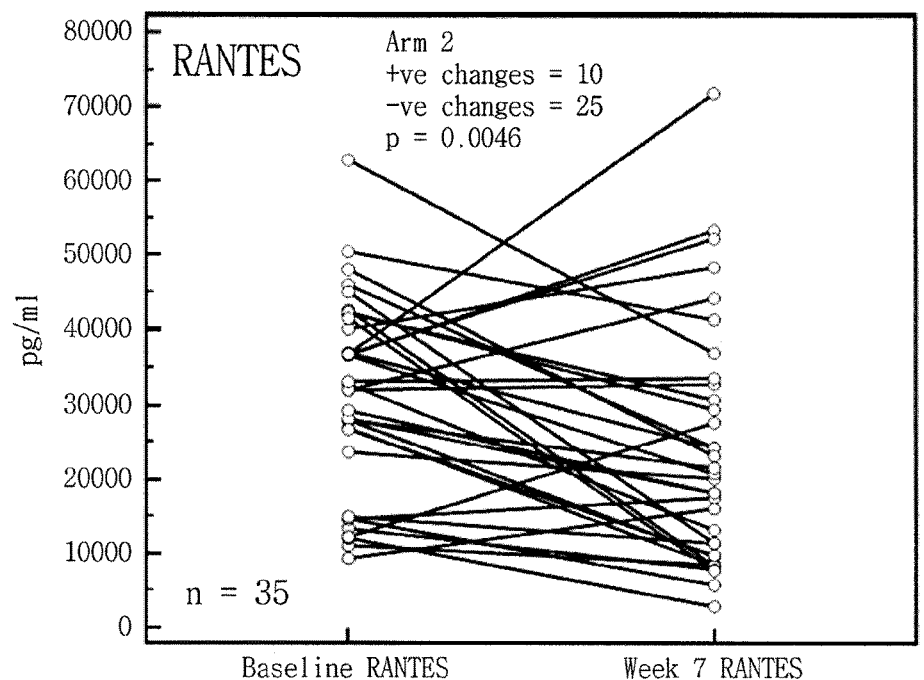
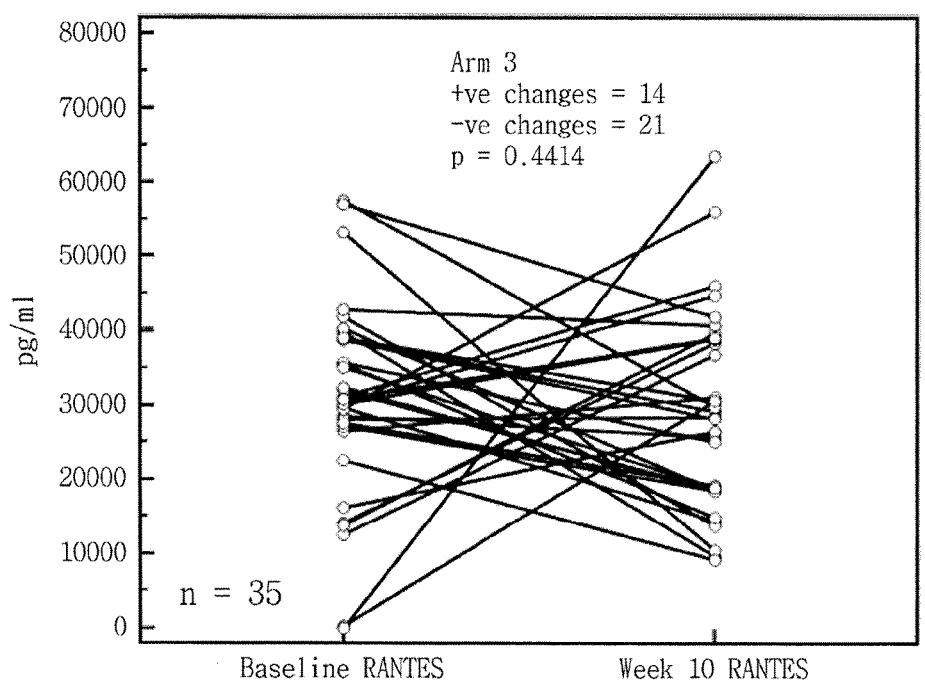

[Fig. 2f]
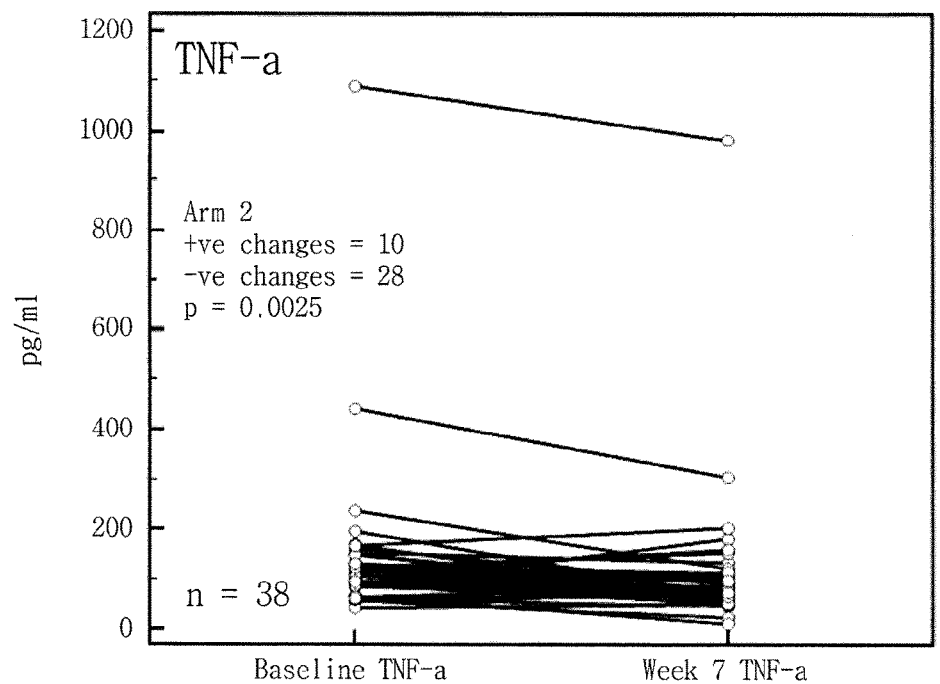
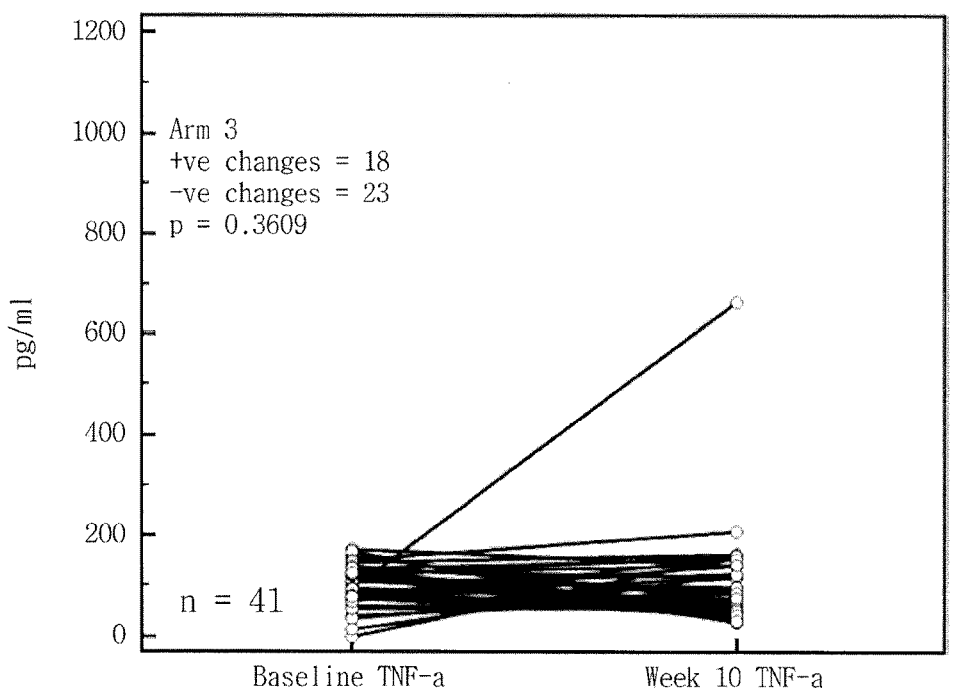

[Fig. 2g]
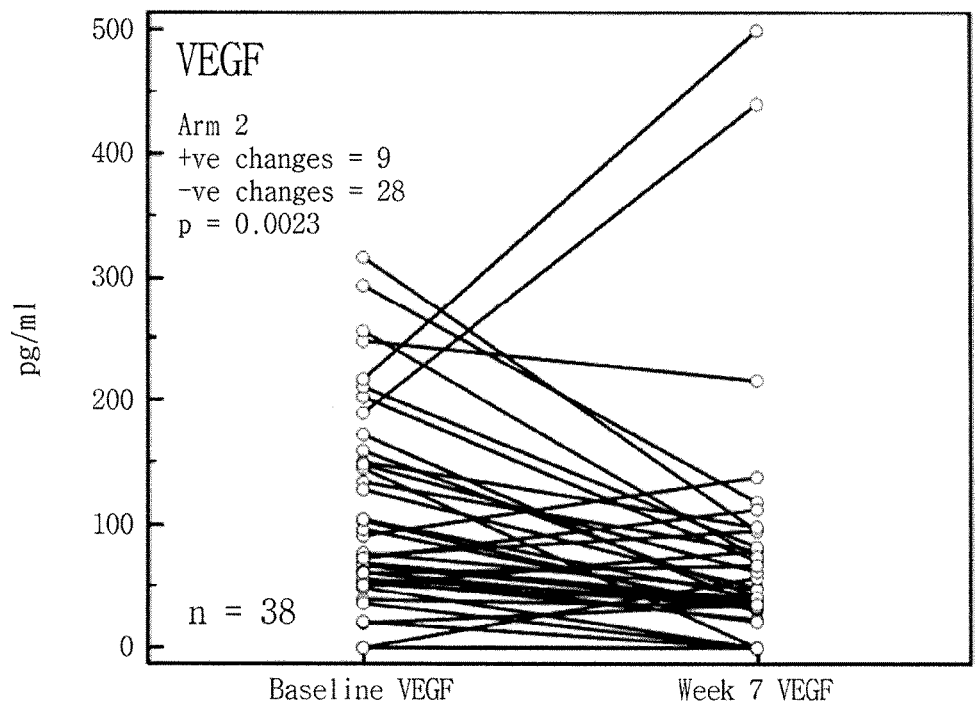
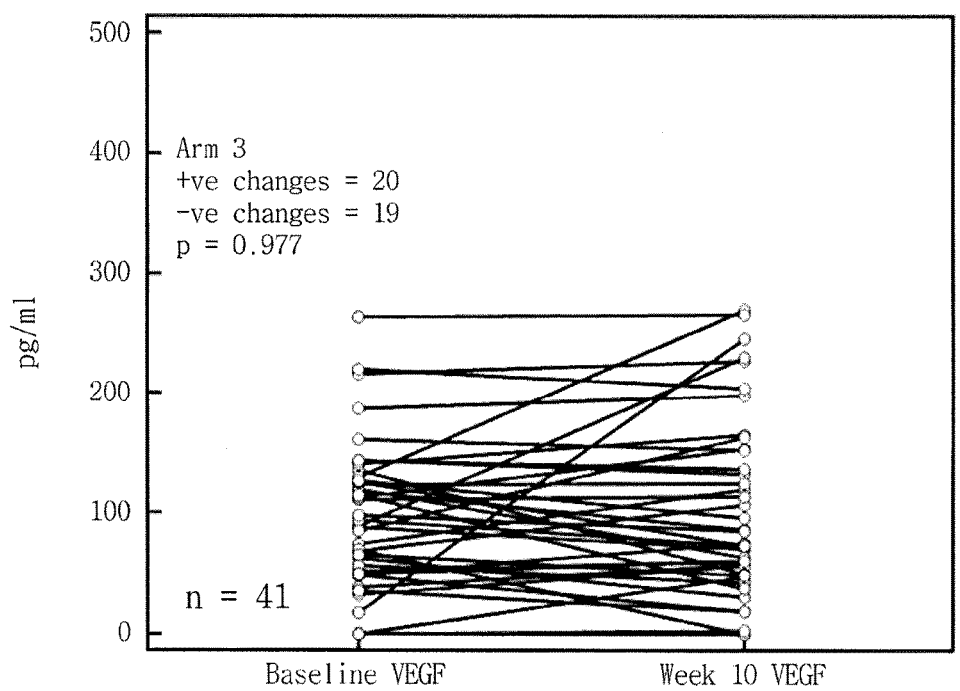

[Fig. 3]
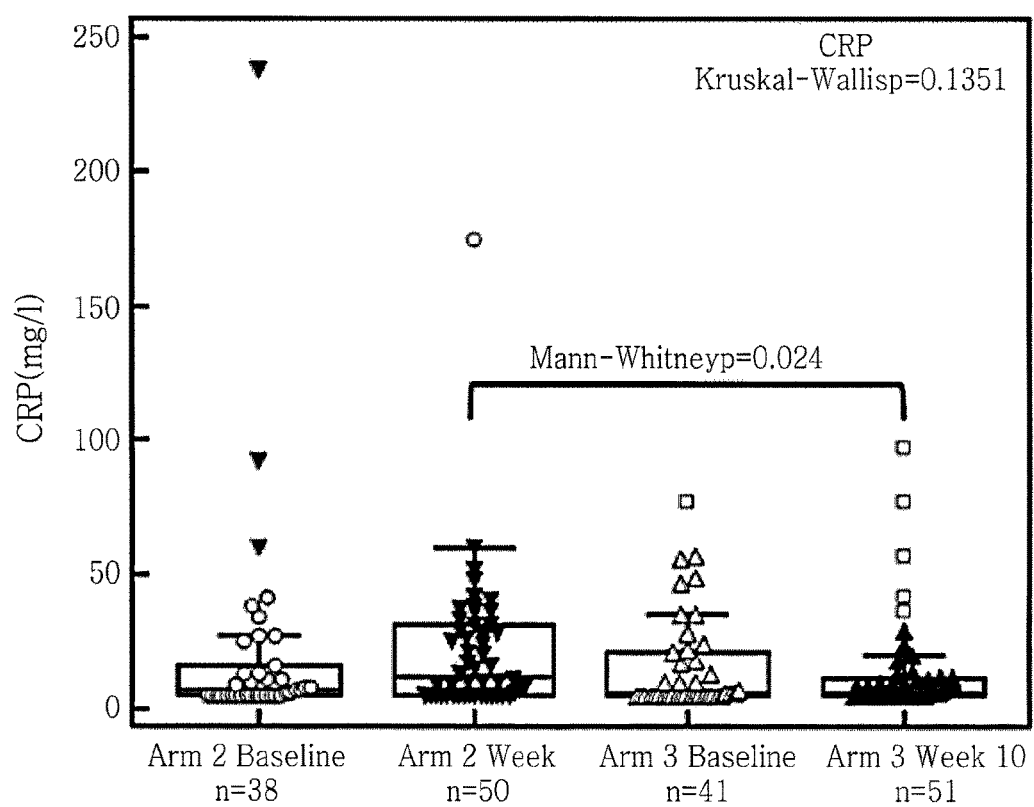

[Fig. 4]
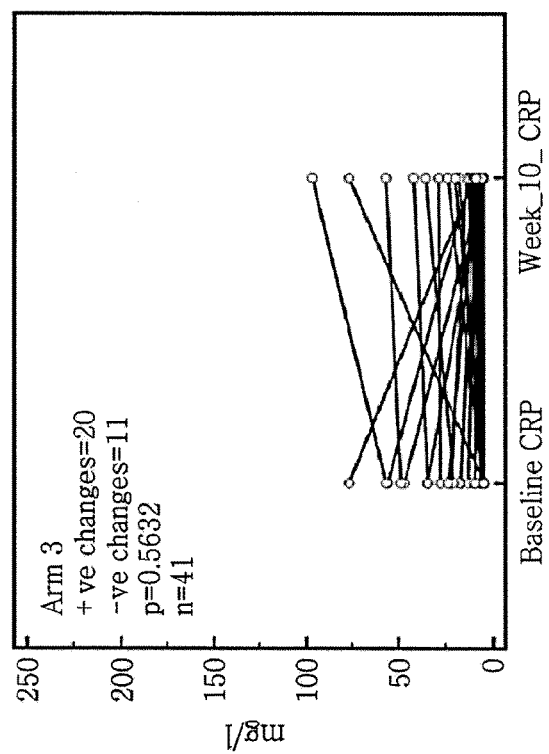
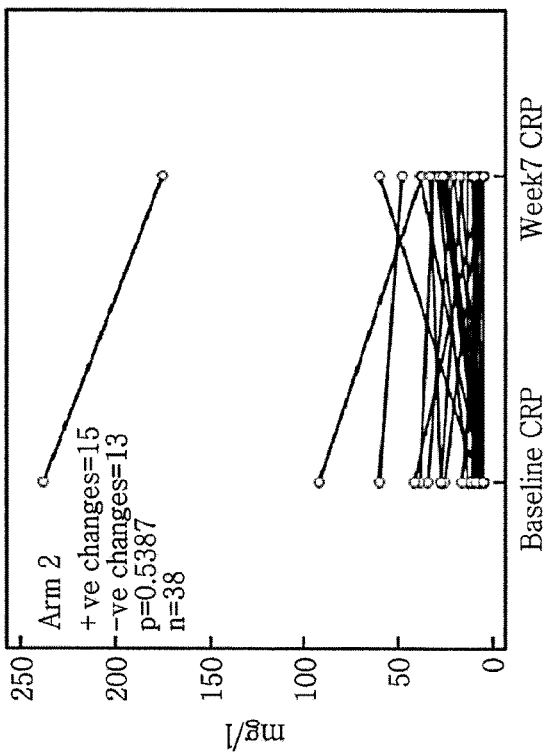

[Fig. 5a]
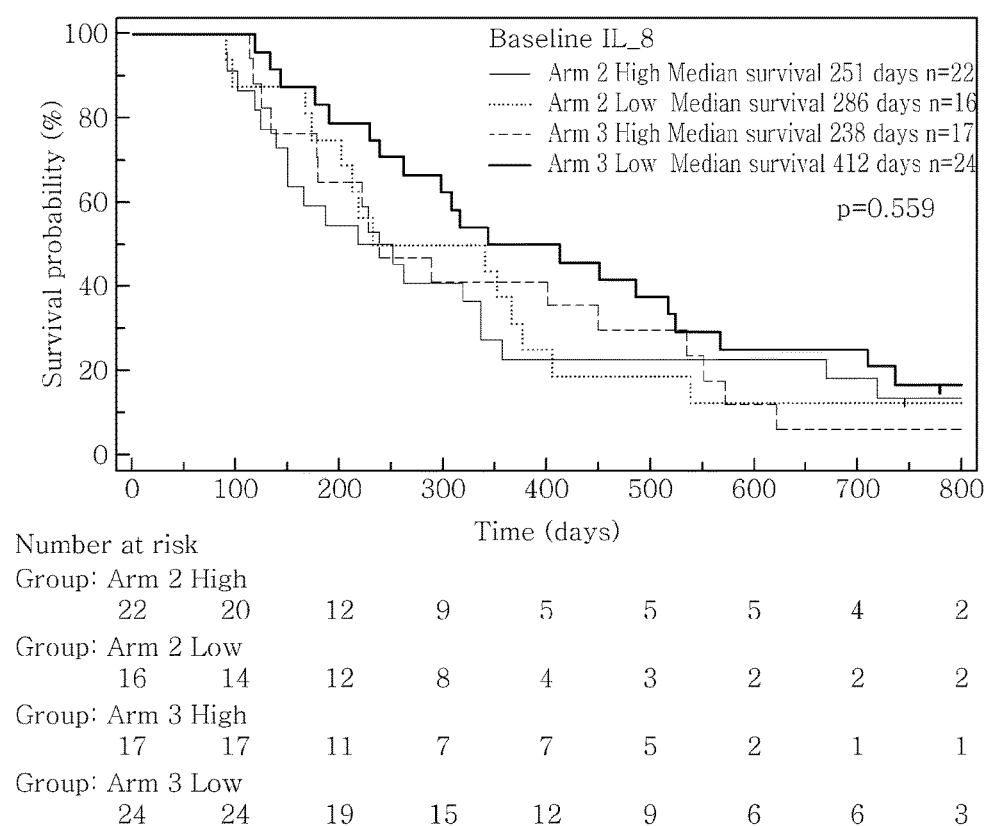

[Fig. 5b]
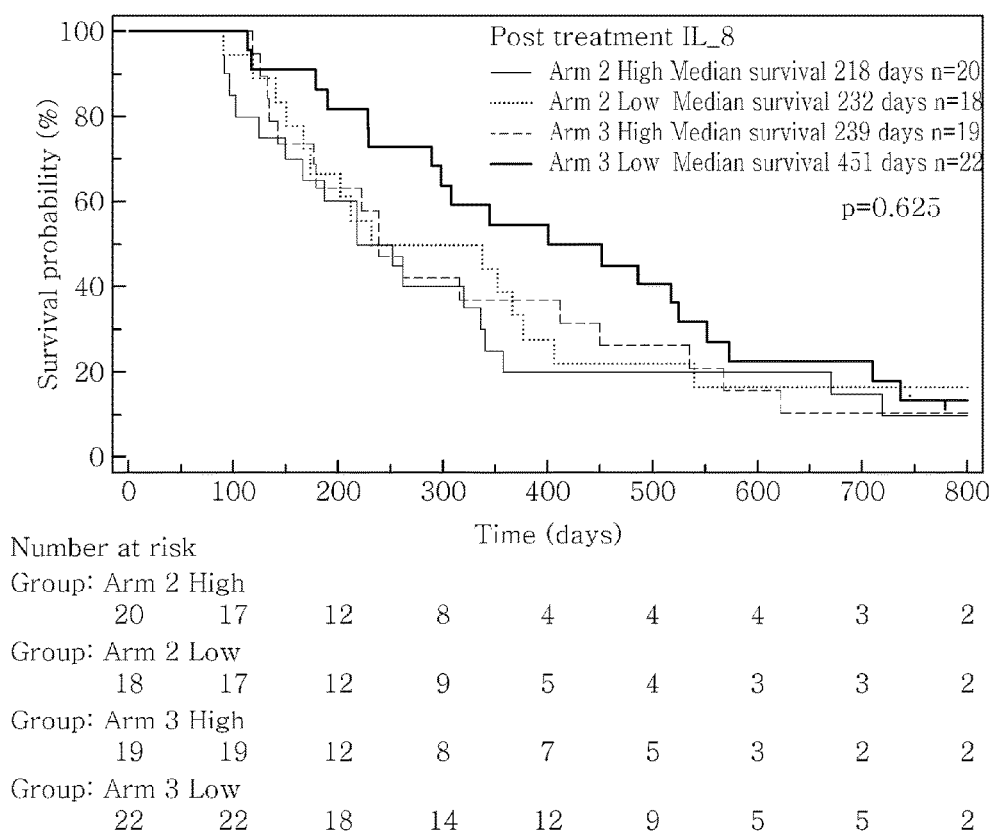

[Fig. 5c]
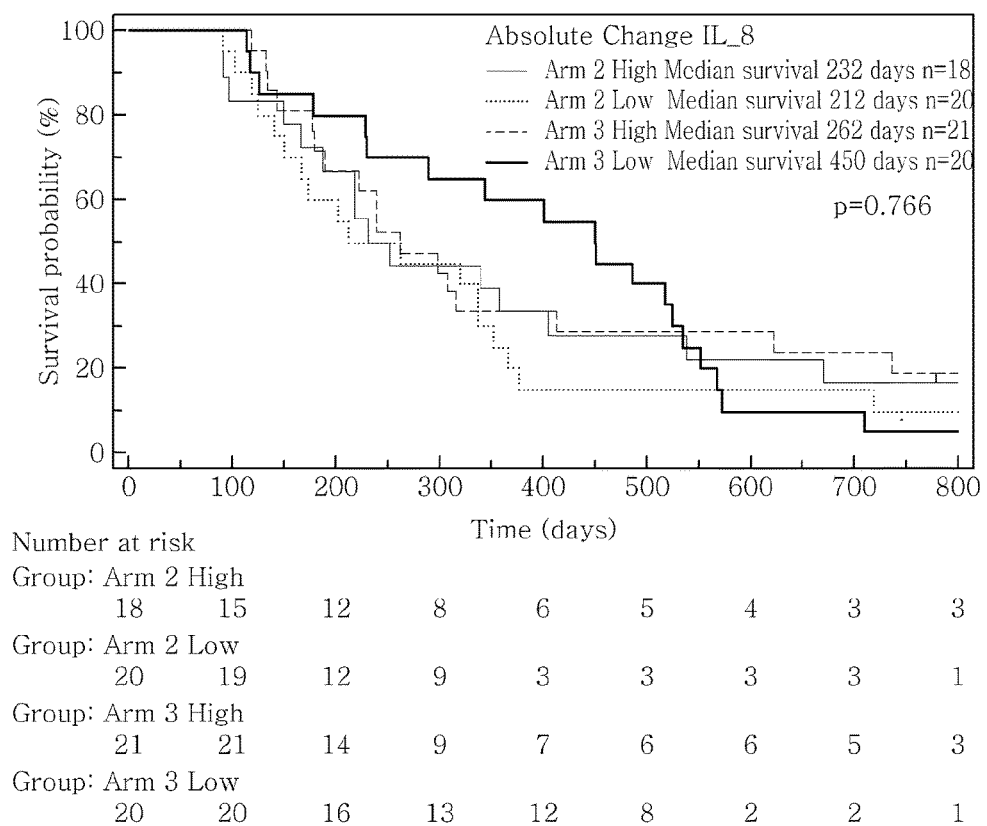

[Fig. 6a]
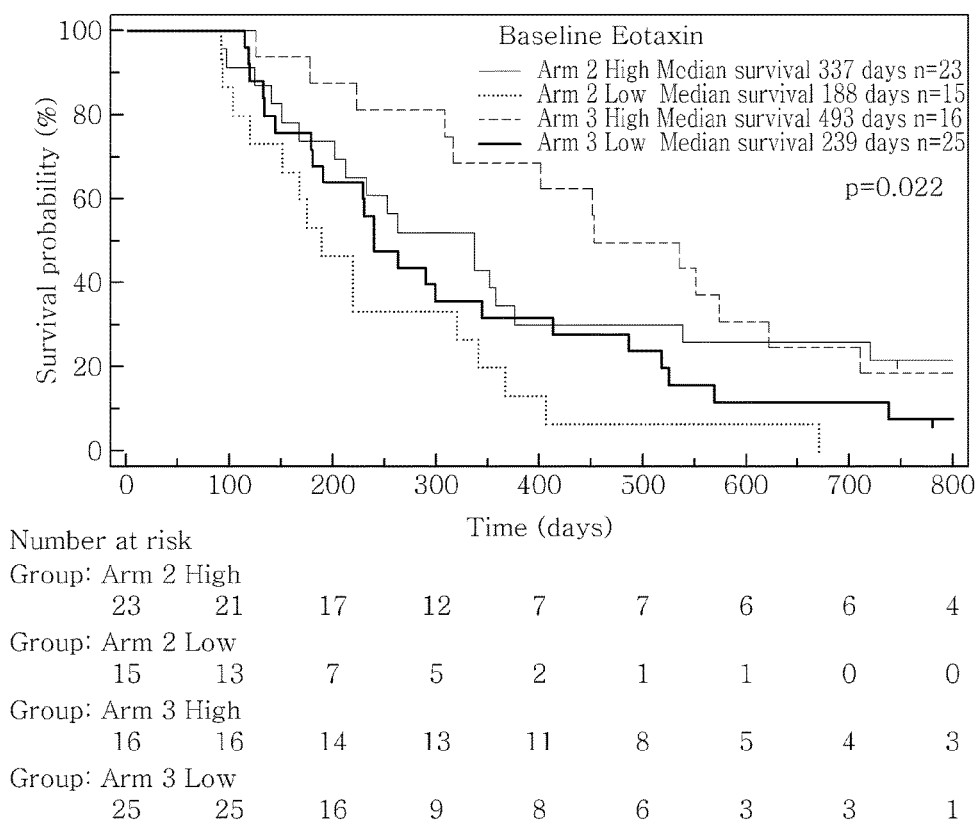

[Fig. 6b]
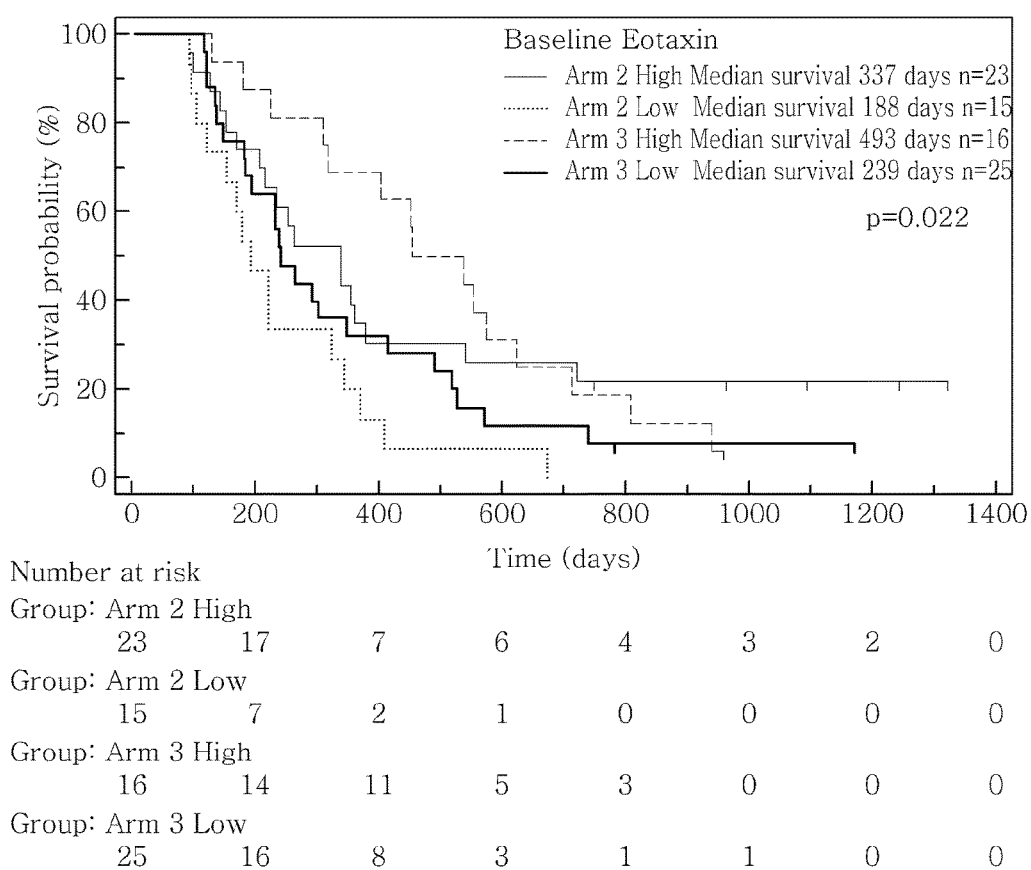

[Fig. 6c]
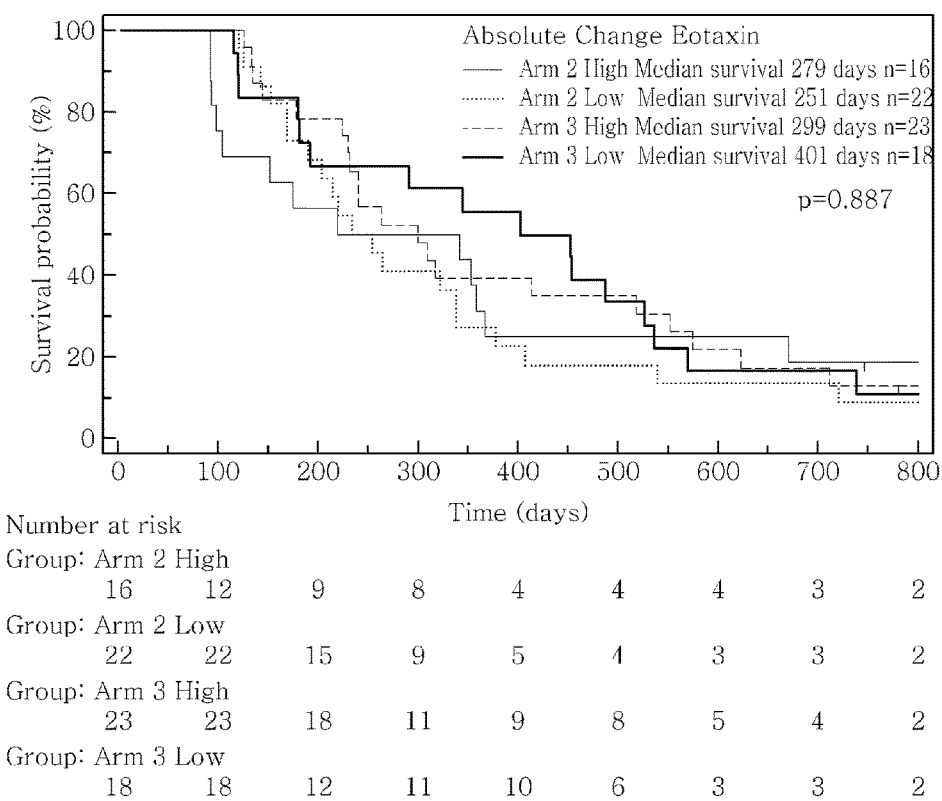

[Fig. 7a]
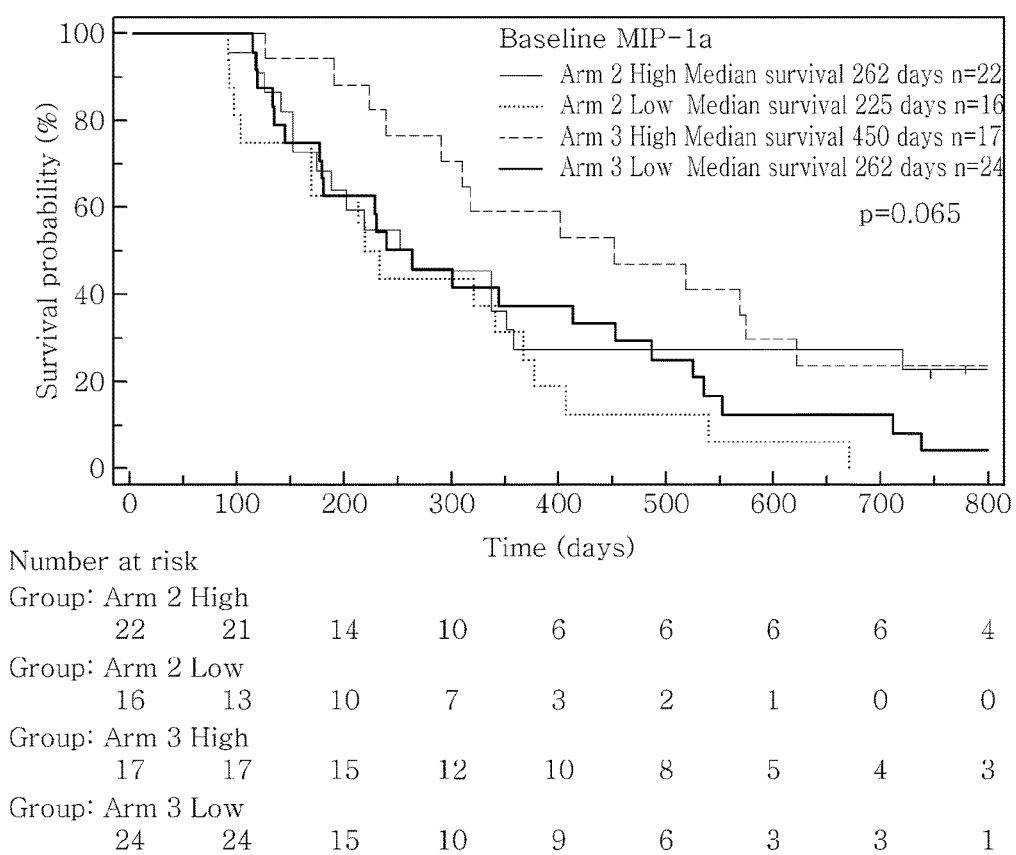

[Fig. 7b]
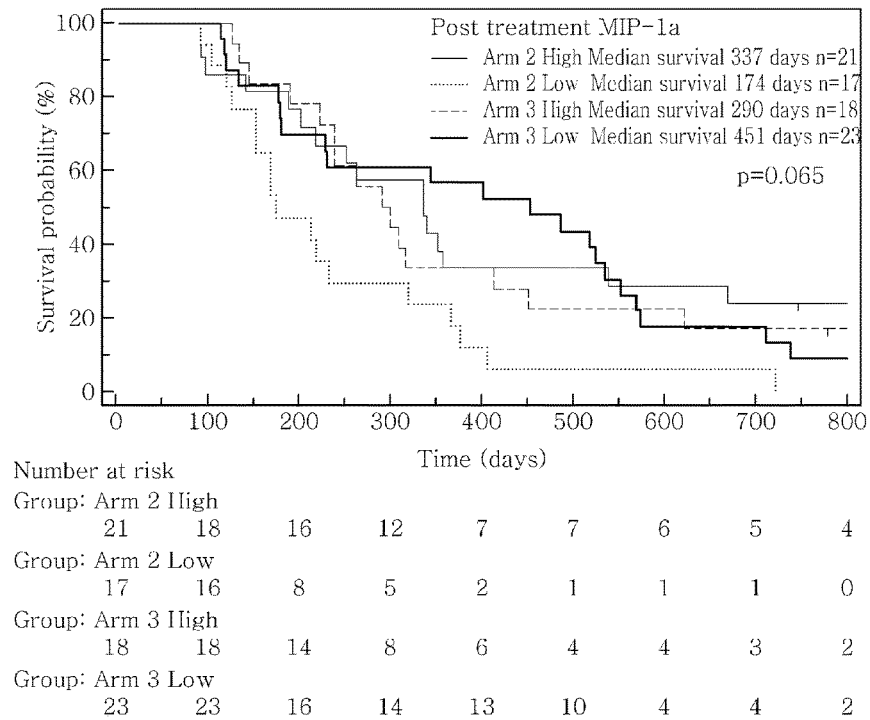
[Fig. 7c]
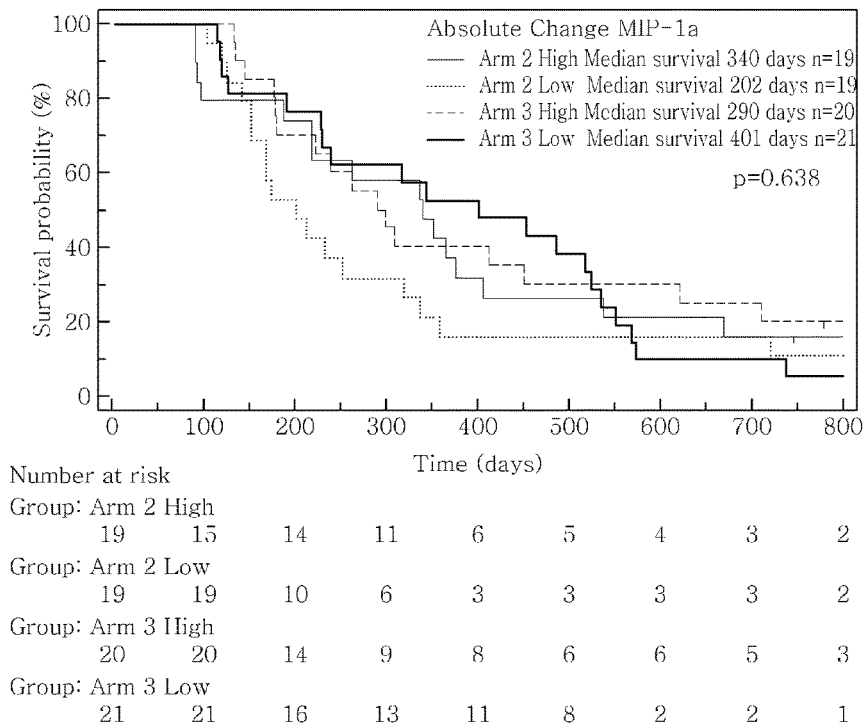

[Fig. 8a]
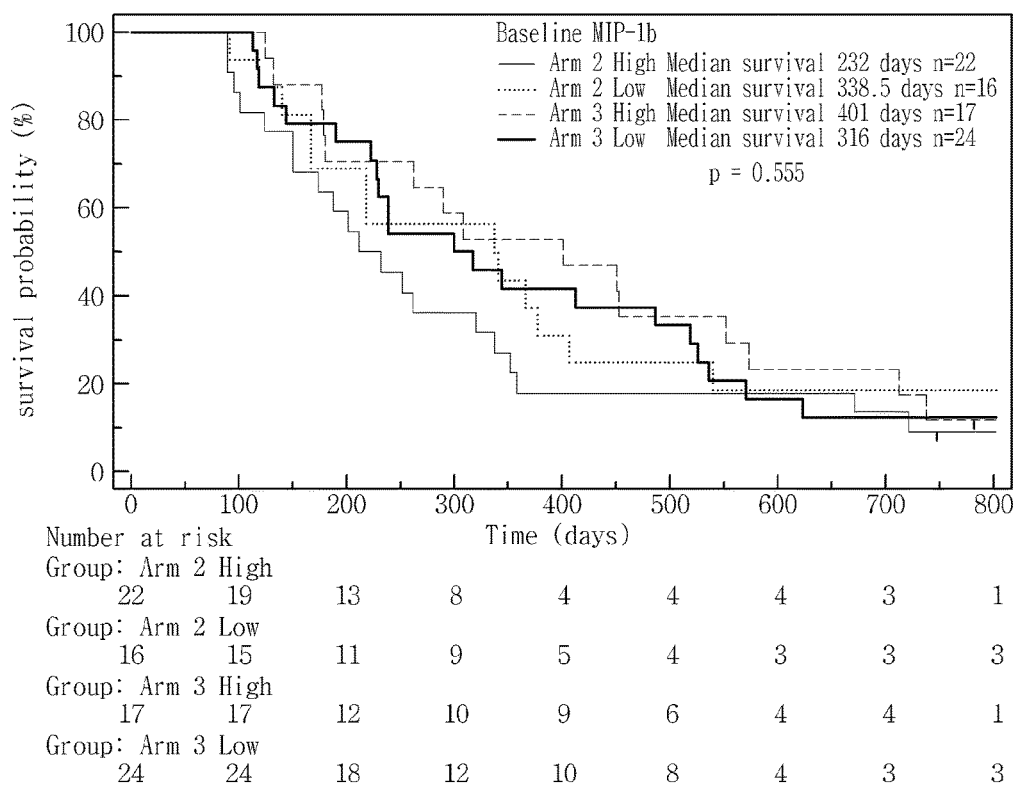

[Fig. 8b]
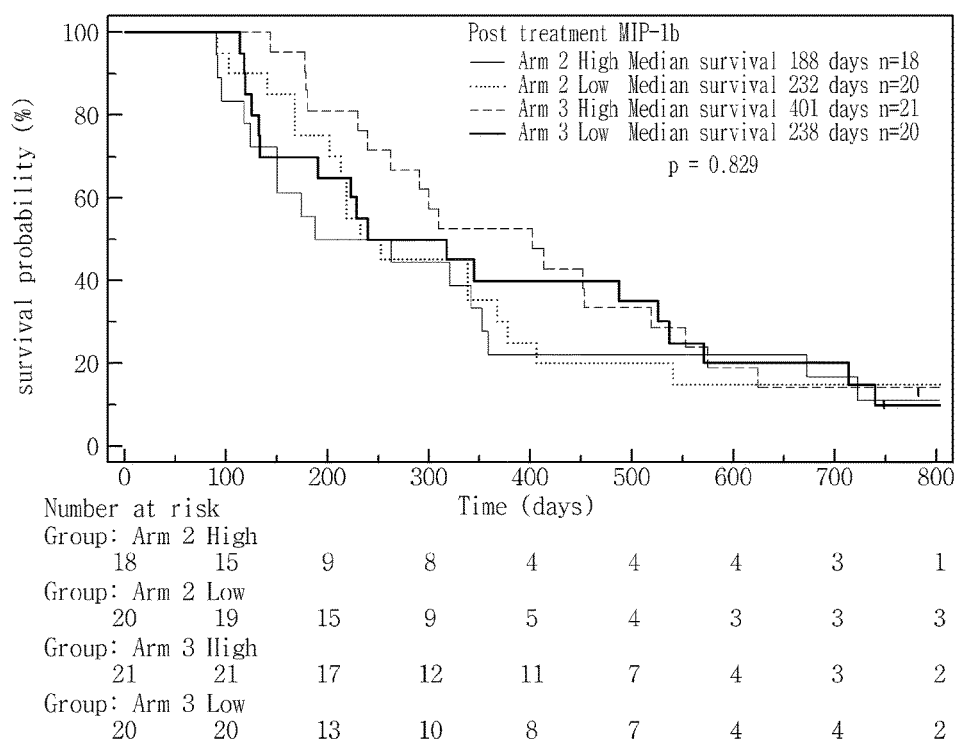

[Fig. 8c]
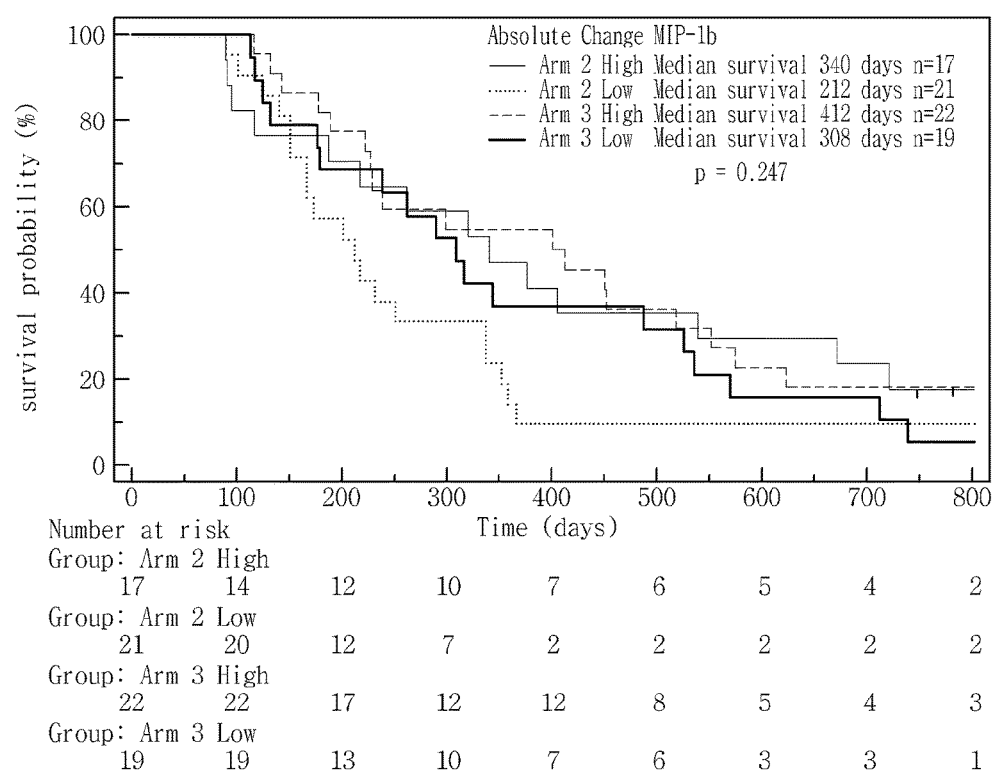

[Fig. 9a]
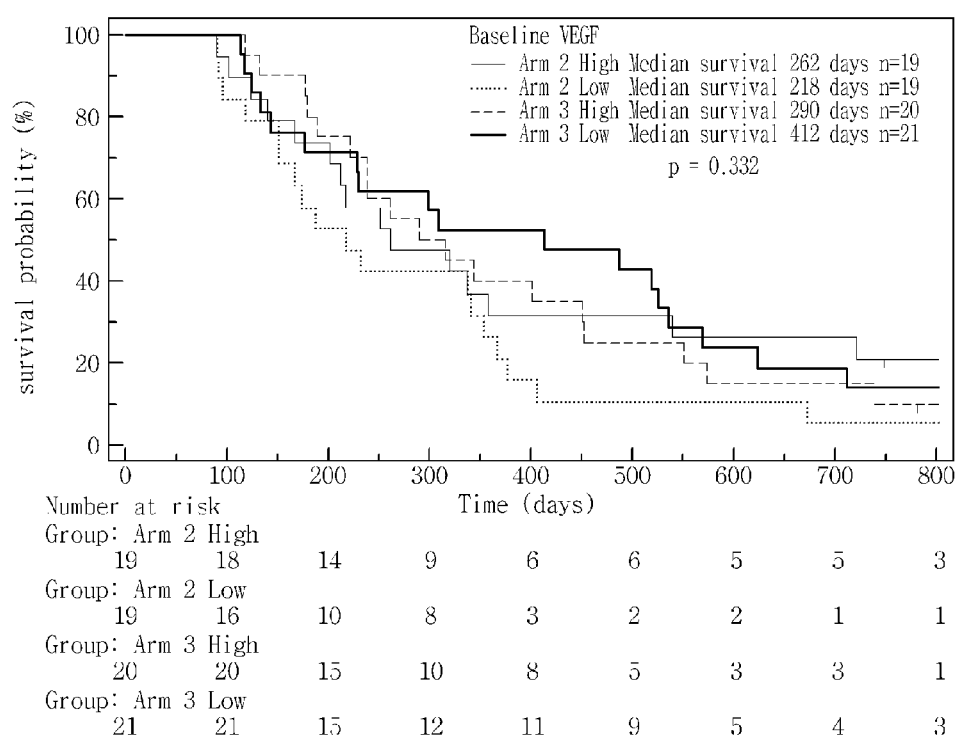

[Fig. 9b]
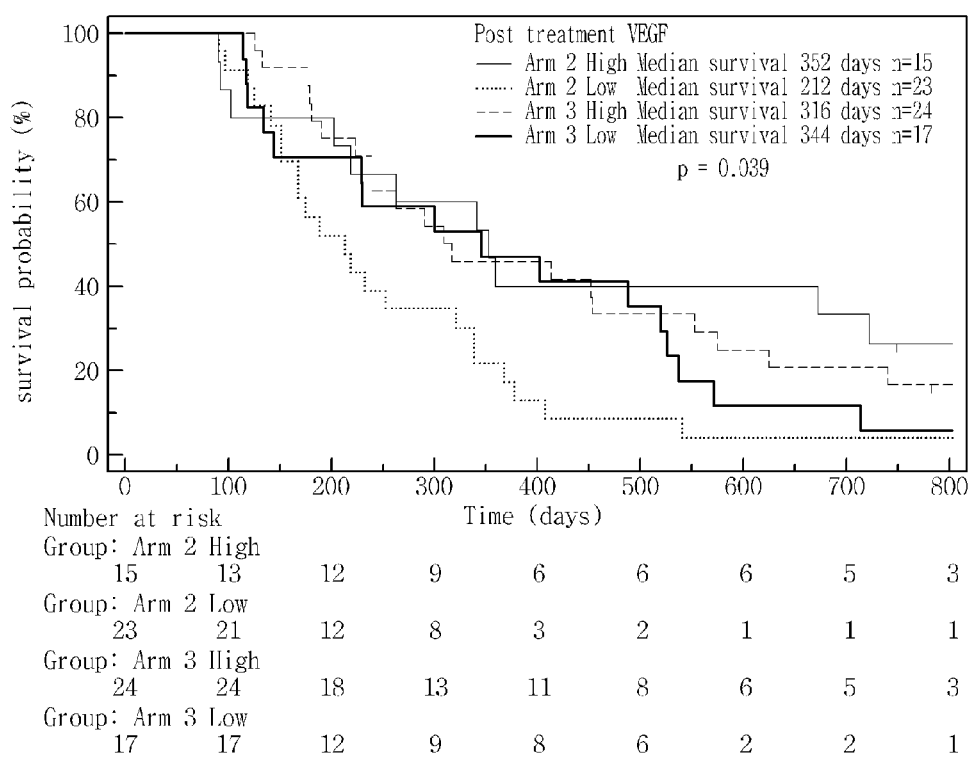

[Fig. 9c]
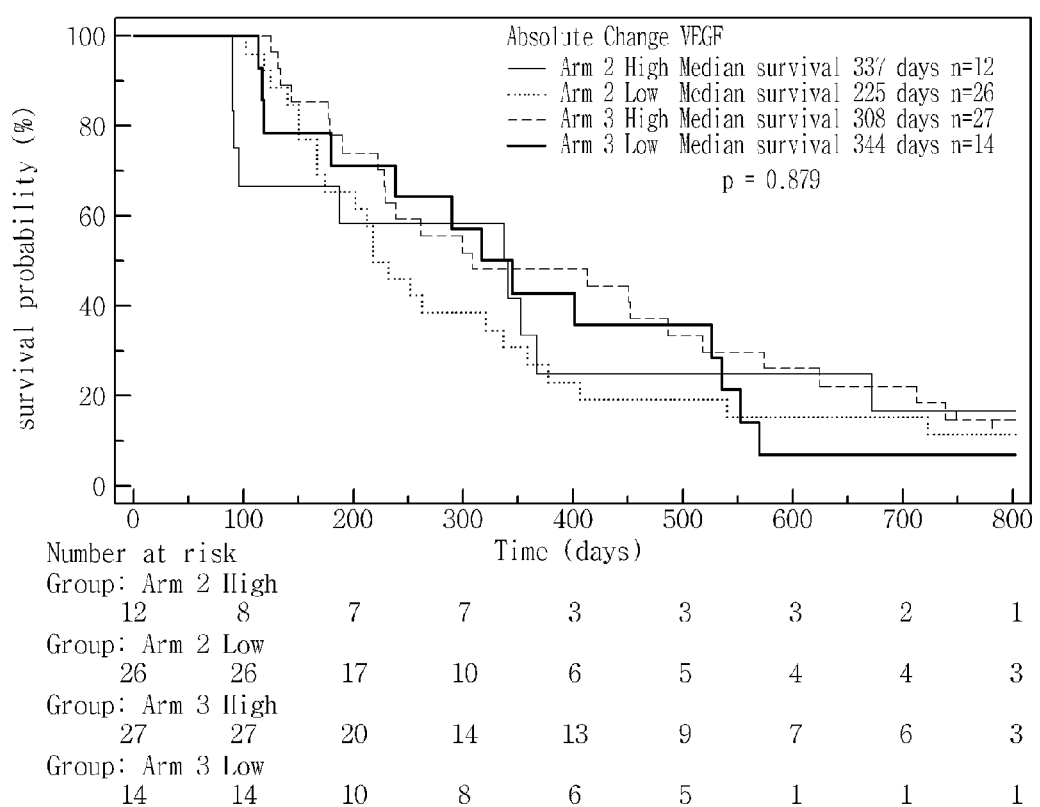

[Fig. 10a]
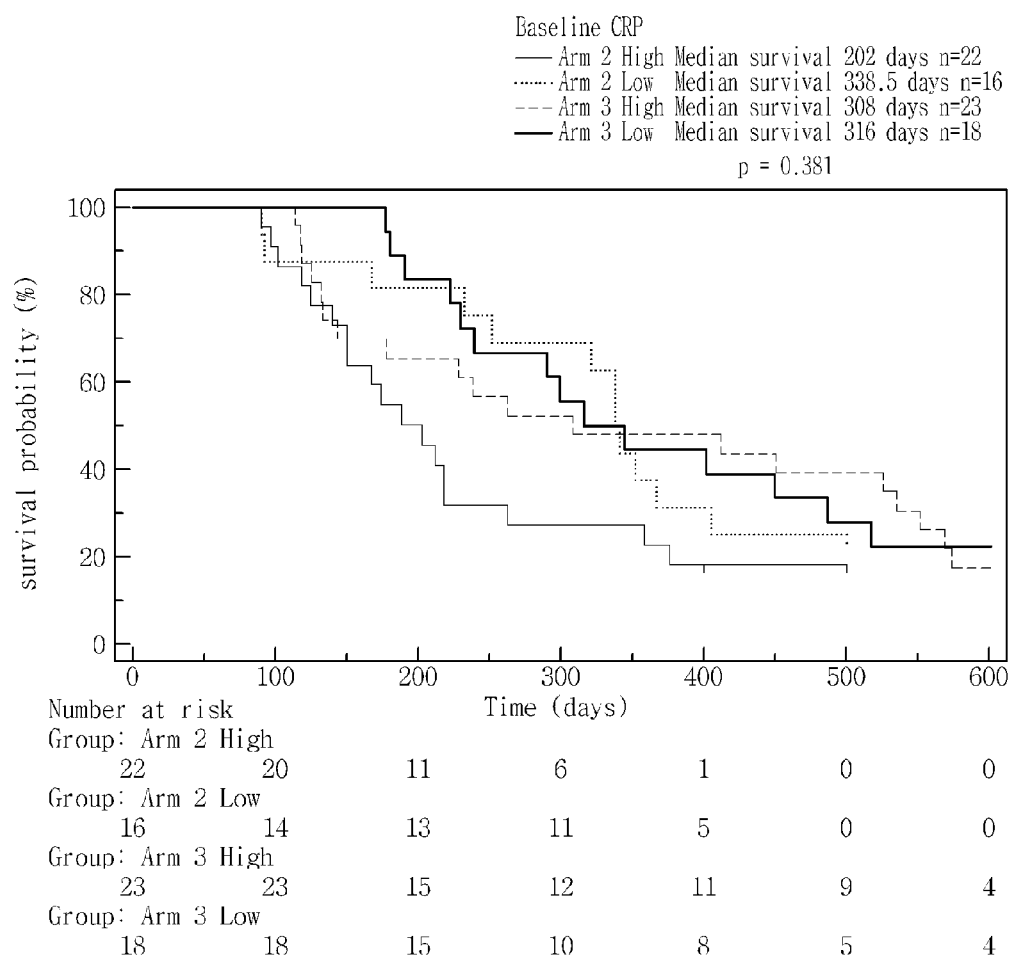

[Fig. 10b]
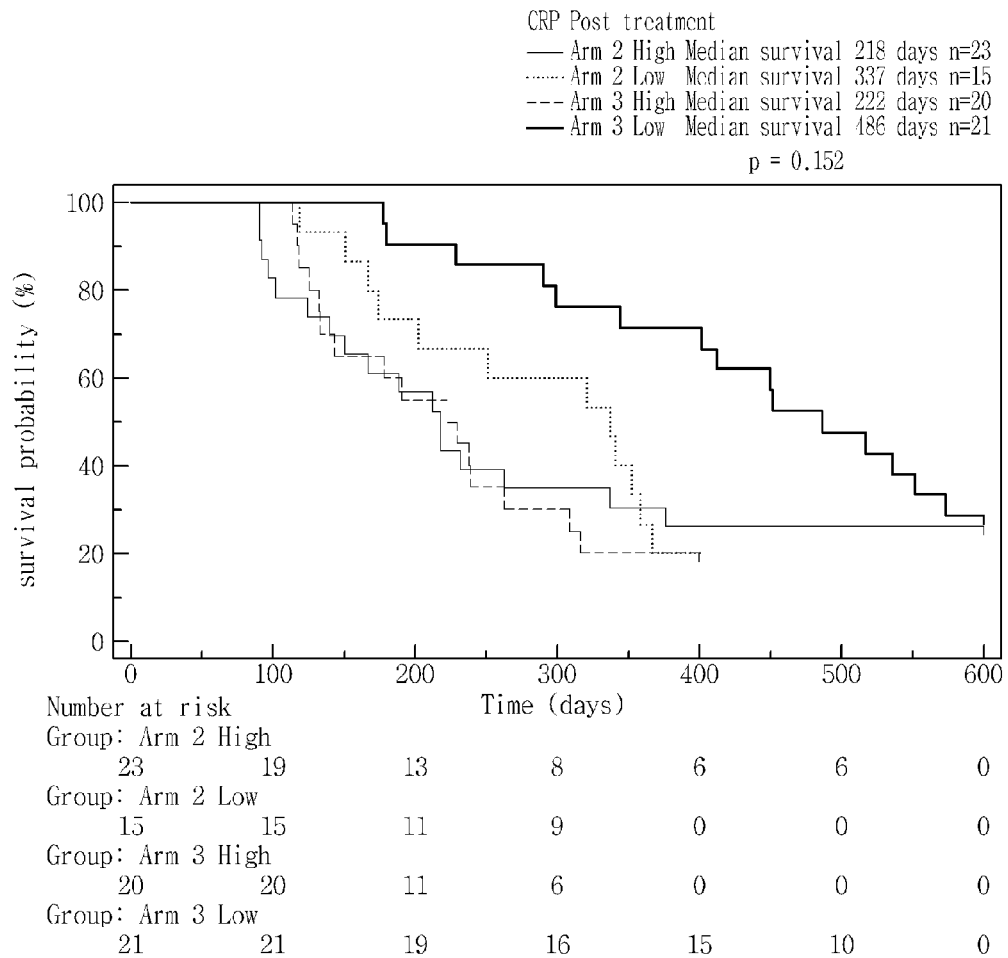

[Fig. 10c]
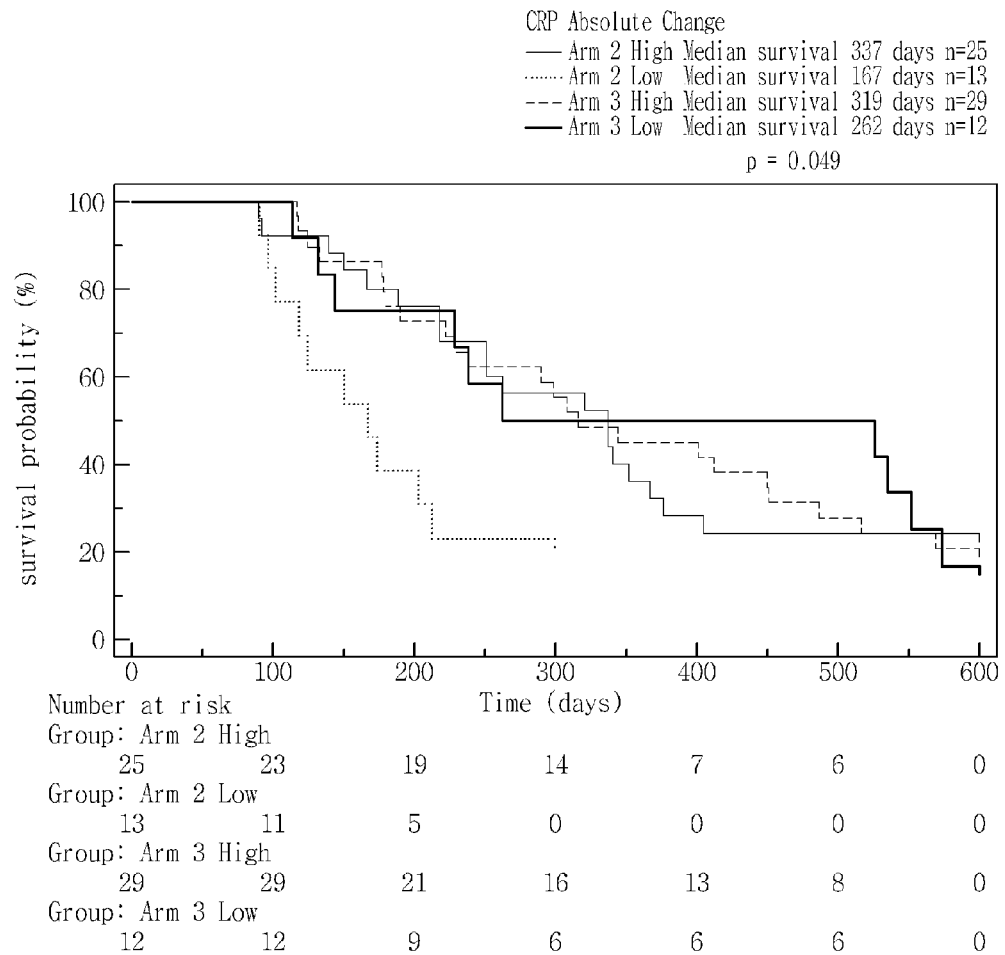

[Fig. 11]
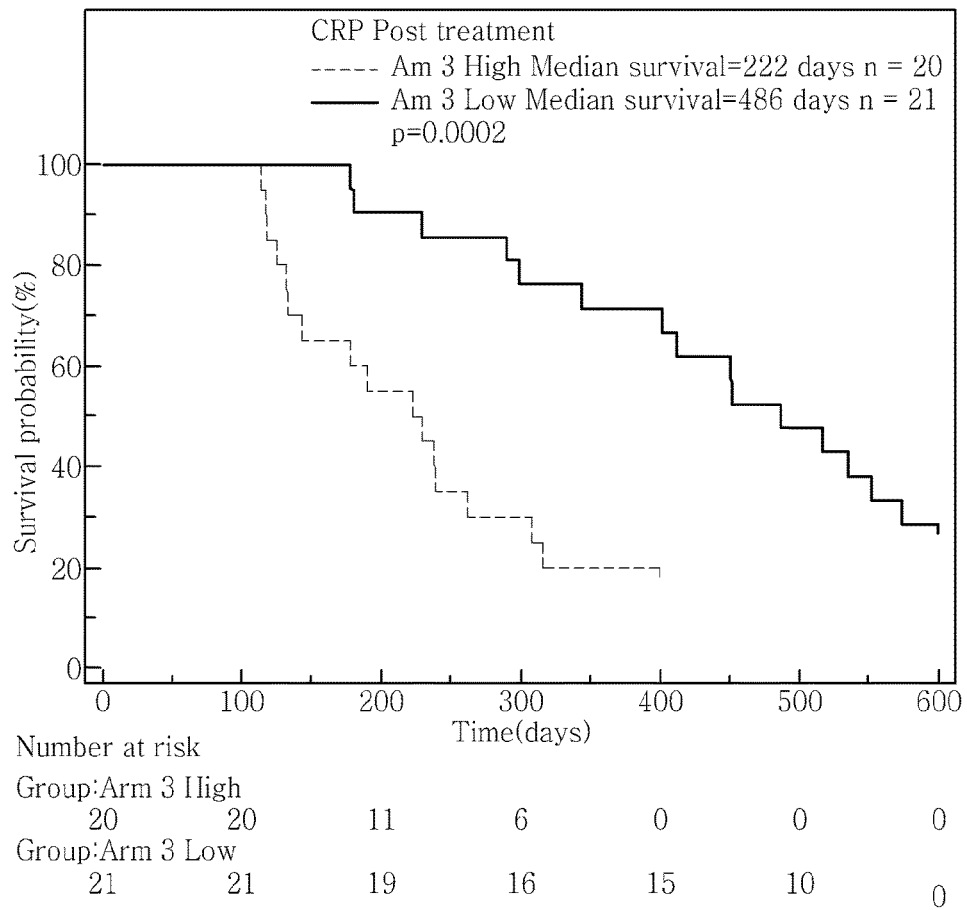
[Fig. 12a]
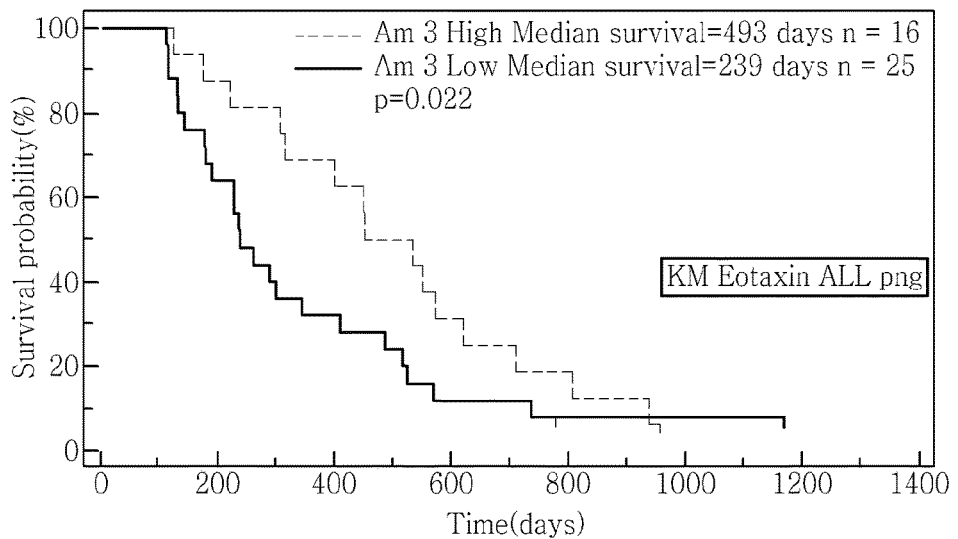

[Fig. 12b]
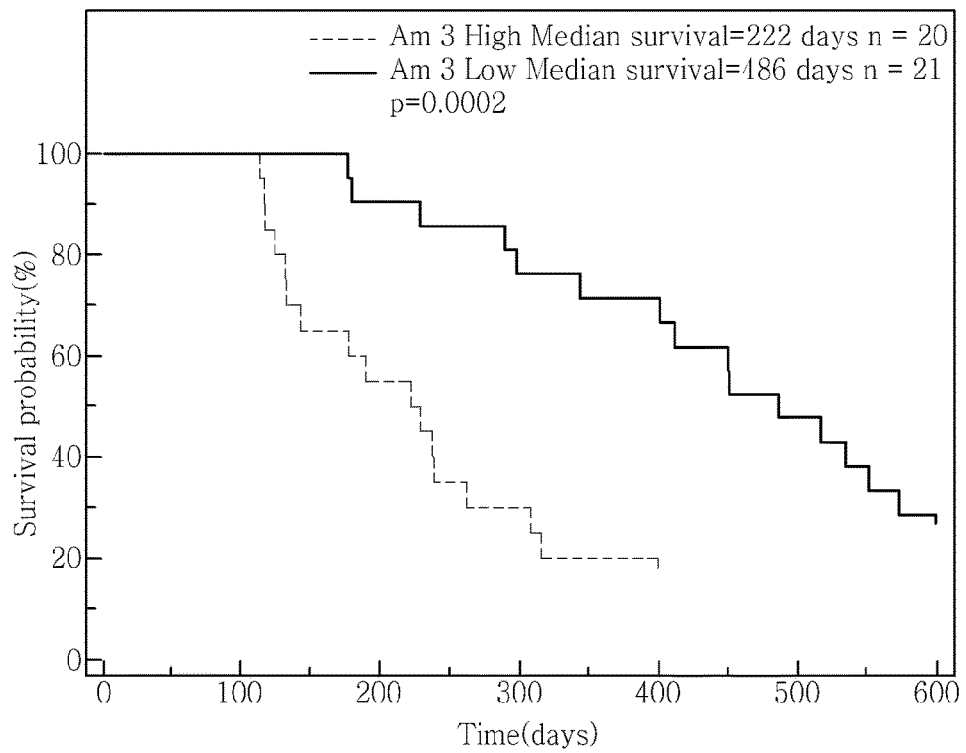
[Fig. 13]
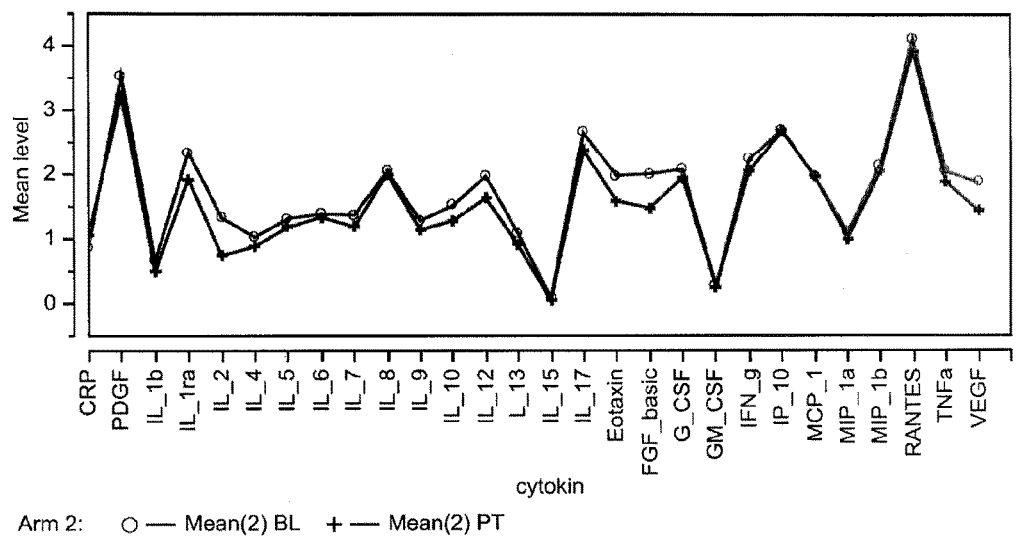

[Fig. 14]
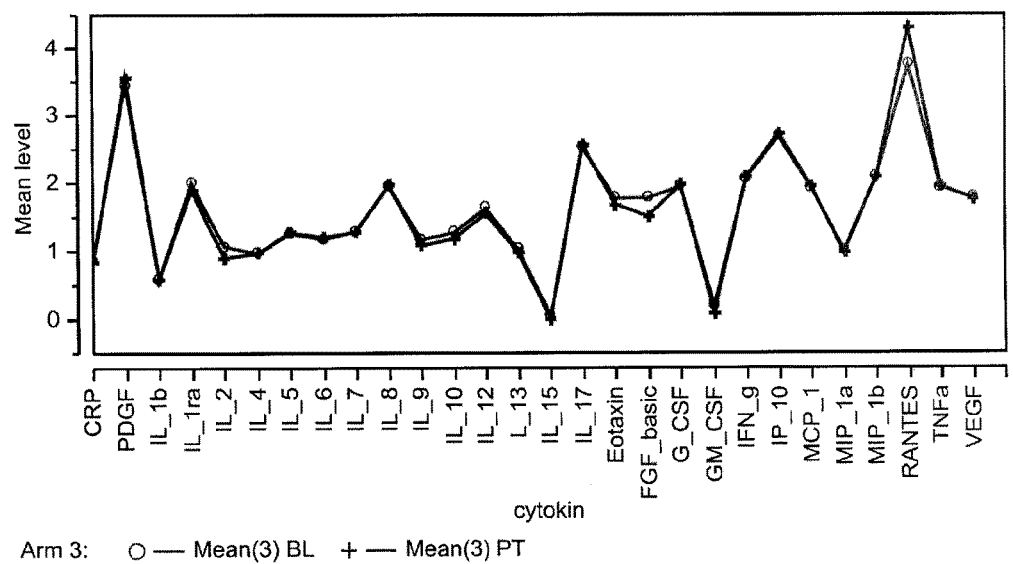
Arm 3: ○ —— Mean(3) BL    + —— Mean(3) PT
[Fig. 15]
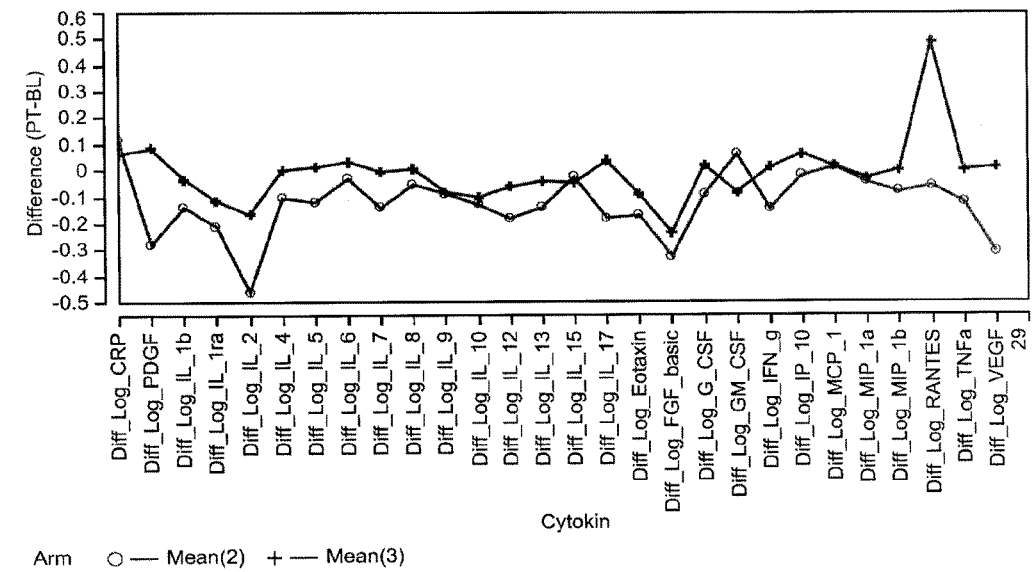
Arm    ○ —— Mean(2)    + —— Mean(3)

[Fig. 16]

| Wilcoxon signed rank p-values | | | | | |
|---|---|---|---|---|---|
| Cytokine | arm2 | arm3 | Cytokine | arm2 | arm3 |
| CRP | 0.526 | 0.451 | IL_15 | | |
| PDGF | <0.001 | 0.069 | IL_17 | <0.001 | 0.297 |
| IL_1b | 0.002 | 0.551 | Eotaxin | 0.003 | 0.834 |
| IL_1ra | 0.007 | 0.096 | FGF_basic | 0.011 | 0.253 |
| IL_2 | <0.001 | 0.242 | G_CSF | 0.002 | 0.240 |
| IL_4 | <0.001 | 0.381 | GM_CSF | 0.839 | 0.052 |
| IL_5 | <0.001 | 0.520 | IFN_g | <0.001 | 0.252 |
| IL_6 | 0.412 | 0.954 | IP_10 | 0.174 | 0.334 |
| IL_7 | 0.002 | 0.471 | MCP_1 | 0.938 | 0.698 |
| IL_8 | 0.061 | 0.309 | MIP_1a | 0.143 | 0.223 |
| IL_9 | 0.165 | 0.099 | MIP_1b | 0.001 | 0.432 |
| IL_10 | 0.012 | 0.225 | RANTES | 0.002 | 0.071 |
| IL_12 | 0.018 | 0.417 | TNFa | 0.002 | 0.367 |
| IL_13 | 0.044 | 0.403 | VEGF | 0.001 | 0.978 |

[Fig. 17]

| Median differences (PT - BL) red negative; blue positive or zero ; bold significant | | | | | |
|---|---|---|---|---|---|
| Cytokine | arm2 | arm3 | Cytokine | arm2 | arm3 |
| CRP | 0 | 1 | IL_15 | | |
| PDGF | -1555.3 | -448.5 | IL_17 | -145.0 | -41.6 |
| IL_1b | -0.9 | 0.0 | Eotaxin | -18.9 | -7.7 |
| IL_1ra | -44.3 | -35.3 | FGF_basic | -25.5 | -16.8 |
| IL_2 | -11.0 | 0.0 | G_CSF | -19.4 | -12.9 |
| IL_4 | -2.4 | -0.7 | GM_CSF | 0.0 | 0.0 |
| IL_5 | -4.4 | -1.0 | IFN_g | -31.6 | -12.9 |
| IL_6 | -1.8 | 0.9 | IP_10 | -62.7 | 27.5 |
| IL_7 | -6.4 | -2.6 | MCP_1 | -1.6 | -7.6 |
| IL_8 | -11.1 | 1.1 | MIP_1a | -1.0 | -1.2 |
| IL_9 | -4.0 | -3.0 | MIP_1b | -23.9 | -9.9 |
| IL_10 | -7.5 | -3.1 | RANTES | -9269.3 | -8497.3 |
| IL_12 | -25.0 | -11.4 | TNFa | -20.6 | -16.3 |
| IL_13 | -3.6 | -1.3 | VEGF | -31.9 | 0.0 |

[Fig. 18]

| Baseline | | | | | |
|---|---|---|---|---|---|
| | HR(95%CI) Arm 2 | p-value | | HR(95%CI) Arm 3 | p-value |
| CRP | 2.71 (1.24-05.78) | 0.013 | | 3.65 (1.68-7.89) | 0.001 |
| PDGF | 0.53 (0.11-3.14) | 0.467 | | 0.68 (0.44-1.25) | 0.180 |
| IL_1b | 0.58 (0.24-1.24) | 0.174 | | 0.98 (0.31-3.47) | 0.968 |
| IL_1ra | 0.43 (0.18-0.89) | 0.021 | | 0.56 (0.32-1.11) | 0.091 |
| IL_2 | 0.62 (0.36-1.07) | 0.083 | | 0.80 (0.47-1.45) | 0.453 |
| IL_4 | 0.55 (0.04-6.31) | 0.642 | | 0.57 (0.14-3.54) | 0.509 |
| IL_5 | 1.17 (0.05-26.69) | 0.922 | | 0.60 (0.20-2.78) | 0.469 |
| IL_6 | 0.48 (0.15-1.17) | 0.119 | | 1.25 (0.37-5.46) | 0.743 |
| IL_7 | 1.92 (0.26-14.42) | 0.522 | | 0.80 (0.28-2.81) | 0.715 |
| IL_8 | 4.11 (0.49-35.80) | 0.194 | | 0.89 (0.28-4.64) | 0.870 |
| IL_9 | 0.98 (0.36-2.78) | 0.973 | | 0.81 (0.23-3.04) | 0.752 |
| IL_10 | 0.47 (0.21-1.04) | 0.062 | | 1.40 (0.55-3.56) | 0.483 |
| IL_12 | 0.63 (0.33-1.19) | 0.155 | | 0.85 (0.45-1.75) | 0.640 |
| IL_13 | 0.92 (0.19-4.38) | 0.913 | | 0.88 (0.32-2.52) | 0.803 |
| IL_17 | 0.39 (0.05-2.49) | 0.332 | | 0.58 (0.28-1.68) | 0.262 |
| Eotaxin | 0.46 (0.21-1.00) | 0.050 | | 0.35 (0.19-0.69) | 0.004 |
| FGF_basic | 0.80 (0.33-2.15) | 0.652 | | 0.83 (0.47-1.70) | 0.571 |
| G_CSF | 1.05 (0.25-3.89) | 0.944 | | 0.56 (0.24-1.80) | 0.291 |
| IFN_g | 0.31 (0.05-1.12) | 0.077 | | 0.64 (0.29-1.87) | 0.369 |
| IP_10 | 1.27 (0.29-4.76) | 0.736 | | 0.68 (0.28-1.92) | 0.442 |
| MCP_1 | 0.96 (0.35-3.43) | 0.951 | | 0.95 (0.16-7.23) | 0.960 |
| MIP_1a | 0.93 (0.31-2.96) | 0.907 | | 0.79 (0.14-4.62) | 0.788 |
| MIP_1b | 2.76 (0.34-23.20) | 0.346 | | 0.34 (0.09-1.72) | 0.179 |
| RANTES | 1.12 (0.86-1.65) | 0.438 | | 0.99 (0.83-1.21) | 0.912 |
| TNFa | 0.49 (0.11-1.61) | 0.257 | | 0.65 (0.25-2.36) | 0.475 |
| VEGF | 0.66 (0.38-1.27) | 0.193 | | 0.86 (0.53-1.53) | 0.574 |

[Fig. 19a]
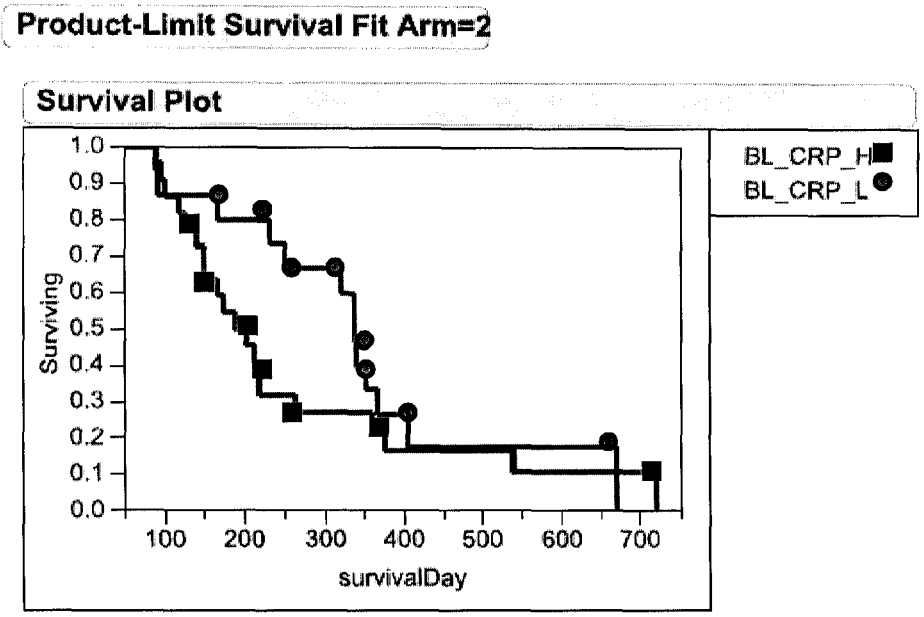

[Fig. 19b]
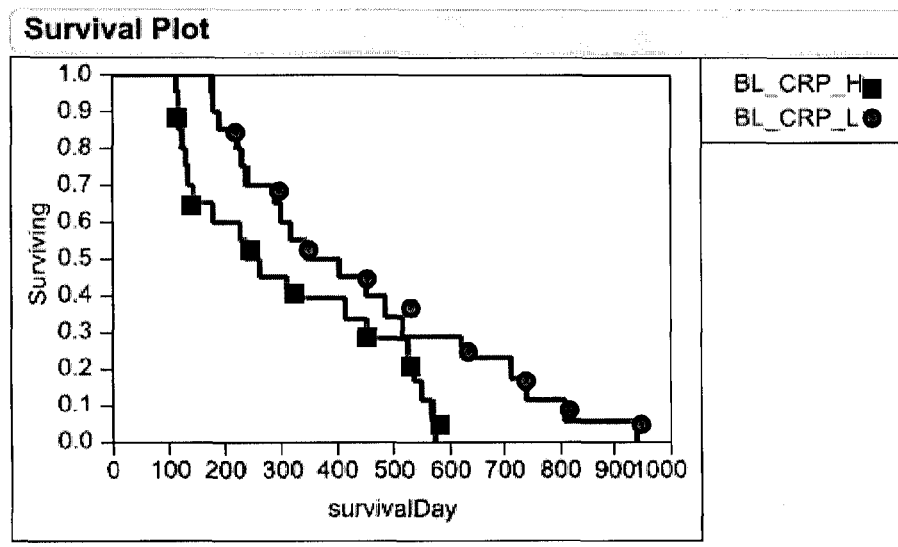
Product-Limit Survival Fit Arm=3
Survival Plot
Summary
| Group | Number failed | Number censored | Mean | Std Error |
|---|---|---|---|---|
| BL_CRP_H | 19 | 2 | 310 | 41 |
| BL_CRP_L | 19 | 1 | 442 | 54 |
| Combined | 38 | 3 | 376 | 35 |
Quantiles
| Group | Median Time | Lower 95% | Upper 95% | 25% Failures | 75% Failures |
|---|---|---|---|---|---|
| BL_CRP_H | 250 | 132 | 451 | 132.5 | 525 |
| BL_CRP_L | 372.5 | 229 | 517 | 234 | 623 |
| Combined | 308 | 229 | 451 | 185 | 535 |
Tests Between Groups
| Test | ChiSquare | DF | Prob>ChiSq |
|---|---|---|---|
| Log-Rank | 3.8417 | 1 | 0.0500 * |
| Wilcoxon | 3.5008 | 1 | 0.0613 |

[Fig. 20a]
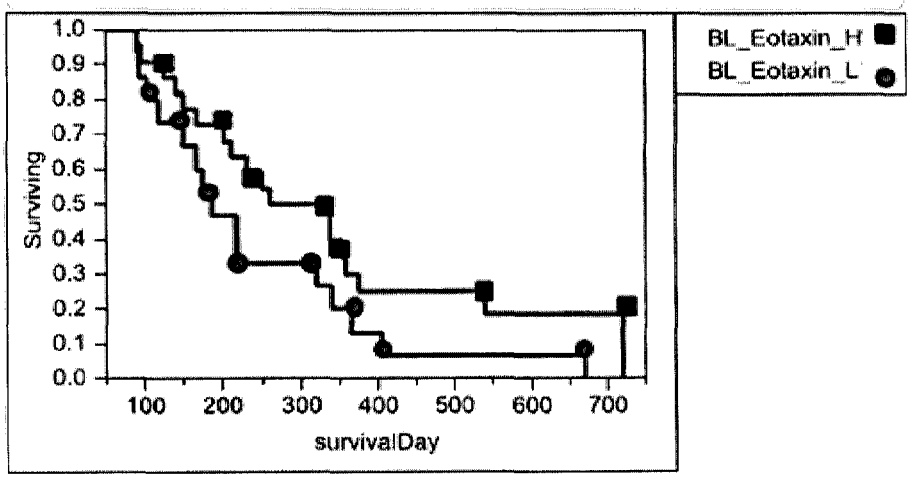
Summary
| Group | Number failed | Number censored | Mean | Std Error |
|---|---|---|---|---|
| BL_Eotaxin_H | 18 | 5 | 344 | 47 |
| BL_Eotaxin_L | 15 | 0 | 241 | 40 |
| Combined | 33 | 5 | 299 | 32 |
Quantiles
| Group | Median Time | Lower 95% | Upper 95% | 25% Failures | 75% Failures |
|---|---|---|---|---|---|
| BL_Eotaxin_H | 299.5 | 167 | 358 | 167 | 457 |
| BL_Eotaxin_L | 188 | 102 | 320 | 118 | 340 |
| Combined | 232 | 174 | 337 | 150 | 366 |
Tests Between Groups
| Test | ChiSquare | DF | Prob>ChiSq |
|---|---|---|---|
| Log-Rank | 2.5012 | 1 | 0.1138 |
| Wilcoxon | 2.0452 | 1 | 0.1527 |

[Fig. 20b]
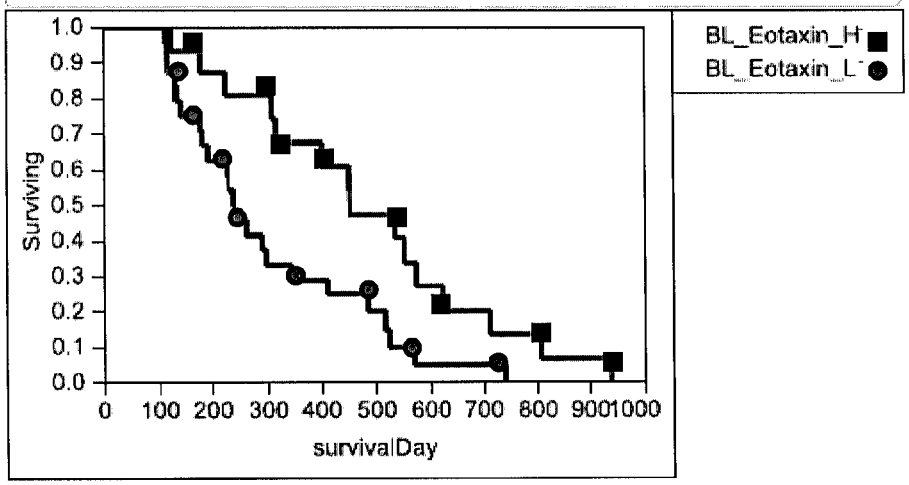
Product-Limit Survival Fit Arm=3
Summary
| Group | Number failed | Number censored | Mean | Std Error |
|---|---|---|---|---|
| BL_Eotaxin_H | 15 | 1 | 484 | 59 |
| BL_Eotaxin_L | 23 | 2 | 302 | 37 |
| Combined | 38 | 3 | 376 | 35 |
Quantiles
| Group | Median Time | Lower 95% | Upper 95% | 25% Failures | 75% Failures |
|---|---|---|---|---|---|
| BL_Eotaxin_H | 451 | 308 | 623 | 308 | 623 |
| BL_Eotaxin_L | 238.5 | 178 | 344 | 160.5 | 449 |
| Combined | 308 | 229 | 451 | 185 | 535 |
Tests Between Groups
| Test | ChiSquare | DF | Prob>ChiSq |
|---|---|---|---|
| Log-Rank | 6.1011 | 1 | 0.0135 * |
| Wilcoxon | 5.8445 | 1 | 0.0156 * |

[Fig. 21a]
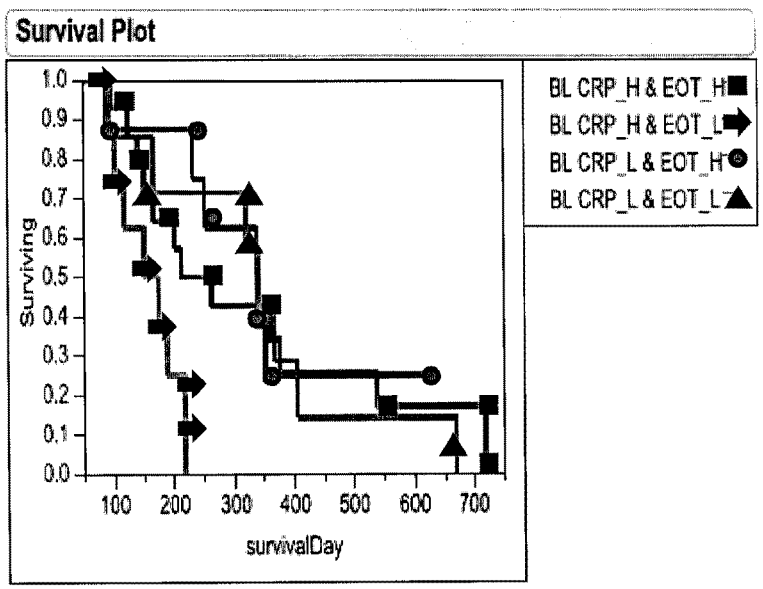
Summary
| Group | Number failed | Number censored | Mean | | Std Error |
|---|---|---|---|---|---|
| BL CRP_H & EOT_H | 12 | 2 | 329 | | 61 |
| BL CRP_H & EOT_L | 8 | 0 | 157 | | 18 |
| BL CRP_L & EOT_H | 6 | 3 | 288 | Biased | 34 |
| BL CRP_L & EOT_L | 7 | 0 | 337 | | 70 |
| Combined | 33 | 5 | 299 | | 32 |
Quantiles
| Group | Median Time | Lower 95% | Upper 95% | 25% Failures | 75% Failures |
|---|---|---|---|---|---|
| BL CRP_H & EOT_H | 237 | 140 | 538 | 150 | 538 |
| BL CRP_H & EOT_L | 162 | 90 | 218 | 110 | 203 |
| BL CRP_L & EOT_H | 337 | 90 | . | 241.5 | . |
| BL CRP_L & EOT_L | 340 | 92 | 405 | 167 | 405 |
| Combined | 232 | 174 | 337 | 150 | 366 |
Tests Between Groups
| Test | ChiSquare | DF | Prob>ChiSq |
|---|---|---|---|
| Log-Rank | 11.4011 | 3 | 0.0097 * |
| Wilcoxon | 9.0258 | 3 | 0.0289 * |

[Fig. 21b]
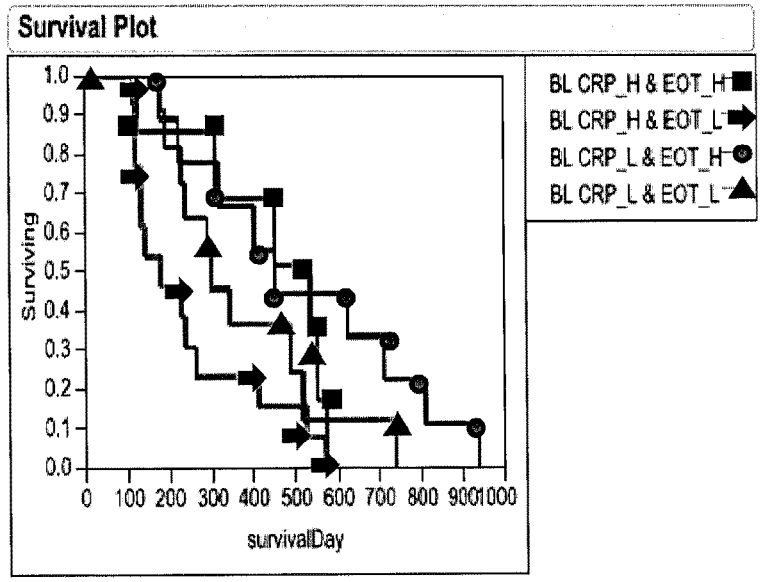
Product-Limit Survival Fit Arm=3
Summary
| Group | Number failed | Number censored | Mean | Std Error |
|---|---|---|---|---|
| BL CRP_H & EOT_H | 6 | 1 | 432 | 66 |
| BL CRP_H & EOT_L | 13 | 1 | 244 | 44 |
| BL CRP_L & EOT_H | 9 | 0 | 516 | 89 |
| BL CRP_L & EOT_L | 10 | 1 | 372 | 58 |
| Combined | 38 | 3 | 376 | 35 |
Quantiles
| Group | Median Time | Lower 95% | Upper 95% | 25% Failures | 75% Failures |
|---|---|---|---|---|---|
| BL CRP_H & EOT_H | 535 | 125 | 573 | 308 | 551 |
| BL CRP_H & EOT_L | 178 | 118 | 262 | 132 | 262 |
| BL CRP_L & EOT_H | 450 | 177 | 808 | 316 | 711 |
| BL CRP_L & EOT_L | 299 | 190 | 517 | 229 | 486 |
| Combined | 308 | 229 | 451 | 185 | 535 |
Tests Between Groups
| Test | ChiSquare | DF | Prob>ChiSq |
|---|---|---|---|
| Log-Rank | 11.0949 | 3 | 0.0112 * |
| Wilcoxon | 11.7697 | 3 | 0.0082 * |

[Fig. 22a]
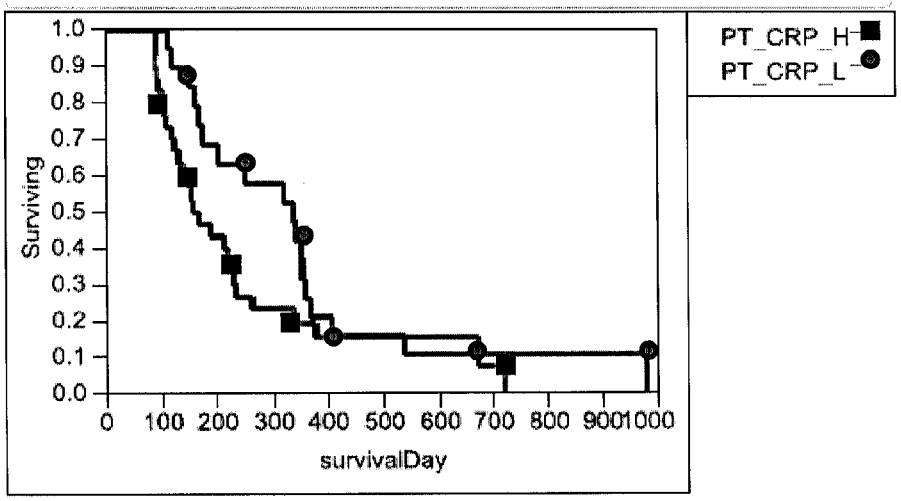
Product-Limit Survival Fit Arm=2
Summary
| Group | Number failed | Number censored | Mean | Std Error |
|---|---|---|---|---|
| PT_CRP_H | 27 | 4 | 252 | 38 |
| PT_CRP_L | 18 | 1 | 350 | 57 |
| Combined | 45 | 5 | 287 | 33 |
Quantiles
| Group | Median Time | Lower 95% | Upper 95% | 25% Failures | 75% Failures |
|---|---|---|---|---|---|
| PT_CRP_H | 162.5 | 124 | 230 | 109 | 262 |
| PT_CRP_L | 337 | 167 | 358 | 167 | 366 |
| Combined | 212 | 158 | 262 | 131 | 352 |
Tests Between Groups
| Test | ChiSquare | DF | Prob>ChiSq |
|---|---|---|---|
| Log-Rank | 2.2731 | 1 | 0.1316 |
| Wilcoxon | 4.6678 | 1 | 0.0307 * |

[Fig. 22b]
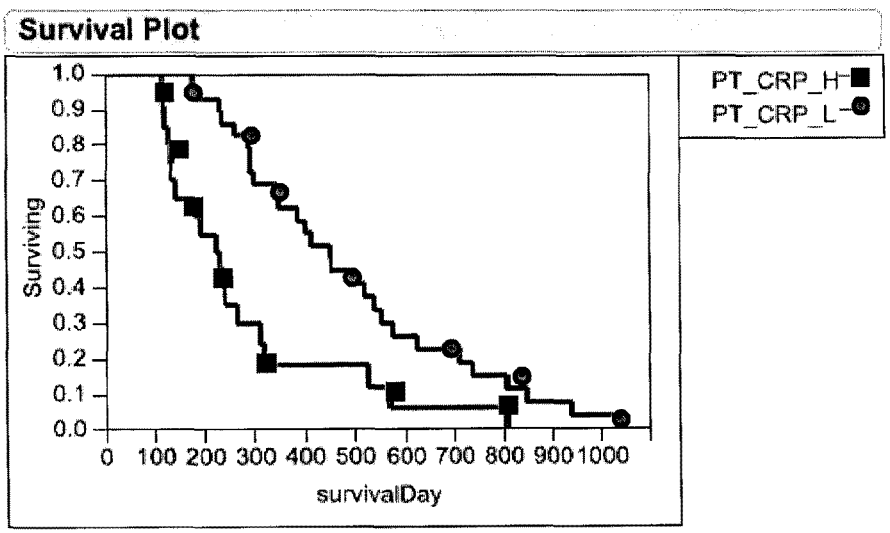

[Fig. 23a]
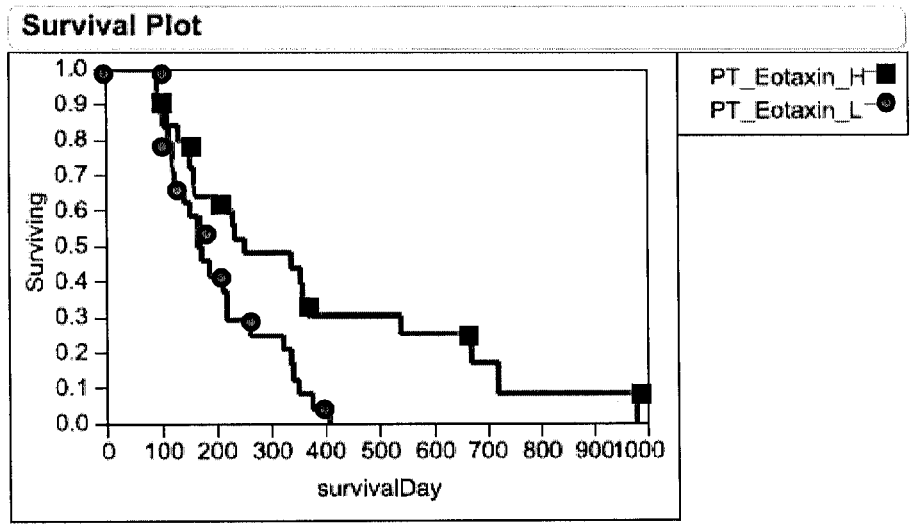

[Fig. 23b]
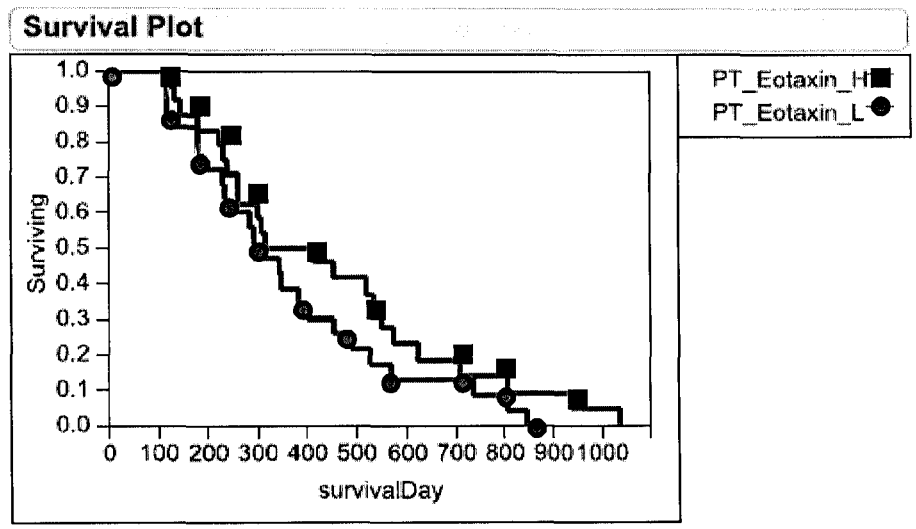
Summary
| Group | Number failed | Number censored | Mean | Std Error |
|---|---|---|---|---|
| PT_Eotaxin_H | 23 | 2 | 440 | 54 |
| PT_Eotaxin_L | 24 | 2 | 359 | 44 |
| Combined | 47 | 4 | 400 | 35 |
Quantiles
| Group | Median Time | Lower 95% | Upper 95% | 25% Failures | 75% Failures |
|---|---|---|---|---|---|
| PT_Eotaxin_H | 364 | 239 | 551 | 234 | 573 |
| PT_Eotaxin_L | 290 | 228 | 401 | 190 | 486 |
| Combined | 316 | 259 | 450 | 228 | 535 |
Tests Between Groups
| Test | ChiSquare | DF | Prob>ChiSq |
|---|---|---|---|
| Log-Rank | 1.5340 | 1 | 0.2155 |
| Wilcoxon | 1.1518 | 1 | 0.2832 |

[Fig. 24a]
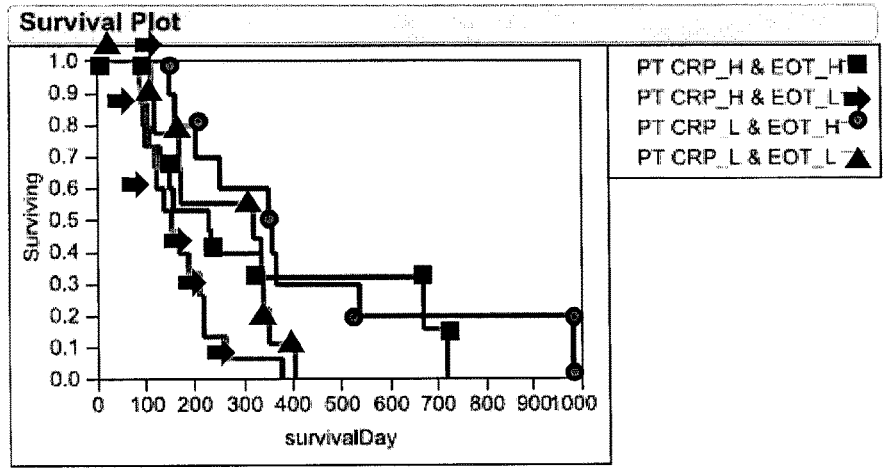
Summary
| Group | Number failed | Number censored | Mean | Std Error |
|---|---|---|---|---|
| PT CRP_H & EOT_H | 12 | 4 | 335 | 70 |
| PT CRP_H & EOT_L | 15 | 0 | 172 | 20 |
| PT CRP_L & EOT_H | 9 | 1 | 434 | 99 |
| PT CRP_L & EOT_L | 9 | 0 | 258 | 38 |
| Combined | 45 | 5 | 287 | 33 |
Quantiles
| Group | Median Time | Lower 95% | Upper 95% | 25% Failures | 75% Failures |
|---|---|---|---|---|---|
| PT CRP_H & EOT_H | 230 | 96 | 670 | 102 | 670 |
| PT CRP_H & EOT_L | 152 | 105 | 212 | 109 | 218 |
| PT CRP_L & EOT_H | 355 | 150 | 538 | 202 | 538 |
| PT CRP_L & EOT_L | 320 | 112 | 349 | 167 | 340 |
| Combined | 212 | 158 | 262 | 131 | 352 |
Tests Between Groups
| Test | ChiSquare | DF | Prob>ChiSq |
|---|---|---|---|
| Log-Rank | 10.3496 | 3 | 0.0158 * |
| Wilcoxon | 8.1352 | 3 | 0.0433 * |

[Fig. 24b]
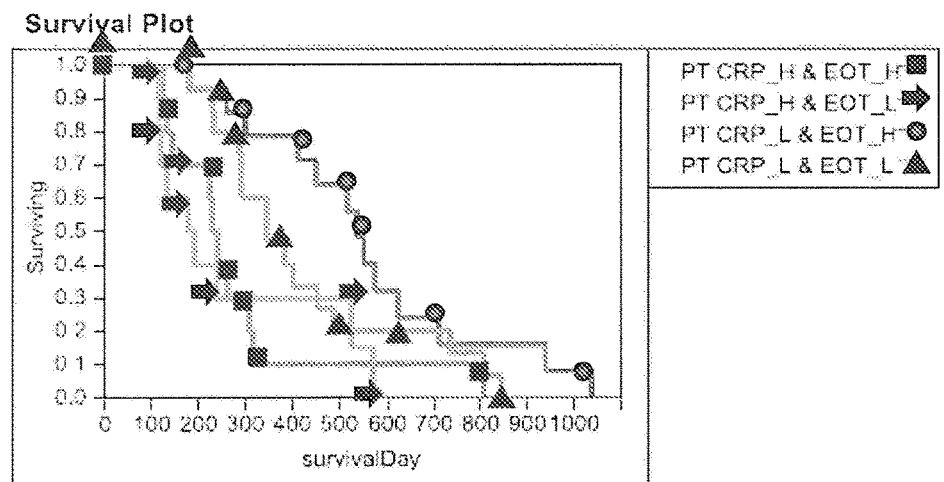
Product-Limit Survival Fit Arm=3
Summary
| Group | Number failed | Number censored | Mean | Std Error |
|---|---|---|---|---|
| PT CRP_H & EOT_H | 10 | 0 | 278 | 63 |
| PT CRP_H & EOT_L | 9 | 1 | 273 | 62 |
| PT CRP_L & EOT_H | 13 | 2 | 555 | 68 |
| PT CRP_L & EOT_L | 15 | 1 | 421 | 65 |
| Combined | 47 | 4 | 400 | 35 |
Quantiles
| Group | Median Time | Lower 95% | Upper 95% | 25% Failures | 75% Failures |
|---|---|---|---|---|---|
| PT CRP_H & EOT_H | 234 | 125 | 308 | 143 | 308 |
| PT CRP_H & EOT_L | 184 | 114 | 525 | 118 | 525 |
| PT CRP_L & EOT_H | 535 | 299 | 623 | 412 | 623 |
| PT CRP_L & EOT_L | 345 | 233 | 451 | 285 | 486 |
| Combined | 316 | 259 | 450 | 228 | 535 |
Tests Between Groups
| Test | ChiSquare | DF | Prob>ChiSq |
|---|---|---|---|
| Log-Rank | 12.2787 | 3 | 0.0065 * |
| Wilcoxon | 16.3031 | 3 | 0.0010 * |

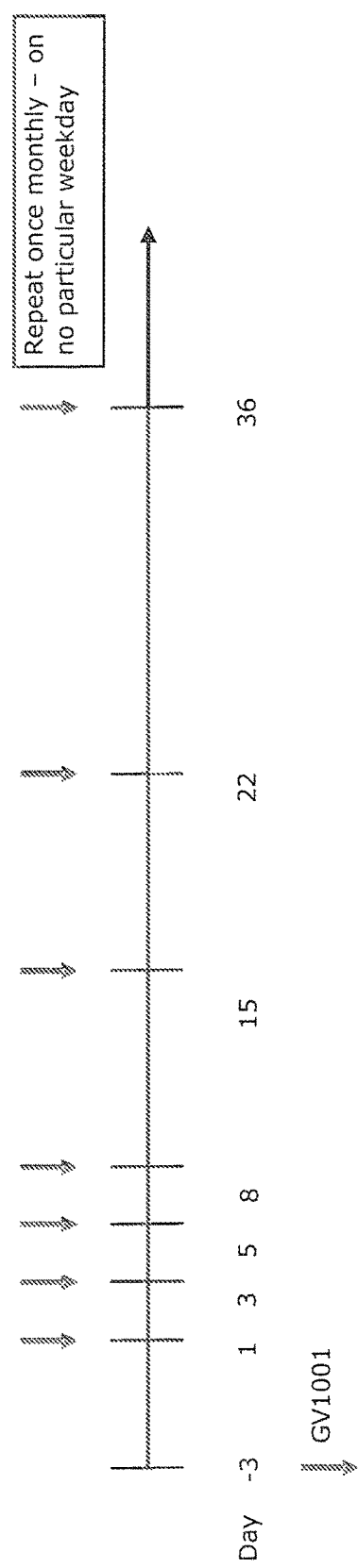
[Fig. 25]

SEQUENCE LISTING

<160> NUMBER OF SEQ ID NOS: 11

<210> SEQ ID NO 1
<211> LENGTH: 16
<212> TYPE: PRT
<213> ORGANISM: Homo sapiens

<400> SEQUENCE: 1

Glu Ala Arg Pro Ala Leu Leu Thr Ser Arg Leu Arg Phe Ile Pro Lys
1               5                   10                  15

<210> SEQ ID NO 2
<211> LENGTH: 97
<212> TYPE: PRT
<213> ORGANISM: Homo sapiens

<400> SEQUENCE: 2

Met Lys Val Ser Ala Ala Leu Leu Trp Leu Leu Leu Ile Ala Ala Ala
1               5                   10                  15

Phe Ser Pro Gln Gly Leu Ala Gly Pro Ala Ser Val Pro Thr Thr Cys
                20                  25                  30

Cys Phe Asn Leu Ala Asn Arg Lys Ile Pro Leu Gln Arg Leu Glu Ser
            35                  40                  45

Tyr Arg Arg Ile Thr Ser Gly Lys Cys Pro Gln Lys Ala Val Ile Phe
        50                  55                  60

Lys Thr Lys Leu Ala Lys Asp Ile Cys Ala Asp Pro Lys Lys Lys Trp
65                  70                  75                  80

Val Gln Asp Ser Met Lys Tyr Leu Asp Gln Lys Ser Pro Thr Pro Lys
                85                  90                  95

Pro

<210> SEQ ID NO 3
<211> LENGTH: 119
<212> TYPE: PRT
<213> ORGANISM: Homo sapiens

<400> SEQUENCE: 3

Met Ala Gly Leu Met Thr Ile Val Thr Ser Leu Leu Phe Leu Gly Val
1               5                   10                  15

Cys Ala His His Ile Ile Pro Thr Gly Ser Val Val Ile Pro Ser Pro
                20                  25                  30

Cys Cys Met Phe Phe Val Ser Lys Arg Ile Pro Glu Asn Arg Val Val
            35                  40                  45

Ser Tyr Gln Leu Ser Ser Arg Ser Thr Cys Leu Lys Ala Gly Val Ile
        50                  55                  60

Phe Thr Thr Lys Lys Gly Gln Gln Phe Cys Gly Asp Pro Lys Gln Glu
65                  70                  75                  80

Trp Val Gln Arg Tyr Met Lys Asn Leu Asp Ala Lys Gln Lys Lys Ala
                85                  90                  95

Ser Pro Arg Ala Arg Ala Val Ala Val Lys Gly Pro Val Gln Arg Tyr
            100                 105                 110

Pro Gly Asn Gln Thr Thr Cys
            115

<210> SEQ ID NO 4
<211> LENGTH: 94
<212> TYPE: PRT
<213> ORGANISM: Homo sapiens

<400> SEQUENCE: 4

Met Met Gly Leu Ser Leu Ala Ser Ala Val Leu Leu Ala Ser Leu Leu
1               5                   10                  15

Ser Leu His Leu Gly Thr Ala Thr Arg Gly Ser Asp Ile Ser Lys Thr
                20                  25                  30

Cys Cys Phe Gln Tyr Ser His Lys Pro Leu Pro Trp Thr Trp Val Arg
            35                  40                  45

Ser Tyr Glu Phe Thr Ser Asn Ser Cys Ser Gln Arg Ala Val Ile Phe
        50                  55                  60

Thr Thr Lys Arg Gly Lys Lys Val Cys Thr His Pro Arg Lys Lys Trp
65                  70                  75                  80

Val Gln Lys Tyr Ile Ser Leu Leu Lys Thr Pro Lys Gln Leu
                85                  90

<210> SEQ ID NO 5
<211> LENGTH: 925
<212> TYPE: DNA
<213> ORGANISM: Homo sapiens

<400> SEQUENCE: 5

```
atgggcaaag gcttccctgg aatctcccac actgtctgct ccctataaaa ggcaggcaga      60
tgggccagag gagcagagag gctgagacca acccagaaac caccacctct cacgccaaag     120
ctcacacctt cagcctccaa catgaaggtc tccgcagcac ttctgtggct gctgctcata     180
gcagctgcct tcagccccca ggggctcgct gggccagctt ctgtcccaac cacctgctgc     240
tttaacctgg ccaataggaa gataccccct cagcgactag agagctacag gagaatcacc     300
agtggcaaat gtccccagaa agctgtgatc ttcaagacca aactggccaa ggatatctgt     360
gccgacccca agaagaagtg ggtgcaggat tccatgaagt atctggacca aaaatctcca     420
actccaaagc cataaataat caccattttt gaaaccaaac cagagcctga gtgttgccta     480
atttgttttc ccttcttaca atgcattctg aggtaacctc attatcagtc caagggcat     540
gggtttatt atatatat atttttttt ttaaaaaaa aacgtattgc atttaattta     600
```

```
ttgaggcttt aaaacttatc ctccatgaat atcagttatt tttaaactgt aaagctttgt    660
gcagattctt tacccctgg  gagccccaat tcgatcccct gtcacgtgtg ggcaatgttc    720
cccctctcct ctcttcctcc ctggaatctt gtaaaggtcc tggcaaagat gatcagtatg    780
aaaatgtcat tgttcttgtg aacccaaagt gtgactcatt aaatggaagt aaatgttgtt    840
ttaggaatac ataaagtatg tgcatatttt attatagtca ctagttgtaa ttttttttgtg   900 ggaaatccac actgagctga ggggg                                          925

<210> SEQ ID NO 6
<211> LENGTH: 360
<212> TYPE: DNA
<213> ORGANISM: Homo sapiens

<400> SEQUENCE: 6
atggcaggcc tgatgaccat agtaaccagc cttctgttcc ttggtgtctg tgcccaccac     60
atcatcccta cgggctctgt ggtcatcccc tctccctgct gcatgttctt tgtttccaag    120
agaattcctg agaaccgagt ggtcagctac cagctgtcca gcaggagcac atgcctcaag    180
gcaggagtga tcttcaccac caagaagggc cagcagttct gtggcgaccc caagcaggag    240
tgggtccaga ggtacatgaa gaacctggac gccaagcaga gaaggcttc ccctagggcc     300 agggcagtgg ctgtcaaggg ccctgtccag agatatcctg caaccaaac cacctgctaa    360

<210> SEQ ID NO 7
<211> LENGTH: 562
<212> TYPE: DNA
<213> ORGANISM: Homo sapiens

<400> SEQUENCE: 7
ctggaattga ggctgagcca aagaccccag ggccgtctca gtctcataaa agggggatcag    60 gcaggaggag tttgggagaa acctgagaag ggcctgattt gcagcatcat gatgggcctc   120
tccttggcct ctgctgtgct cctggcctcc ctcctgagtc tccaccttgg aactgccaca   180
cgtgggagtg acatatccaa gacctgctgc ttccaataca gccacaagcc ccttccctgg   240
acctgggtgc gaagctatga attccaccagt aacagctgct cccagcgggc tgtgatattc   300
actaccaaaa gaggcaagaa agtctgtacc catccaagga aaaatgggt gcaaaaatac    360 atttctttac tgaaaactcc gaaacaattg tgactcagct gaattttcat ccgaggacgc    420
ttggaccccg ctcttggctc tgcagccctc tggggagcct gcggaatctt ttctgaaggc    480
tacatggacc cgctggggag agagggtgt ttcctcccag agttacttta ataaaggttg    540
ttcatagagt tgacttgttc at                                             562

<210> SEQ ID NO 8
<211> LENGTH: 102
<212> TYPE: PRT
<213> ORGANISM: Homo sapiens

<400> SEQUENCE: 8

Met Glu Lys Leu Leu Cys Phe Leu Val Leu Thr Ser Leu Ser His Ala
1               5                   10                  15

Phe Gly Gln Thr Asp Met Ser Arg Lys Ala Phe Val Phe Pro Lys Glu
            20                  25                  30

Ser Asp Thr Ser Tyr Val Ser Leu Lys Ala Pro Leu Thr Lys Pro Leu
        35                  40                  45

Lys Ala Phe Thr Val Cys Leu His Phe Tyr Thr Glu Leu Ser Ser Thr
    50                  55                  60
```

```
His Glu Ile Asn Thr Ile Tyr Leu Gly Gly Pro Phe Ser Pro Asn Val
 65                  70                  75                  80

Leu Asn Trp Arg Ala Leu Lys Tyr Glu Val Gln Gly Glu Val Phe Thr
                 85                  90                  95

Lys Pro Gln Leu Trp Pro
            100
```

<210> SEQ ID NO 9
<211> LENGTH: 1018
<212> TYPE: DNA
<213> ORGANISM: Homo sapiens

<400> SEQUENCE: 9

```
aaggcaagag atctaggact tctagcccct gaactttcag ccgaatacat cttttccaaa      60
ggagtgaatt caggcccttg tatcactggc agcaggacgt gaccatggag aagctgttgt     120
gtttcttggt cttgaccagc ctctctcatg cttttggcca gacagacatg tcgaggaagg     180
cttttgtgtt tcccaaagag tcggatactt cctatgtatc cctcaaagca ccgttaacga     240
agcctctcaa agccttcact gtgtgcctcc acttctacac ggaactgtcc tcgacccgtg     300
ggtacagtat tttctcgtat gccaccaaga gacaagacaa tgagattctc atattttggt     360
ctaaggatat aggatacagt tttacagtgg gtgggtctga atattattc gaggttcctg      420
aagtcacagt agctccagta cacatttgta caagctggga gtccgcctca gggatcgtgg     480
agttctgggt agatgggaag cccagggtga ggaagagtct gaagaaggga tacactgtgg     540
gggcagaagc aagcatcatc ttggggcagg agcaggattc cttcggtggg aactttgaag     600
gaagccagtc cctggtggga gacattggaa atgtgaacat gtgggacttt gtgctgtcac     660
cagatgagat taacaccatc tatcttggcg ggcccttcag tcctaatgtc ctgaactggc     720
gggcactgaa gtatgaagtg caaggcgaag tgttcaccaa accccagctg tggccctgag     780
gcccagctgt gggtcctgaa ggtacctccc ggttttttac accgcatggg ccccacgtct     840
ctgtctctgg tacctcccgc ttttttacac tgcatggttc ccacgtctct gtctctgggc     900
ctttgttccc ctatatgcat tgcaggcctg ctccaccctc ctcagcgcct gagaatggag     960
gtaaagtgtc tggtctggga gctcgttaac tatgctggga aacggtccaa aagaatca      1018
```

<210> SEQ ID NO 10
<211> LENGTH: 92
<212> TYPE: PRT
<213> ORGANISM: Homo sapiens

<400> SEQUENCE: 10

```
Met Gln Val Ser Thr Ala Ala Leu Ala Val Leu Leu Cys Thr Met Ala
  1               5                  10                  15

Leu Cys Asn Gln Phe Ser Ala Ser Leu Ala Ala Asp Thr Pro Thr Ala
                 20                  25                  30

Cys Cys Phe Ser Tyr Thr Ser Arg Gln Ile Pro Gln Asn Phe Ile Ala
             35                  40                  45

Asp Tyr Phe Glu Thr Ser Ser Gln Cys Ser Lys Pro Gly Val Ile Phe
 50                  55                  60

Leu Thr Lys Arg Ser Arg Gln Val Cys Ala Asp Pro Ser Glu Glu Trp
 65                  70                  75                  80

Val Gln Lys Tyr Val Ser Asp Leu Glu Leu Ser Ala
                 85                  90
```

```
<210> SEQ ID NO 11
<211> LENGTH: 813
<212> TYPE: DNA
<213> ORGANISM: Homo sapiens

<400> SEQUENCE: 11
agctggtttc agacttcaga aggacacggg cagcagacag tggtcagtcc tttcttggct      60
ctgctgacac tcgagcccac attccgtcac ctgctcagaa tcatgcaggt ctccactgct     120
gcccttgctg tcctcctctg caccatggct ctctgcaacc agttctctgc atcacttgct     180
gctgacacgc cgaccgcctg ctgcttcagc tacacctccc ggcagattcc acagaatttc     240
atagctgact actttgagac gagcagccag tgctccaagc ccggtgtcat cttcctaacc     300
aagcgaagcc ggcaggtctg tgctgacccc agtgaggagt gggtccagaa atatgtcagc     360
gacctggagc tgagtgcctg aggggtccag aagcttcgag gcccagcgac ctcggtgggc     420
ccagtgggga ggagcaggag cctgagcctt gggaacatgc gtgtgacctc cacagctacc     480
tcttctatgg actggttgtt gccaaacagc cacactgtgg gactcttctt aacttaaatt     540
ttaatttatt tatactattt agttttgta atttattttc gatttcacag tgtgtttgtg      600
attgtttgct ctgagagttc ccctgtcccc tccccttcc ctcacaccgc gtctggtgac      660
aaccgagtgg ctgtcatcag cctgtgtagg cagtcatggc accaaagcca ccagactgac     720
aaatgtgtat cggatgcttt tgttcagggc tgtgatcggc ctggggaaat aataaagatg     780
ctcttttaaa aggtaaaaaa aaaaaaaaaa aaa                                  813
```

BIOLOGICAL MARKERS USEFUL IN CANCER IMMUNOTHERAPY

REFERENCE TO SEQUENCE LISTING SUBMITTED ELECTRONICALLY VIA EFS-WEB

The content of the electronically submitted sequence listing (Name: 2473_0850002_SegListing_ST25.txt; 10,405 bytes; and Date of Creation: Nov. 16, 2015) was originally submitted in the International Application No. PCT/KR2014/005031 and is incorporated herein by reference in its entirety.

TECHNICAL FIELD

The present invention relates to the field of cancer immunotherapy and the field of anti-inflammatory drugs. In particular the present invention relates to methods and kits for use in therapy, where the diagnostic/predictive value of eotaxin and C-reactive protein are exploited.

BACKGROUND ART

The 16-mer peptide EARPALLTSRLRFIPK (SEQ ID NO: 1; also termed "GV1001") is a fragment of the human telomerase enzyme (WO 00/02581). GV1001 binds multiple HLA class II molecules and harbours putative HLA class I epitopes. The peptide has therefore been considered capable of eliciting combined CD4/CD8 T-cell responses, which in turn are important for initiation of tumour eradication and long-term memory. Clinical trials in advanced pancreatic and pulmonary cancer patients have demonstrated GV1001-specific T-cell responses in >50% of subjects, without clinically important toxicity (Kyte JA (2009), Expert Opin Investig Drugs 18 (5):687-94.

An on-line publication on chronic inflammation by the Life Extension foundation (www.lef.org; accessed 6 Jun. 2013), focused on the long-term health effects of chronic, low-level inflammation, reviewed various markers and mediators of inflammation, among which tumour necrosis factor alpha (TNFα), nuclear factor kappa-B(NF-κB), interleukins, C-reactive protein (CRP), eicosanoids, cyclooxygenases (COX) and lipooxygenases (LOX) and various other inciting factors.

Guo et al. (J Immunol 2001; 166:5208-5218) found that eotaxin mRNA and protein were upregulated during an inflammatory response in a rat model of acute inflammatory injury, and explored its role in neutrophile recruitment.

Eotaxin-1, -2 and -3 (also known as CCL11, CCL24 and CCL26) are known chemokines known to recruit eosinophils and other leukocytes, and elicit their effects by binding to the cell surface chemokine receptors (e.g., CCR3).

DISCLOSURE OF INVENTION

Technical Problem

It is an object of embodiments of the invention to provide improved methods for predicting efficacy of medical treatment with GV1001-derived drugs as well as for predicting patient survival among individuals suffering from cancer, in particular pancreatic cancer.

Solution to Problem

TeloVac, a multi-centre Phase III trial of a GV1001 based vaccine in advanced and metastatic pancreatic cancer has recently been conducted through the Cancer Research UK Liverpool Clinical Trials Unit and supported by the GemVax AS, a subsidiary of KAEL-GemVax.

The trial recruited 1062 patients in 52 centres throughout the United Kingdom. While there was no significant difference in overall survival between the groups that received the vaccine and the control group receiving chemotherapy, the trial however also included an ambitious program of translational research. Initial results indicate that the vaccine resulted in a significant anti-inflammatory response that correlates well with new research being conducted by the parent company, Kael-GemVax. Additionally, 3 possible biomarkers—eotaxin, MIP1α, and CRP—were identified in a subgroup of patients as indicators of an increased survival.

Advantageous Effects of Invention

So, in its broadest aspects, the invention relates to the use of eotaxin and/or MIP1α and/or CRP as prognostic tools useful in therapeutic treatment with GV1001-derived material.

BRIEF DESCRIPTION OF DRAWINGS

FIG. 1: Graphs showing levels of IL-4, IL-5, IL-7, IL-17, PDGF and VEGF in serum form baseline arm 2 and 3, arm 2 week 7 and arm 3 week 10 patients (p values uncorrected Kruskal-Wallis).

FIG. 2: Graphs showing the change in levels of IFNγ, IL-10, IL-7, PDGF, RANTES, TNFα and VEGF for arms 2 and 3. Also shown are the numbers of positive (+ve) and negative (−ve) changes along with p values.

FIG. 3: Levels of CRP in arm 2 and 3 patients at baseline and following treatment.

FIG. 4: Paired analysis of CRP in arm 2 patients (left) and 3 patients (right) at baseline and following treatment Also shown are the numbers of positive (+ve) and negative (−ve) changes along with p values.

FIG. 5: Survival curves for IL-8 dichotomised at the median for baseline levels, post treatment levels and absolute change form baseline to post treatment.

FIG. 6: Survival curves for Eotaxin dichotomised at the median for baseline levels, post treatment levels and absolute change form baseline to post treatment.

FIG. 7: Survival curves for MIP1α dichotomised at the median for baseline levels, post treatment levels and absolute change form baseline to post treatment.

FIG. 8: Survival curves for MIP1β dichotomised at the median for baseline levels, post treatment levels and absolute change form baseline to post treatment.

FIG. 9: Survival curves for VEGF dichotomised at the median for baseline levels, post treatment levels and absolute change form baseline to post treatment.

FIG. 10: Survival curves for CRP dichotomised at the median for baseline levels, post treatment levels and absolute change form baseline to post treatment.

FIG. 11. Survival curves for CRP dichotomised at the median for post treatment levels in arm 3.

FIG. 12: (A) Survival curves for eotaxin (high: median survival 493 days, n=16; low:median survival 239 days, n=25). (B) Survival curves for CRP (high: median survival 222 days, n=20; low: median survival 486 days, n=21).

FIG. 13 shows profile plots of baseline and post-treatment means of log cytokine data from serum for Arm 2. BL and PT represent baseline and post treatment, respectively.

FIG. 14 shows baseline and post treatment means of log cytokine data from serum for Arm 3.

FIG. 15 shows a profile plot of the mean differences (post-treatment−baseline) for the cytokines in serum for each arm. Of note, 19 cytokines showed a statistically significant decrease between baseline and post-treatment in Arm 2 (PDGF, IL1β, IL-1ra, IL-2, IL-4, IL-5, IL-7, IL-10, IL-12, IL-13, IL-17, GCSF, IFNγ, eotaxin, FGFb, MIP1β, RANTES, TNFα, VEGF; but not CRP, IL-6, IL-8, IL-9, IL-15, GM-CSF, IP10, MCP1, MIP1α) and none in Arm3.

FIG. 16 shows the p-values obtained from a Wilcoxon signed-rank test used on each cytokine form serum for each arm to test for increase/decrease in values from baseline to post treatment. The significant differences (p<0.05) as seen are in bold grey font. The decreases were larger in Arm2 than in Arm3, noting that there were 19 significant decreases in Arm2 but none in Arm3.

FIG. 17 shows the median difference of post-treatment minus baseline levels, for each cytokine in serum, for each arm of the study. Decreases are highlighted in light shadow and increases/no change are highlighted in dark shadow.

FIG. 18 shows Cox proportional hazards models on baseline data for each cytokine in serum for each arm of the study. The table gives univariate analyses for the baseline data and shows hazard ratios with 95% confidence intervals and p-values. CRP, IL-1ra, IL-2, IL-10, Eotaxin and IFNγ are significant (p<0.1) for Arm 2, while CRP, IL-1ra and Eotaxin are significant for Arm 3.

FIG. 19a and FIG. 19b show levels of CRP at baseline in Arm 2 and Arm 3. Low levels of CRP gave a median survival of 337 days for Arm 2 and a median survival of 373 days for Arm 3. Baseline CRP levels predicted median (95% CI) overall survival in Arm3 (high CRP=250 [132-451] days; low CRP=372.5 [229-517] days; p=0.0500) but not in Arm2 (high CRP=195 [140-262] days; low CRP=337 [167-366] days; p=0.2534)

FIG. 20a and FIG. 20b show levels of Eotaxin at baseline in Arm 2 and Arm 3. High levels of Eotaxin in serum give a median survival of 300 days for Arm 2 and a median survival of 451 days for Arm 3. Baseline eotaxin levels predicted median (95% CI) overall survival in Arm3 (high eotaxin=451 [308-623] days; low eotaxin=238.5 [178-344] days; p=0.0135) but not in Arm2 (high eotaxin=299.5 [167-358] days; low eotaxin=188 [102-320] days; p=0.1138)

FIG. 21a and FIG. 21b show Proportional hazards models using dichotomized variables for the baseline data for CRP and Eotaxin in serum combined. When variables were combined at baseline the longest overall survival was predicted by a combination of low levels of CRP plus high levels of Eotaxin in Arm 2 (median survival=337 days) and similarly for Arm 3 (median survival=450 days).

FIG. 22a and FIG. 22b show CRP in serum post treatment in Arm 2 and Arm 3. Low levels of CRP give a median survival of 337 days for Arm 2 and a median survival of 450 days for Arm 3.

FIG. 23a and FIG. 23b show Eotaxin in serum post treatment in Arm 2 and Arm 3. High levels of Eotaxin give a median survival of 251 days for Arm 2 and a median survival of 364 days for Arm 3.

FIGS. 24a and 24b show Proportional hazards models using dichotomized variables for the post-treatment data for serum CRP and serum Eotaxin combined. When variables were combined the longest survival was predicted by a combination of low levels of CRP plus high levels of Eotaxin in Arm 2 (median survival=355 days) and similarly for Arm 3 (median survival=535 days). When variables were combined at post-treatment the longest survival was predicted by a combination of low levels of CRP plus high levels of Eotaxin in Arm 2 (median survival=355 days) and similarly for Arm 3 (median survival=535 days).

FIG. 25 shows the vaccination schedule employed in the Examples.

BEST MODE FOR CARRYING OUT THE INVENTION

Definitions

"GV1001" denotes the telomerase-derived peptide having SEQ ID NO: 1: EARPALLTSRLRFIPK "Eotaxin" denotes the protein having any one of the amino acid sequences SEQ ID NO: 2-4 (or allelic or naturally occurring isoforms or variants thereof), which can be encoded by any one of the nucleic acid sequences SEQ ID NO: 5-7, respectively.

"CRP" is the protein having the amino acid sequence SEQ ID NO: 8 (or allelic or other naturally occurring isoforms or variants thereof), which can be encoded by the nucleic acid sequence SEQ ID NO: 9.

"MIP1α" is the protein having the amino acid sequence SEQ ID NO: 10 (or allelic or other naturally occurring isoforms or variants thereof), which can be encoded by the nucleic acid sequence SEQ ID NO: 11.

Specific Embodiments of the Invention

In one embodiment, the present invention provides a method for anti-cancer and/or anti-inflammatory treatment of an individual in need thereof by administering a therapeutically effective amount of a polypeptide, which comprises SEQ ID NO: 1 or comprises a fragment of SEQ ID NO: 1 of at least 8 amino acids (such as 8, 9, 10, 11, 12, 13, 14 or 15 amino acids), if said individual exhibits an increased serum level of eotaxin and/or MIP1α when compared to population average or to a population of individuals suffering from the same cancer and/or inflammatory condition.

A related embodiment relates to a method for determining whether to instigate anti-cancer and/or anti-inflammatory treatment of an individual in need thereof, wherein said anti-cancer treatment and/or anti-inflammatory treatment involves administration of a polypeptide, which comprises SEQ ID NO: 1 or comprises a fragment of SEQ ID NO: 1 of at least 8 amino acids, comprising determining if said individual exhibits an increased serum level of eotaxin and/or MIP1α when comparing to the population average or to a population of individuals suffering from the same cancer and/or inflammatory condition, a positive determination indicating that said treatment is justified.

As appears from the examples, it has been found by the present inventors that median survival of cancer patients receiving the medical treatments disclosed herein is at its highest when these patients exhibit a combined baseline serum level of high eotaxin and low CRP. Further, it is also found that patients that exhibit the same combination (high eotaxin, low CRP) post-treatment art those that have the highest median survival.

Hence according to the present invention, the treatments of the present invention are preferably those where the patients subjected to the treatments are those who prior to treatment exhibit increased eotaxin and/or MIP-1α serum levels in combination with decreased CRP levels—again the levels are determined either relative to the average (or median) in the general population or relative to the average or median in the relevant patient group.

Depending on the exact route of administration, the effective amount administered according to the various embodiments of the invention may vary. If the polypeptide is administered as a vaccine, the amounts typically range from 0.5 µg up to 500 mg, with preferred administration amounts ranging between 10 µg to 1000 µg, and in particular between 20 and 200 µg. These ranges are also relevant when the polypeptide is administered as an anti-inflammatory agent, but it may be relevant—for instance if the polypepide is administered intraveneously or intraarterially—to regulate the amounts administered on the basis of the individual's condition, body weight and age.

Increased levels of eotaxin and/or MIP1α and/or CRP are in the relevant embodiments determined according to standardized assays generally known in the art-immune assays, for instance ELISAs, are preferred, but also assays that determine the activity of these cytokines on suitable target cells or suitable target molecules are relevant. If an assay is very sensitive and accurate, even small increases compared to standard values may be relevant, whereas less sensitive or accurate assays will require that larger deviations from standard values can be determined. As a rule, for a given assay for a particular cytokine there will exist a range of normal values and if the cytokine level is beyond these normal values, the level of eotaxin or MIP1α will be considered to be increased. Typically, the increased baseline level of eotaxin and/or MIP1α is at least 10%, but higher increases in values may be relevant: at least 15%, at least 20%, at least 30%, at least 40%, at least 50%, at least 60%, at least 70%, at least 80%, and even at least 100%.

Another embodiment of the invention relates to a method for anti-cancer and/or anti-inflammatory treatment of an individual in need thereof by administering a therapeutically effective amount of a polypeptide, which comprises SEQ ID NO: 1 or comprises a fragment of SEQ ID NO: 1 of at least 8 amino acids, wherein said treatment is continued after an initial stage of said treatment if said individual exhibits a decrease of CRP level in serum after said initial stage of said treatment. This is to mean, that the treatment has been instigated, but subsequently the measurement of CRP is used to gauge the efficacy of the treatment regimen. If serum CRP does not decrease or increases (cf. the remarks concerning assay sensitivity above), the findings of the present invention questions whether continued treatment with the GV1001-derived polypeptide is of value to the patient, meaning that it can be considered to terminate this part of the treatment and turn to possible alternatives or palliative treatment.

Related to this embodiment is a method for determining the efficacy of therapeutic treatment of an individual with a polypeptide, which comprises SEQ ID NO: 1 or comprises a fragment of SEQ ID NO: 1 of at least 8 amino acids, comprising determining the serum level of CRP in said individual after an initial stage of said treatment and comparing with the serum level of CRP prior to said initial stage of treatment, where a decrease in said serum level indicates that said treatment is effective in terms of conferring an increase in survival time.

Said decrease in the serum level of CRP should typically be at least 10%, but further decreases in values may be relevant: at least 15%, at least 20%, at least 30%, at least 40%, at least 50%, at least 60%, at least 70%, and even at least 80%.

The above-described embodiments have focussed on the use of the GV1001-derived polypeptide, but in important embodiments of the invention, the anti-cancer and/or anti-inflammatory treatment involves concurrent treatment with at least one cytostatic or cytotoxic agent. For instance, the concurrent treatment may involve administration of Gem-Cap as in the present examples, but depending on the cancer or inflammatory disease in question, the GV1001-derived peptide may according to the present invention be combined with the administration of cytostatic/cytotoxic agents particular relevant for the treatment of the disease in question.

Very important embodiments of the invention are those where the treatment is an anti-cancer treatment, and particularly preferred is treatment of pancreatic cancer. However, treatment of other cancer forms are contemplated, and the cancer may be selected from the group consisting of an epithelial cancer, a non-epithelial cancer, and a mixed cancer. The epithelial cancer may be both a carcinoma or an adenocarcinoma, and the non-epithelial or mixed cancer is typically a liposarcoma, a fibrosarcoma, a chondrosarcoma, an osteosarcoma, a leiomyosarcoma, a rhabomyosarcoma, a glioma, a neuroblastoma, a medullablastoma, a malignant melanoma, a malignant meningioma, a neurofibrosarcoma, a leukemia, a myeloproleferative disorder, a lymphoma, a he-mangiosarcoma, a Kaposi's sarcoma, a malignant teratoma, a dysgerminoma, a seminoma, or a choriosarcoma.

Also, the anatomic location of the cancer can be anywhere in body. So the cancer may be a of the eye, the nose, the mouth, the tongue, the pharynx, the oesophagus, the stomach, the colon, the rectum, the bladder, the ureter, the urethra, the kidney, the liver, the pancreas, the thyroid gland, the adrenal gland, the breast, the skin, the central nervous system, the peripheral nervous system, the meninges, the vascular system, the testes, the ovaries, the uterus, the uterine cervix, the spleen, bone, or cartilage The polypeptide is administered typically parenterally, and when administered as a vaccine, the polypeptide will be normally be administered subcutaneously or intradermally. If the anti-inflammatory effect is most desired, also the intraveneous or intraarterial routes may be utilised.

Determination of serum levels of the above mentioned is performed in vitro. Typically, a serum sample is subjected to an ELISA in order to determine the amount of the serum levels of the cytokines.

In all of the above discussed embodiments, the polypeptide can preferably be SEQ ID NO: 1 (i.e. the 16-mer peptide as such) or a fragment of at least 8 amino acids of SEQ ID NO: 1; that is, it is contemplated that it will not be necessary to include further amino acids in the GV1001-derived peptides.

In general embodiments are provided the use of eotaxin and/or MIP1α and/or CRP as a prognostic marker in anti-cancer and/or anti-inflammatory treatment, in particular if said treatment involves administration of a polypeptide, which comprises SEQ ID NO: 1 or comprises a fragment of SEQ ID NO: 1 of at least 8 amino acids. As mentioned above, the typical use will be as an agent captured/determined in an appropriate assay, so this aspect of the invention also covers use of antibodies and other agents that specifically bind to any one of the three cytokines.

An interesting embodiment relates to a method for modulation of the activity of eotaxin and/or MIP1α and/or CRP in an individual in need thereof, said method comprising administering a therapeutically effective amount of a polypeptide as defined herein—such a method will be able to address the negative impact caused by abnormal levels of these cytokines in an individual. Consequently, this embodiment relates to the use of these polypeptides as modulators of eotaxin and/or MIP1α and/or CRP.

Finally, a separate embodiment of the invention relates to a kit comprising a) a pharmaceutical composition comprising a GV1001-derived polypeptide discussed above, and b) means for determining the serum concentration of eotaxin and/or means for determining the serum concentration of MIP1α and/or means for determining the serum concentration of CRP. These means may e.g. be in the form of a suitable immune assay.

MODE FOR THE INVENTION

Example

The TeloVac trial recruited 1062 patients in 52 centres throughout the UK. There was no significant difference in overall survival between the groups that received the vaccine and the control group receiving chemotherapy (Gem-Cap therapy, cf. below), but included an ambitious program of translational research, which is still undergoing evaluation. However, results show that the vaccine resulted in a significant anti-inflammatory response, and that simultaneous vaccination with chemotherapy provides an effective method for generating both an immune response and also promoting an anti-inflammatory effect. Importantly, biomarkers for an increased survival in response to the vaccine were identified in a subgroup of patients.

Materials and Methods

The TeloVac trial, was initiated in January 2007 comparing combination therapy with Gemcitabine and Capecitabine (GemCap) therapy with concurrent and sequential chemo-immunotherapy using GV1001 in locally advanced and metastatic pancreatic cancer.

Vaccination Schedule

FIG. 25 shows the vaccination schedule employed: GV1001 intradermal injections were given three times (preferably Monday, Wednesday and Friday) in the first week (week 1), and once a week in weeks 2, 3, 4, and 6. After this, GV1001 was administered once monthly. GM-CSF was administered separately as an intradermal injection 10-15 minutes before all GV1001 injections at the approximately same site.

Patients with advanced pancreatic cancer have a short life expectancy and their immune system deteriorates rapidly. The window available for induction of immune response is hence limited. It is therefore important to use a frequent vaccination regimen in order to induce an efficient immune response as fast as possible. The vaccination regimen used for GV1001, with aggressive vaccination during the first six weeks of the treatment, was based on a similar regimen used for another peptide vaccine which has proven to be efficient for induction of immune response in patients with advanced pancreatic cancer.

Inflammatory Cytokine Analysis

Serum samples (Arm3 only) from week1 (baseline) and week10 (Gemcitabine+Capecitabine+GV1001) were analyzed by Luminex multiplex cytokine analysis. A total of 26 cytokines were analyzed, and the CRP level was analyzed by ELISA.

Overview of Samples Analysed:

|  | Arm 1 | Arm 2 | Arm 3 |
|---|---|---|---|
| Screening | Baseline Plasma Urine 30 ml | Baseline Plasma Urine 30 ml | Baseline Plasma Urine 30 ml |
| Week 1 | — | Baseline Serum | Baseline Serum |
| Week 7 | — | GemCap Serum | |
| Week 10 | — | | GemCap & GV1001Serum |
| Week 14 | GemCap Plasma Urine 30 ml | GV1001 (+GemCap if progressed)Plasma Urine 30 ml | GemCap & GV1001 Serum Plasma Urine 30 ml |
| Week 18 | — | GV1001 (+GemCap if progressed)Serum | GemCap & GV1001 Serum |
| Week 22 | — | GV1001 (+GemCap if progressed)Serum | |
| Week 26 | GemCap Plasma Urine 30 ml | GV1001 (+GemCap if progressed)Serum | GemCap & GV1001 Plasma Urine 30 ml |

Underlined: Plasma analyzed
Italic letters: Serum analyzed

Grey shading: Plasma analysed
Italic letters: Serum analysed
Arm 1: patients received GemCap only, i.e. a currently accepted standard chemotherapeutic treatment regimen for pancreatic cancer patients utilising a combination of Gemcitabine (administered iv weekly) and Capecitabine (administered as tablets twice daily). Arm 2: patients received GemCap therapy followed by gv1001 at week 7. Arm 3: patients received concurrent GemCap and GV1001 during the entire treatment period.

Cytokines
Grouping of some of the cytokines tested for:
Factors associated with immune stimulatory functions
INF-γ Immune stimulatory
IL-12 (p70) Immune stimulatory
IL-1β Immune stimulatory
IL-6 Immune stimulatory
TNF-α Immune stimulatory
Factors associated with immune suppressive functions:
IL-10 Immune suppressive
IL-1Ra Immune suppressive
IL-4 Immune suppressive
VEGF Immune suppressive
Factors associated with chemotactic functions:
Eotaxin Chemotactic
IL-8 Chemotactic
IP-10 Chemotactic
MCP-1 Chemotactic
MIP-1α Chemotactic
MIP-1β Chemotactic
RANTES Chemotactic
Factors associated with vascular remodelling functions:

FGF basic Vascular remodelling
PDGF-BB Vascular remodelling
VEGF Vascular remodelling
Analysis of Patient Sera Cytokine Results: The Kruskal-Wallis comparison of Arm 2 and Arm 3 baseline (i.e. before treatment) with arm 2 week 7 (GemCap) with Arm 3 week 10 (GemCap and GV1001) serum samples are shown in table 1 below. Kruskal-Wallis testing identifies 18 cytokines with significantly different levels; following Bonferroni-Holm correction, 8 of these cytokines are still significant.

Results

The results are shown in Tables 1-6 and FIGS. 1-24.

There were 7 cytokines (IL-4, IL-5, IL-7, IL-17, PDGF, VEGF and RANTES) that were at significantly higher levels after treatment with GV1001/GemCap compared to GemCap treatment alone. Using crude uncorrected 2-tailed Mann-Whitney PDGF ($p<0.0001$) and RANTES ($p=0.002$) were most significant. Following Bonferroni Holm correction both of these remained significant (Table 2 and FIG. 1).

GemCap treatment resulted in decreased levels of a number of cytokines (pre-treatment compared to post treatment) in the serum fraction of blood (but not in plasma); this decrease was not evident in the presence of GV1001 (Table 3 and FIG. 2).

C-Reactive Protein levels were significantly lower in serum from patients receiving GV1001/GemCap compared to patients receiving GemCap alone (see FIG. 3). There was no significant difference in CRP from baseline (before treatment) to post GemCap (n=38) or from baseline (before treatment) to post GemCap with GV1001 (n=41) (FIG. 4).

Initial crude survival analysis of CRP levels showed that prior to treatment [at baseline] there was no evidence to show an association between overall survival and CRP levels (cut off 6 mg/l) in either arm 2 or arm 3. Further, after treatment in arm 2 there was no association between overall survival and CRP levels (cut off 9 mg/ml). In contrast, after treatment in arm 3, a low CRP was associated with higher overall survival and median survival (486 days) compared to patients with a high CRP (median 222 days; $p=0.0002$) (FIG. 11). Without being bound to theory, patients responding to the vaccine with reduction of CRP appear to have significantly longer survival times than those that do not.

High baseline levels of eotaxin or MIP1α were associated with greatly increased survival in arm 3 (FIGS. 6 and 7). As with CRP post initial treatment this will need to be confirmed by minimizing potential biases from other prognostic criteria, but the effect is remarkable. Somewhat surprisingly, it did not appear that treatment with GV1001 could regulate the serum levels of eotaxin or MIP1α, as is clear from the following data:

Serum Analysis:

Table 1 shows Kruskal-Wallis comparison of Arms 2 and 3 baseline, Arm 2 week 7 (GemCap) with Arm 3 week 10 (GemCap and GV1001) serum.

The comparison of Arm 2 week 7 (GemCap) with Arm 3 week 10 (GemCap and GV1001) serum samples are shown in Table 2.

Mann Whitney analysis shows that there are significant increases in the levels of IL-17, IL-4, IL-5, IL-7, PDGF, RANTES and VEGF in serum samples from arm 3 week 10 patients that have received GemCap and GV1001 compared to serum samples from arm 2 week 7 patients that have received only GemCap. However, following Bonferroni-Holm correction only PDGF remains significant. Comparison graphs for IL-4, IL-5, IL7, IL-17, PDGF and VEGF cytokines in arms 2 and 3 at baseline and post treatment are shown in FIG. 1.

Paired analysis was carried out for:

Arm 2 patients at baseline and following 7 weeks of GemCap treatment.

Arm 3 patients at baseline and following 10 weeks of GemCap and GV1001 treatment. The overall P value results of these tests are shown in Table 3.

There was a clear difference in the p values from patients in arm 2 and arm 3. The paired Wilcoxon analysis indicated that there were significant differences in 19 cytokine levels between arm 2 baseline and post 7 weeks of GemCap treatment this decreases to 10 cytokines following Bonferroni Holm correction. However, in arm 3 only GM-CSF approached significance ($p=0.052$) between baseline and post 10 weeks of GV1001/GemCap treatment, this was no longer relevant following Bonferroni Holm correction.

Graphs showing the paired analysis for both arm 2 and arm 3 patients for a selection of cytokines are shown in FIG. 2. The figure also includes the number of positive and negative changes seen in the patient samples from baseline to post treatment. In the majority of arm 2 patients the cytokines analysed decrease from baseline to week 7, i.e. during GemCap treatment. This is in contrast with the arm 3 results, where the numbers of positive and negative changes are relatively evenly distributed.

C—Reactive Protein Results:

The levels of serum CRP was analysed. FIG. 3 shows the levels of CRP in serum from patients in arms 2 and 3 at baseline and following treatment. The data shows that there is no significant difference in CRP levels at baseline, however the post treatment analysis shows that there is a significant difference, with the levels in patients receiving GV1001/GemCap being significantly lower than in patients

| serum | Arm 2 baseline | Arm 2 (GemCap) week 7 | Arm 3 baseline | Arm 3 post (GemCap + GV100) Week 10 |
|---|---|---|---|---|
| Eotaxin | 172.75 pg/ml | 132.24 pg/ml | 84.22 pg/ml | 85.28 pg/ml |
| MIP1α | 15.91 | 13.38 | 11.31 | 11.48 |

| plasma | Arm 1 (GemCap) week 14 | Arm 1 (GemCap) week 26 | Arm 3 (GemCap + GV1001) Week 14 | Arm 3 post (GemCap + GV1001) Week 26 |
|---|---|---|---|---|
| Eotaxin | 77.92 pg/ml | 81.89 | 79.06 pg/ml | 87.81 |
| MIP1α | 15.92 | 14.45 | 16.23 | 17.62 | receiving GemCap only. Table 4 shows the summary statistics for the CRP data split by arm and baseline post treatment.

As with the cytokine data, paired analysis was carried out and is shown in FIG. 4. There were no significant differences in either arm 2 or 3 from baseline to post treatment.

Analysis of Plasma

Cytokine Results:

The comparison of arm 1 week 14 (GemCap) with arm 3 week 14 (GemCap and GV1001) plasma samples are shown in Table 4, there are no significant differences. The comparison of arm 1 week 26 (GemCap) with arm 3 week 26 (GemCap and GV1001) plasma samples are shown in table 5, there are no significant differences.

As with the serum analysis, plasma has been analysed with a paired Wilcoxon test, this has been carried out for the following comparisons with p values shown in Table 6:

Arm 1 patients at baseline and following 14 weeks of GemCap treatment.

Arm 3 patients at baseline and following 14 weeks of GemCap and GV1001 treatment.

Arm 1 patients at baseline and following 26 weeks of GemCap treatment.

Arm 3 patients at baseline and following 26 weeks of GemCap and GV1001 treatment.

It was noted that the decrease seen in cytokines in the serum following GemCap treatment was not seen in plasma. There was only one significant difference seen in RANTES for arm 3 week 14 patients, where levels decreased following GemCap and GV1001 treatment, however this was no longer significant following Bonferroni Holm correction.

Survival Analysis

Serum Cytokines:

Initial survival analyses of baseline, post treatment and absolute changes in cytokine levels revealed survival effects in one or both treatment arms with IL-8 (FIG. 5), Eotaxin (FIG. 6), MIP1α (FIG. 7), MIP1β (FIG. 8) and VEGF (FIG. 9).

CRP:

Although initial survival analysis has indicated an influence of baseline CRP on survival this did not reach significance. However, for arm 3 post treatment levels of CRP did appear to be significantly associated with a survival difference (median survival with high CRP 222 days, median survival with low CRP 486 days p=0.002, FIG. 11) this was not seen with arm 2 (FIG. 10).

TABLE 1

The Kruskal-Wallis comparison of Arms 2 and 3 baseline, Arm 2 week 7 (Gem-Cap) with Arm 3 week 10 (Gem-Cap and GV1001) serum

| Analyte | Kruskal-Wallis p-Value | Bonferroni-Holm Corrected | Arm 2 Baseline (pg/ml) | Arm 2 Week 7 (pg/ml) | Arm 3 Baseline (pg/ml) | Arm 3 Week 10 (pg/ml) | Arm 2 Baseline St Dev |
|---|---|---|---|---|---|---|---|
| PDGF | <0.0001 | <0.0001 | 3924.92 | 2228.25 | 4272.13 | 4046.41 | 1791.72 |
| IL-1ra | <0.0001 | 0.002 | 943.93 | 625.12 | 166.09 | 137.21 | 4145.76 |
| IL-4 | 0.0002 | 0.004 | 11.1 | 8.38 | 10.27 | 9.49 | 3.54 |
| IL-7 | 0.0002 | 0.004 | 26.97 | 20.57 | 22.7 | 21.44 | 18.22 |
| IL-17 | 0.0004 | 0.009 | 508.09 | 346.54 | 415.68 | 398.77 | 273.91 |
| IFN-g | 0.001 | 0.020 | 238.69 | 171.2 | 144.94 | 129.83 | 422.71 |
| IL-5 | 0.001 | 0.024 | 21.39 | 16.59 | 20.58 | 19.51 | 5.41 |
| IL-10 | 0.002 | 0.043 | 54.62 | 55.56 | 26.03 | 22.58 | 69.73 |
| VEGF | 0.004 | 0.063 | 117.1 | 77.44 | 102.78 | 99.79 | 79.67 |
| RANTES | 0.005 | 0.078 | 56156.98 | 31469.66 | 36870.07 | 107767.49 | 151062.34 |
| TNF-a | 0.012 | 0.192 | 144.33 | 104.02 | 101.93 | 105.26 | 172.05 |
| IL-12 | 0.013 | 0.195 | 196 | 145.55 | 70.73 | 78.37 | 310 |
| MIP-1b | 0.016 | 0.224 | 150.03 | 122.84 | 135.39 | 128.02 | 50.93 |
| IL-6 | 0.017 | 0.221 | 54.19 | 49.17 | 18.6 | 18.04 | 185.1 |
| IL-9 | 0.030 | 0.360 | 24.21 | 19.91 | 17.97 | 14.94 | 17.16 |
| IL-2 | 0.033 | 0.363 | 56.83 | 47.7 | 21.73 | 19.97 | 153.77 |
| G-CSF | 0.035 | 0.350 | 138.77 | 102.77 | 106.37 | 99.96 | 87.87 |
| IL-8 | 0.040 | 0.360 | 119.06 | 108.03 | 104.82 | 96.83 | 43.98 |
| IL-13 | 0.083 | 0.664 | 14.21 | 11.02 | 13.51 | 11.89 | 8.43 |
| MIP-1a | 0.095 | 0.665 | 15.91 | 13.38 | 11.31 | 11.48 | 12.39 |
| IL-1b | 0.135 | 0.810 | 11.16 | 8.53 | 4.71 | 4.67 | 36.67 |
| Eotaxin | 0.159 | 0.795 | 172.65 | 132.24 | 84.22 | 85.28 | 339.03 |
| GM-CSF | 0.200 | 0.800 | 61.03 | 69.49 | 48.4 | 11.54 | 155.05 |
| FGF | 0.227 | 0.681 | 131.11 | 110.15 | 94.46 | 94.02 | 95.71 |
| IP-10 | 0.441 | 0.882 | 606.81 | 678.51 | 585.7 | 622.25 | 480.13 |
| MCP-1 | 0.484 | 0.484 | 104.25 | 108.42 | 92.07 | 94.58 | 47.38 |

| Analyte | Arm 2 Week 7 St Dev | Arm 3 Baseline St Dev | Arm 3 Week 10 St Dev | Arm 2 Baseline N= | Arm 2 Week 7 N= | Arm 3 Baseline N= | Arm 3 Week 10 N= |
|---|---|---|---|---|---|---|---|
| PDGF | 1720.22 | 1793.54 | 1688.58 | 38 | 50 | 40 | 51 |
| IL-1ra | 2930.23 | 200.98 | 181.77 | 38 | 47 | 39 | 51 |
| IL-4 | 3.36 | 2.89 | 2.71 | 38 | 50 | 40 | 51 |
| IL-7 | 30.61 | 12.17 | 11.6 | 38 | 50 | 41 | 51 |
| IL-17 | 279.11 | 162.26 | 169.65 | 38 | 49 | 40 | 51 |
| IFN-g | 350.35 | 52.4 | 54.29 | 38 | 50 | 40 | 51 |
| IL-5 | 5.85 | 6.54 | 6.43 | 38 | 50 | 40 | 51 |
| IL-10 | 116.86 | 27.16 | 21.85 | 38 | 48 | 40 | 51 |
| VEGF | 96.28 | 57.02 | 71.22 | 37 | 44 | 38 | 49 |
| RANTES | 44100.47 | 26046.57 | 521514.89 | 38 | 49 | 39 | 51 |
| TNF-a | 136.23 | 36.56 | 91.02 | 38 | 50 | 40 | 51 |
| IL-12 | 265.81 | 70.43 | 119.01 | 38 | 47 | 39 | 50 |

TABLE 1-continued

The Kruskal-Wallis comparison of Arms 2 and 3 baseline, Arm 2
week 7 (Gem-Cap) with Arm 3 week 10 (Gem-Cap and GV1001) serum

| MIP-1b | 60.49 | 64.43 | 50.91 | 38 | 50 | 41 | 51 |
|---|---|---|---|---|---|---|---|
| IL-6 | 137.33 | 7.97 | 9.32 | 38 | 50 | 39 | 51 |
| IL-9 | 17.09 | 10.44 | 8.91 | 38 | 49 | 40 | 50 |
| IL-2 | 123.67 | 12.14 | 13.09 | 36 | 33 | 36 | 40 |
| G-CSF | 61.97 | 37.99 | 43.2 | 38 | 50 | 40 | 51 |
| IL-8 | 41.06 | 47.69 | 35.73 | 38 | 50 | 41 | 51 |
| IL-13 | 7.85 | 9.95 | 7.7 | 38 | 50 | 41 | 51 |
| MIP-1a | 11.62 | 5.74 | 7.37 | 38 | 50 | 41 | 50 |
| IL-1b | 30.84 | 2.36 | 2.08 | 38 | 49 | 41 | 51 |
| Eotaxin | 285.05 | 49.63 | 64.19 | 38 | 44 | 39 | 47 |
| GM-CSF | 129.57 | 132.38 | 14.87 | 12 | 10 | 10 | 8 |
| FGF | 95.88 | 51.32 | 60.78 | 38 | 39 | 38 | 41 |
| IP-10 | 1108.63 | 359.53 | 356.08 | 38 | 50 | 41 | 51 |
| MCP-1 | 68.02 | 37.14 | 44.01 | 38 | 50 | 41 | 51 |

TABLE 2

The comparison of Arm 2 week 7 (Gem-Cap) with Arm 3 week 10 (Gem-Cap and GV1001) serum

| Analyte | Mann-Whitney P-Value | Bonferroni Holm Correct P Value | Arm 2 Week 7 Mean (pg/ml) | Arm 3 Week 10 Mean (pg/ml) | Arm 2 Week 7 Std Dev | Arm 3 Week 10 Std Dev | Arm 2 Week 7 N= | Arm 3 Week 10 N= |
|---|---|---|---|---|---|---|---|---|
| Eotaxin | 0.987 | 0.987 | 132.24 | 85.28 | 285.05 | 64.19 | 44 | 47 |
| FGF basic | 0.859 | 1.718 | 110.15 | 94.02 | 95.88 | 60.78 | 39 | 41 |
| G-CSF | 0.694 | 3.470 | 102.77 | 99.96 | 61.97 | 43.2 | 50 | 51 |
| GM-CSF | 0.091 | 1.729 | 69.49 | 11.54 | 129.57 | 14.87 | 10 | 8 |
| IFN-g | 0.828 | 2.484 | 171.2 | 129.83 | 350.35 | 54.29 | 50 | 51 |
| IL-10 | 0.454 | 3.632 | 55.56 | 22.58 | 116.86 | 21.85 | 48 | 51 |
| IL-12(p70) | 0.468 | 3.276 | 145.55 | 78.37 | 265.81 | 119.01 | 47 | 50 |
| IL-13 | 0.596 | 3.576 | 11.02 | 11.89 | 7.85 | 7.7 | 50 | 51 |
| IL-17 | 0.00694 | 0.167 | 346.54 | 398.77 | 279.11 | 169.65 | 49 | 51 |
| IL-1b | 0.296 | 3.848 | 8.53 | 4.67 | 30.84 | 2.08 | 49 | 51 |
| IL-1ra | 0.39 | 3.510 | 625.12 | 137.21 | 2930.23 | 181.77 | 47 | 51 |
| IL-2 | 0.273 | 3.822 | 47.7 | 19.97 | 123.67 | 13.09 | 33 | 40 |
| IL-4 | 0.036 | 0.756 | 8.38 | 9.49 | 3.36 | 2.71 | 50 | 51 |
| IL-5 | 0.049 | 0.980 | 16.59 | 19.51 | 5.85 | 6.43 | 50 | 51 |
| IL-6 | 0.12 | 2.160 | 49.17 | 18.04 | 137.33 | 9.32 | 50 | 51 |
| IL-7 | 0.033 | 0.726 | 20.57 | 21.44 | 30.61 | 11.6 | 50 | 51 |
| IL-8 | 0.133 | 2.128 | 108.03 | 96.83 | 41.06 | 35.73 | 50 | 51 |
| IL-9 | 0.347 | 3.470 | 19.91 | 14.94 | 17.09 | 8.91 | 49 | 50 |
| IP-10 | 0.121 | 2.057 | 678.51 | 622.25 | 1108.63 | 356.08 | 50 | 51 |
| MCP-1 | 0.174 | 2.610 | 108.42 | 94.58 | 68.02 | 44.01 | 50 | 51 |
| MIP-1a | 0.791 | 3.164 | 13.38 | 11.48 | 11.62 | 7.37 | 50 | 50 |
| MIP-1b | 0.299 | 3.588 | 122.84 | 128.02 | 60.49 | 50.91 | 50 | 51 |
| PDGF | 5.31E−08 | <0.001 | 2228.25 | 4046.41 | 1720.22 | 1688.58 | 50 | 51 |
| RANTES | 0.00203 | 0.051 | 31469.66 | 107767.49 | 44100.47 | 521514.89 | 49 | 51 |
| TNF-a | 0.31 | 3.410 | 104.02 | 105.26 | 136.23 | 91.02 | 50 | 51 |
| VEGF | 0.021 | 0.483 | 77.44 | 99.79 | 96.28 | 71.22 | 44 | 49 |

TABLE 3

Shown are the p values for the paired comparison of arm 2 baseline versus week 7 and arm 3 baseline versus week 10

| Cytokine | Wilcoxon Paired Test Arm 2 | Wilcoxon Paired Test Arm 3 | Bonferroni Holm Corrected Arm 2 | Bonferroni Holm Corrected Arm 3 |
|---|---|---|---|---|
| Eotaxin | 0.0042 | 0.8307 | 0.059 | 2.492 |
| FGF-Basic | 0.0129 | 0.2477 | 0.142 | 4.211 |
| G-CSF | 0.0025 | 0.2357 | 0.045 | 4.714 |
| GM-CSF | 0.8394 | 0.0522 | 1.679 | 1.357 |
| IFN-g | 0.0008 | 0.2468 | 0.018 | 4.442 |
| IL-10 | 0.014 | 0.2207 | 0.140 | 4.635 |
| IL-12 | 0.0199 | 0.4106 | 0.179 | 4.106 |
| IL-13 | 0.0454 | 0.396 | 0.363 | 4.356 |
| IL-17 | 0.0003 | 0.2909 | 0.008 | 4.654 |
| IL-1b | 0.0027 | 0.5392 | 0.041 | 3.235 |
| IL-1ra | 0.0089 | 0.0959 | 0.107 | 2.302 |
| IL-2 | 0.0009 | 0.2372 | 0.019 | 4.507 |
| IL-4 | 0.0005 | 0.3747 | 0.012 | 4.496 |
| IL-5 | 0.0004 | 0.5129 | 0.010 | 3.590 |
| IL-6 | 0.4043 | 0.9535 | 1.213 | 1.907 |
| IL-7 | 0.0025 | 0.4641 | 0.043 | 3.713 |
| IL-8 | 0.0624 | 0.3029 | 0.437 | 4.544 |
| IL-9 | 0.1617 | 0.0985 | 0.809 | 2.266 |
| IP-10 | 0.1705 | 0.3279 | 0.682 | 4.591 |
| MCP-1 | 0.9364 | 0.6927 | 0.936 | 3.464 |
| MIP-1a | 0.141 | 0.2183 | 0.846 | 4.803 |
| MIP-1b | 0.0018 | 0.4255 | 0.036 | 3.830 |
| PDGF | 0.0001 | 0.0696 | 0.003 | 1.740 |
| RANTES | 0.00464 | 0.7698 | 0.060 | 3.079 |
| TNFa | 0.0025 | 0.3609 | 0.040 | 4.692 |
| VEFG | 0.0023 | 0.9777 | 0.044 | 0.978 |

TABLE 4

Summary statistics for CRP data

|  | Arm 2 Baseline | Arm 2 Week 7 | Arm 3 Baseline | Arm 3 Week 10 |
|---|---|---|---|---|
| n= | 38 | 50 | 41 | 51 |
| Range | 5-238 | 5-175 | 5-77 | 5-97 |
| Mean (mg/l) | 20.70 | 21.60 | 15.96 | 13.60 |
| Median (mg/l) | 7.00 | 12.00 | 6.00 | 6.00 |
| St Dev | 40.40 | 26.60 | 18.00 | 18.27 |

TABLE 5A

The comparison of arm 1 week 14 (Gem-Cap) with arm 3 week 14 (Gem-Cap and GV1001) plasma

| Analyte | Mann-Whitney P-Value | Arm 1 Week 14 Mean (pg/ml) | Arm 3 Week 14 Mean (pg/ml) | Arm 1 Week 14 Std Dev | Arm 3 Week 14 Std Dev | Arm 1 Week 14 N= | Arm 3 Week 14 N= |
|---|---|---|---|---|---|---|---|
| Eotaxin | 0.644 | 77.32 | 79.06 | 52.83 | 76.8 | 19 | 35 |
| FGF basic | 0.926 | 139.37 | 133.58 | 93.37 | 80.31 | 18 | 31 |
| G-CSF | 0.848 | 146.67 | 149.68 | 105.15 | 99.17 | 22 | 36 |
| GM-CSF | 0.904 | 25.2 | 28.13 | 22.74 | 25.59 | 14 | 24 |
| IFN-g | 0.817 | 222.03 | 212.81 | 184.02 | 166.71 | 21 | 36 |
| IL-10 | 0.83 | 38.3 | 37.83 | 38.91 | 38.52 | 20 | 34 |
| IL-12 | 0.566 | 71.28 | 72.41 | 66.42 | 55.71 | 19 | 30 |
| IL-13 | 0.576 | 19.04 | 24.08 | 17.04 | 36.98 | 23 | 36 |
| IL-17 | 0.287 | 310.21 | 242.25 | 236.38 | 204.02 | 18 | 36 |
| IL-1b | 0.832 | 7.55 | 7.36 | 6.21 | 5.37 | 21 | 35 |
| IL-1ra | 0.872 | 261.48 | 278.84 | 263.25 | 273.17 | 21 | 35 |
| IL-2 | 0.468 | 31 | 35 | 27.32 | 24.55 | 16 | 26 |
| IL-4 | 0.947 | 8.67 | 8.55 | 6.02 | 6.07 | 21 | 36 |
| IL-5 | 0.768 | 22.74 | 23.96 | 18.29 | 17.48 | 23 | 36 |
| IL-6 | 0.597 | 28.85 | 31.66 | 25.84 | 24.14 | 21 | 36 |
| IL-7 | 0.938 | 26.02 | 25.36 | 18.7 | 17.65 | 23 | 36 |
| IL-8 | 0.544 | 89.83 | 100.79 | 62.96 | 65.8 | 23 | 36 |
| IL-9 | 0.436 | 31.43 | 22.68 | 32.3 | 19.28 | 19 | 34 |
| IP-10 | 0.128 | 426.93 | 552.65 | 243.56 | 399.59 | 23 | 36 |
| MCP-1 | 0.828 | 74.55 | 75.09 | 52.21 | 42.68 | 23 | 36 |
| MIP-1a | 0.689 | 15.92 | 16.23 | 10.79 | 8.56 | 22 | 36 |
| MIP-1b | 0.132 | 69.25 | 80.07 | 32.35 | 29.81 | 23 | 36 |
| PDGF | 0.694 | 843.99 | 841.71 | 763.73 | 790.98 | 20 | 36 |
| RANTES | 0.779 | 16082.77 | 16775.4 | 13640.29 | 13237.25 | 21 | 36 |
| TNF-a | 0.921 | 153.59 | 153.63 | 131.33 | 120.9 | 21 | 36 |
| VEGF | 0.792 | 50.63 | 48.63 | 53.93 | 44.09 | 14 | 25 |

TABLE 5B

The comparison of arm 1 week 26 (Gem-Cap) with arm 3 week 26 (Gem-Cap and GV1001) plasma

| Analyte | Mann-Whitney P-Value | Arm 1 Week 26 Mean (pg/ml) | Arm 3 Week 26 Mean (pg/ml) | Arm 1 Week 26 Std Dev | Arm 3 Week 26 Std Dev | Arm 1 Week 26 N= | Arm 3 Week 26 N= |
|---|---|---|---|---|---|---|---|
| Eotaxin | 0.826 | 81.89 | 87.81 | 66.34 | 63.55 | 14 | 27 |
| FGF basic | 0.541 | 151.21 | 135.93 | 93.38 | 90.95 | 13 | 26 |
| G-CSF | 0.688 | 162.99 | 168.96 | 129.63 | 106.37 | 16 | 27 |
| GM-CSF | 0.237 | 66.4 | 29.1 | 89.19 | 30.16 | 9 | 18 |
| IFN-g | 0.709 | 230.92 | 252.86 | 203.79 | 202.9 | 17 | 27 |
| IL-10 | 0.856 | 46.67 | 46.67 | 38.23 | 43.06 | 16 | 26 |
| IL-12 | 0.969 | 73.72 | 79.1 | 81.14 | 84.54 | 15 | 27 |
| IL-13 | 0.933 | 23.96 | 23.15 | 23.11 | 21.23 | 17 | 27 |
|  | 0.03 | 37.57 | 18.24 | 5.09 | 10.76 | 3 | 7 |
| IL-17 | 0.805 | 299.09 | 274.4 | 219.64 | 206.66 | 14 | 27 |
| IL-1b | 0.368 | 7.75 | 10.12 | 6.35 | 8.44 | 17 | 24 |
| IL-1ra | 0.546 | 448.9 | 317.37 | 445.43 | 306.59 | 16 | 27 |
| IL-2 | 0.59 | 36.09 | 39.65 | 29.95 | 28.5 | 14 | 21 |
| IL-4 | 0.691 | 9.13 | 9.61 | 7.91 | 6.6 | 17 | 27 |
| IL-5 | 0.555 | 25.23 | 28.35 | 20.13 | 20.34 | 17 | 27 |
| IL-6 | 0.92 | 31.92 | 32.82 | 24.99 | 25.61 | 16 | 27 |
| IL-7 | 0.763 | 28.02 | 30.06 | 18.16 | 18.47 | 17 | 27 |
| IL-8 | 0.638 | 102.04 | 109.65 | 78.4 | 70.9 | 17 | 27 |
| IL-9 | 0.978 | 28.03 | 26.7 | 23.7 | 19.85 | 15 | 25 |
| IP-10 | 0.876 | 431.27 | 495.29 | 234.75 | 332.43 | 17 | 27 |
| MCP-1 | 0.507 | 83.53 | 90.7 | 62.11 | 61.04 | 17 | 27 |
| MIP-1a | 0.242 | 14.45 | 17.62 | 9.88 | 9.28 | 17 | 27 |
| MIP-1b | 0.099 | 65.96 | 80.56 | 33.71 | 27.82 | 17 | 27 |
| PDGF | 0.844 | 1098.88 | 1044.5 | 940.97 | 961.42 | 15 | 27 |

TABLE 5B-continued

The comparison of arm 1 week 26 (Gem-Cap) with arm 3 week 26 (Gem-Cap and GV1001) plasma

| Analyte | Mann-Whitney P-Value | Arm 1 Week 26 Mean (pg/ml) | Arm 3 Week 26 Mean (pg/ml) | Arm 1 Week 26 Std Dev | Arm 3 Week 26 Std Dev | Arm 1 Week 26 N= | Arn 3 Week 26 N= |
|---|---|---|---|---|---|---|---|
| RANTES | 0.209 | 13632.77 | 20133.86 | 12204.71 | 16974.26 | 16 | 27 |
| TNF-a | 0.706 | 167.63 | 176.14 | 143.56 | 132.79 | 16 | 27 |
| VEGF | 0.962 | 64.83 | 61.7 | 47.07 | 41.9 | 10 | 18 |

TABLE 6

P values for the paired comparison of arm 1 baseline versus arm 1 week 14 and arm 3 baseline versus arm 3 week 14 (left) and arm 1 baseline versus arm 1 week 26 and arm 3 baseline versus arm 3 week 26 (right).

| | Week 14 Paired Wilcoxon P value | | | Week 26 Paired Wilcoxon P value | |
|---|---|---|---|---|---|
| Cytokine | Arm 1 | Arm 3 | Cytokine | Arm 1 | Arm 3 |
| Eotaxin | 0.5771 | 0.0827 | Eotaxin | 0.625 | 0.498 |
| FGF-Basic | 0.4648 | 0.2904 | FGF-Basic | 0.6953 | 0.7285 |
| G-CSF | 0.3396 | 0.2758 | G-CSF | 0.6772 | 0.6477 |
| GM-CSF | 0.5703 | 0.6226 | GM-CSF | 0.8438 | 0.8603 |
| IFN-g | 0.4143 | 0.3819 | IFN-g | 0.3804 | 0.7562 |
| IL-10 | 0.3804 | 0.4237 | IL-10 | 0.4131 | 0.8596 |
| IL-12 | 0.4697 | 0.2238 | IL-12 | 0.8984 | 1 |
| IL-13 | 0.6355 | 0.8191 | IL-13 | 0.5186 | 0.9563 |
| IL-15 | 0.4375 | 0.25 | IL-15 | NA | 0.8203 |
| IL-17 | 0.2783 | 0.1578 | IL-17 | 0.8457 | 0.6215 |
| IL-1b | 0.4548 | 0.2087 | IL-1b | 0.5186 | 0.89 |
| IL-1ra | 0.3804 | 0.1742 | IL-1ra | 0.4131 | 0.4091 |
| IL-2 | 0.2783 | 0.1283 | IL-2 | 0.9219 | 0.5798 |
| IL-4 | 0.3396 | 0.313 | IL-4 | 0.791 | 0.6742 |
| IL-5 | 0.3396 | 0.3819 | IL-5 | 0.791 | 0.7012 |
| IL-6 | 0.5693 | 0.4593 | IL-6 | 0.6377 | 0.4749 |
| IL-7 | 0.5417 | 0.313 | IL-7 | 1 | 0.8408 |
| IL-8 | 0.5417 | 0.3674 | IL-8 | 0.6772 | 0.7841 |
| IL-9 | 0.3394 | 0.3967 | IL-9 | 0.8311 | 0.6742 |
| IP-10 | 0.0942 | 0.4273 | IP-10 | 0.2334 | 0.4749 |
| MCP-1 | 0.7354 | 0.5812 | MCP-1 | 0.1294 | 0.9854 |
| MIP-1a | 0.4143 | 0.2758 | MIP-1a | 0.791 | 0.7285 |
| MIP-1b | 0.0681 | 0.7164 | MIP-1b | 0.1763 | 0.33 |
| PDGF | 0.1099 | 0.5272 | PDGF | 0.1099 | 0.5217 |
| RANTES | 0.8311 | 0.0299 | RANTES | 0.8984 | 0.7983 |
| TNFa | 0.4143 | 0.2528 | TNFa | 0.6772 | 0.6477 |
| VEFG | 0.4316 | 0.2305 | VEFG | 0.7344 | 0.9632 |

Further Results of Analyses

FIG. 13 shows profile plots of baseline and post-treatment means of log serum cytokine data for Arm 2.

FIG. 14 shows baseline and post-treatment means of log serum cytokine data for Arm 3.

FIG. 15 shows a profile plot of the mean differences (post-treatment–baseline) for the cytokines in serum for each arm.

Of note, The analyses revealed that 19 cytokines showed a statistically significant decrease in serum between baseline and post-treatment in Arm 2 (PDGF, IL1β, IL-1rα, IL-2, IL-4, IL-5, IL-7, IL-10, IL-12, IL-13, IL-17, G-CSF, IFNγ, eotaxin, FGFb, MIP1β, RANTES, TNFα, VEGF; but not CRP, IL-6, IL-8, IL-9, IL-15, GM-CSF, IP10, MCP1, MIP1α), whereas none showed a statistically significant decrease in Arm3. This appears from FIG. 16, which provides the p-values obtained from a Wilcoxon signed-rank test used on each cytokine for each arm to test for increase/decrease in values from baseline to post-treatment. The significant differences as seen are in bold grey font. The decreases were larger in Arm2 than in Arm3, noting that there were 19 significant decreases in Arm2 but none in Arm3.

FIG. 17 shows the median difference of post-treatment minus baseline levels in serum for each cytokine and for each arm of the study. Decreases are highlighted in light shadow and increases/no change are highlighted in dark shadow.

FIG. 18 shows Cox proportional hazards models on baseline data for each cytokine in serum for each arm of the study. The table provides univariate analyses for the baseline data and shows hazard ratios with 95% confidence intervals and p-values. CRP, IL-1ra, IL-2, IL-10, Eotaxin and IFNγ are significant (p<0.1) for Arm 2, while CRP, IL-1ra and Eotaxin are significant for Arm 3.

FIGS. 19a and 19b show serum levels of CRP at baseline in Arm 2 and Arm 3. Low levels of CRP gave a median survival of 337 days for Arm 2 and a median survival of 373 days for Arm 3. Baseline CRP levels predicted median (95% CI) overall survival in Arm3 (high CRP=250 [132-451] days; low CRP=372.5 [229-517] days; p=0.0500) but not in Arm2 (high CRP=195 [140-262] days; low CRP=337 [167-366] days; p=0.2534)

FIGS. 20a and 20b show levels of Eotaxin at baseline in Arm 2 and Arm 3. High levels of Eotaxin give a median survival of 300 days for Arm 2 and a median survival of 451 days for Arm 3. Baseline eotaxin levels predicted median (95% CI) overall survival in Arm3 (high eotaxin=451 [308-623]days; low eotaxin=238.5 [178-344] days; p=0.0135) but not in Arm2 (high eotaxin=299.5 [167-358] days; low eotaxin=188 [102-320] days; p=0.1138)

FIG. 21a and FIG. 21b shows Proportional hazards models using dichotomized variables for the baseline data for serum CRP and serum Eotaxin combined. When variables were combined at baseline the longest overall survival was predicted by a combination of low serum levels of CRP plus high serum levels of Eotaxin in Arm 2 (median survival=337 days) and similarly for Arm 3 (median survival=450 days).

FIGS. 22a and 22b show serum CRP post treatment in Arm 2 and Arm 3. Low serum levels of CRP give a median survival of 337 days for Arm 2 and a median survival of 450 days for Arm 3.

FIGS. 23a and 23b show serum Eotaxin post treatment in Arm 2 and Arm 3. High levels of serum Eotaxin give a median survival of 251 days for Arm 2 and a median survival of 364 days for Arm 3.

FIGS. 24a and 24b show Proportional hazards models using dichotomized variables for the post-treatment data for serum CRP and serum Eotaxin combined. When variables were combined the longest survival was predicted by a combination of low levels of CRP plus high levels of Eotaxin in Arm 2 (median survival=355 days) and similarly for Arm 3 (median survival=535 days). When variables were combined at post-treatment the longest survival was predicted by a combination of low levels of CRP plus high levels of Eotaxin in Arm 2 (median survival=355 days) and similarly for Arm 3 (median survival=535 days).

Sequence Listing Free Text
Biologic Sequence Data

SEQ ID NO: 1; GV1001 amino acid sequence:
EARPALLTSRLRFIPK

SEQ ID NO: 2; Human Eotaxin (Eotaxin1) (CCL11 chemokine (C-C motif) ligand 11); Protein; UniProt ID: P51671; Length: 97 amino acids, MW: 10.732
kDa: MKVSAALLWLLLIAAAFSPQGLAGPASVPTTCCFNLANRKIPLQR LESYRRITSGKCPQKAVIFKTKLAKDICADPKKKWVQDSMKYLDQKSPTP KP SEQ ID NO: 3; Human eotaxin 2 (CCL24); Protein; UniProt ID: O00175; Length: 119 amino acids, MW: 13.134
kDa: MAGLMTIVTSLLFLGVCAHHIIPTGSVVIPSPCCMFFVSKRIPEN RVVSYQLSSRSTCLKAGVIFTTKKGQQFCGDPKQEWVQRYMKNLDAKQKK ASPRARAVAVKGPVQRYPGNQTTC SEQ ID NO: 4; Human eotaxin 3 (CCL26); Protein; UniProt ID: Q9Y258; Length: 94 amino acids, MW: 10.648
kDa: MMGLSLASAVLLASLLSLHLGTATRGSDISKTCCFQYSHKPLPWT WVRSYEFTSNSCSQRAVIFTTKRGKKVCTHPRKKWVQKYISLLKTPKQL SEQ ID NO: 5; Human Eotaxin(Eotaxin1) (CCL11 chemokine (C-C motif) ligand 11); nucleic acid; NCBI GeneBank ID:
NM_002986.2: ATGGGCAAAGGCTTCCCTGGAATCTCCCACACTGTCT
GCTCCCTATAAAAGGCAGGCAGATGGGCCAGAGGAGCAGAGAGGCTGAGA
CCAACCCAGAAACCACCACCTCTCACGCCAAAGCTCACACCTTCAGCCTC
CAACATGAAGGTCTCCGCAGCACTTCTGTGGCTGCTGCTCATAGCAGCTG
CCTTCAGCCCCCAGGGGCTCGCTGGGCCAGCTTCTGTCCCAACCACCTGC
TGCTTTAACCTGGCCAATAGGAAGATACCCCTTCAGCGACTAGAGAGCTA
CAGGAGAATCACCAGTGGCAAATGTCCCCAGAAAGCTGTGATCTTCAAGA
CCAAACTGGCCAAGGATATCTGTGCCGACCCCAAGAAGAAGTGGGTGCAG
GATTCCATGAAGTATCTGGACCAAAAATCTCCAACTCCAAAGCCATAAAT
AATCACCATTTTTGAAACCAAACCAGAGCCTGAGTGTTGCCTAATTTGTT
TTCCCTTCTTACAATGCATTCTGAGGTAACCTCATTATCAGTCCAAAGGG
CATGGGTTTTATTATATATATATTTTTTTTTTAAAAAAAAAACGTAT
TGCATTTAATTTATTGAGGCTTTAAAACTTATCCTCCATGAATATCAGTT
ATTTTTAAACTGTAAAGCTTTGTGCAGATTCTTTACCCCCTGGGAGCCCC
AATTCGATCCCCTGTCACGTGTGGGCAATGTTCCCCCTCTCCTCTCTTCC
TCCCTGGAATCTTGTAAAGGTCCTGGCAAAGATGATCAGTATGAAAATGT
CATTGTTCTTGTGAACCCAAAGTGTGACTCATTAAATGGAAGTAAATGTT
GTTTTAGGAATACATAAAGTATGTGCATATTTTATTATAGTCACTAGTTG
TAATTTTTTTGTGGGAAATCCACACTGAGCTGAGGGGG SEQ ID NO: 6; Human eotaxin 2 (CCL24); nucleic acid; NCBI GeneBank ID:
NM_002991.2: ATGGCAGGCCTGATGACCATAGTAACCAGCCTTCTGT
TCCTTGGTGTCTGTGCCCACCACATCATCCCTACGGGCTCTGTGGTCATC
CCCTCTCCCTGCTGCATGTTCTTTGTTTCCAAGAGAATTCCTGAGAACCG
AGTGGTCAGCTACCAGCTGTCCAGCAGGAGCACATGCCTCAAGGCAGGAG
TGATCTTCACCACCAAGAAGGGCCAGCAGTTCTGTGGCGACCCCAAGCAG
GAGTGGGTCCAGAGGTACATGAAGAACCTGGACGCCAAGCAGAAGAAGGC
TTCCCCTAGGGCCAGGGCAGTGGCTGTCAAGGGCCCTGTCCAGAGATATC
CTGGCAACCAAACCACCTGCTAA SEQ ID NO: 7; Human Eotaxin 3 (CCL26); nucleic acid; NCBI GeneBank ID:
NM_006072.4: CTGGAATTGAGGCTGAGCCAAAGACCCCAGGGCCGTC
TCAGTCTCATAAAAGGGGATCAGGCAGGAGGAGTTTGGGAGAAACCTGAG
AAGGGCCTGATTTGCAGCATCATGATGGGCCTCTCCTTGGCCTCTGCTGT
GCTCCTGGCCTCCCTCCTGAGTCTCCACCTTGGAACTGCCACACGTGGGA
GTGACATATCCAAGACCTGCTGCTTCCAATACAGCCACAAGCCCCTTCCC
TGGACCTGGGTGCGAAGCTATGAATTCACCAGTAACAGCTGCTCCCAGCG
GGCTGTGATATTCACTACCAAAAGAGGCAAGAAAGTCTGTACCCATCCAA
GGAAAAAATGGGTGCAAAAATACATTTCTTTACTGAAAACTCCGAAACAA
TTGTGACTCAGCTGAATTTTCATCCGAGGACGCTTGGACCCCGCTCTTGG
CTCTGCAGCCCTCTGGGGAGCCTGCGGAATCTTTTCTGAAGGCTACATGG
ACCCGCTGGGGAGGAGAGGGTGTTTCCTCCCAGAGTTACTTTAATAAAGG
TTGTTCATAGAGTTGACTTGTTCAT SEQ ID NO: 8; Human CRP (C-reactive protein); Protein; UniProt ID: Q5VVP7; Length: 102 amino acids, MW: 11.632
kDa: MEKLLCFLVLTSLSHAFGQTDMSRKAFVFPKESDTSYVSLKAPLT KPLKAFTVCLHFYTELSSTHEINTIYLGGPFSPNVLNWRALKYEVQGEVF TKPQLWP SEQ ID NO: 9; Human CRP (C-reactive protein); nucleic acid; NCBI GeneBank ID:
AAAGAATCAGAATTTGAGGTGTTTTGTTTTCATTTTTATTTCAAGTTGGA
CAGATCTTGGAGATAATTTCTTACCTCACATAGATGAGAAAACTAACACC
CAGAAAGGAGAAATGATGTTATAAAAAACTCATAAGGCAAGAGCTGAGAA
GGAAGCGCTGATCTTCTATTTAATTCCCCACCCATGACCCCCAGAAAGCA
GGAGGGCATTGCCCACATTCACAGGGCTCTTCAGTCTCAGAATCAGGACA
CTGGCCAGGTGTCTGGTTTGGGTCCAGAGTGCTCATCATCATGTCATAGA
ACTGCTGGGCCCAGGTCTCCTGAAATGGGAAGCCCAGCAATACCACGCAG
TCCCTCCACTTTCTCAAAGCACACTGGAAAGGCCATTAGAATTGCCCCAG
CAGAGCAGATCTGCTTTTTTTCCAGAGCAAAATGAAGCACTAGGTATAAA
TATGTTGTTACTGCCAAGAACTTAAATGACTGGTTTTTGTTTGCTTGCAG
TGCTTTCTTAATTTTATGGCTCTTCTGGGAAACTCCTCCCCTTTTCCACA
CGAACCTTGTGGGGCTGTGAATTCTTTCTTCATCCCCGCATTCCCAATAT
ACCCAGGCCACAAGAGTGGACGTGAACCACAGGGTGTCCTGTCAGAGGAG
CCCATCTCCCATCTCCCCAGCTCCCTATCTGGAGGATAGTTGGATAGTTA
CGTGTTCCTAGCAGGACCAACTACAGTCTTCCCAAGGATTGAGTTATGGA
CTTTGGGAGTGAGACATCTTCTTGCTGCTGGATTTCCAAGCTGAGAGGAC
GTGAACCTGGGACCACCAGTAGCCATCTTGTTGCCACATGGAGAGAGAC -continued

TGTGAGGACAGAAGCCAAACTGGAAGTGGAGGAGCCAAGGGATTGACAAA

CAACAGAGCCTTGACCACGTGGAGTCTCTGAATCAGCCTTGTCTGGAACC

AGATCTACACCTGGACTGCCCAGGTCTATAAGCCAATAAAGCCCCTGTTT

ACTTGAAAAAAAAAA

SEQ ID NO: 10; Human MIP1α (CCL3 chemokine (C-C motif) ligand 3); Protein; UniProt ID: P10147; Length: 92 amino acids, MW: 10.085 kDa: MQVSTAALAVLLCTMALCNQFSASLAADTPTACCFSYTSRQIPQN

FIADYFETSSQCSKPGVIFLTKRSRQVCADPSEEWVQKYVSDLELSA

SEQ ID NO: 11; Human MIP1α (CCL3 chemokine (C-C motif) ligand 3); nucleic acid; NCBI GeneBank ID: NM_002983.2: AGCTGGTTTCAGACTTCAGAAGGACACGGGCAGCAGA

CAGTGGTCAGTCCTTTCTTGGCTCTGCTGACACTCGAGCCCACATTCCGT

CACCTGCTCAGAATCATGCAGGTCTCCACTGCTGCCCTTGCTGTCCTCCT

CTGCACCATGGCTCTCTGCAACCAGTTCTCTGCATCACTTGCTGCTGACA

CGCCGACCGCCTGCTGCTTCAGCTACACCTCCCGGCAGATTCCACAGAAT

TTCATAGCTGACTACTTTGAGACGAGCAGCCAGTGCTCCAAGCCCGGTGT

CATCTTCCTAACCAAGCGAAGCCGGCAGGTCTGTGCTGACCCCAGTGAGG

AGTGGGTCCAGAAATATGTCAGCGACCTGGAGCTGAGTGCCTGAGGGGTC

CAGAAGCTTCGAGGCCCAGCGACCTCGGTGGGCCCAGTGGGAGGAGCAG

GAGCCTGAGCCTTGGGAACATGCGTGTGACCTCCACAGCTACCTCTTCTA

TGGACTGGTTGTTGCCAAACAGCCACACTGTGGGACTCTTCTTAACTTAA

ATTTTAATTTATTTATACTATTTAGTTTTTGTAATTTATTTTCGATTTCA

CAGTGTGTTTGTGATTGTTTGCTCTGAGAGTTCCCCTGTCCCCTCCCCCT

TCCCTCACACCGCGTCTGGTGACAACCGAGTGGCTGTCATCAGCCTGTGT

AGGCAGTCATGGCACCAAAGCCACCAGACTGACAAATGTGTATCGGATGC

TTTTGTTCAGGGCTGTGATCGGCCTGGGGAAATAATAAAGATGCTCTTTT

AAAAGGTAAAAAAAAAAAAAAAAAAAA

---

The invention claimed is:

1. A method for treating an individual suffering from locally advanced and metastatic pancreatic cancer comprising:
   (a) determining the level of eotaxin (w/v) in a serum sample of the individual;
   (b) comparing the level of (a) to the average serum eotaxin (w/v) level for a population of individuals having locally advanced and metastatic pancreatic cancer, and if the individual's serum level is at least 10% higher than the average serum level,
   (c) administering a composition comprising a polypeptide consisting of SEQ ID NO: 1 to the individual concurrently with gemcitabine and capecitabine treatment, whereby survival time is increased.

2. The method according to claim 1, wherein the composition is administered in combination with granulocyte-macrophage colony-stimulating factor (GM-CSF).

3. The method according to claim 1, wherein granulocyte-macrophage colony-stimulating factor (GM-CSF) is administered prior to administration of the composition.

4. The method according to claim 1, wherein the composition is administered parenterally.

5. The method according to claim 1, further comprising after the administration, measuring the level of CRP (w/v) in the serum of the individual and continuing the administration if the level of CRP exhibits a decrease of more than 10% compared to the population average of individuals suffering from the same cancer.

6. The method according to claim 3, wherein
GM-CSF is administered 10 to 15 minutes before the composition is administered,
GM-CSF and the composition are administered intradermally, and
GM-CSF and the composition are administered three times during the first week of treatment, once during the second, third, fourth, and sixth weeks of treatment, and once every four weeks thereafter.

7. A method for treating an individual suffering from locally advanced and metastatic pancreatic cancer comprising:
   (a) determining the level of eotaxin (w/v) in a serum sample of the individual;
   (b) determining the level of CRP (w/v) in the serum sample of the individual;
   (c) comparing the level of (a) to the average serum eotaxin (w/v) level for a population of individuals having locally advanced and metastatic pancreatic cancer;
   (d) comparing the level of (b) to the average serum CRP (w/v) level for a population of individuals having locally advanced and metastatic pancreatic cancer; if the individual's serum eotaxin level is at least 10% higher than the average serum level and the level of CRP exhibits a decrease of at least 10% compared to the population average of individuals suffering from the same cancer,
   (e) administering a composition comprising a polypeptide consisting of SEQ ID NO: 1 to the individual concurrently with gemcitabine and capecitabine treatment, whereby survival time is increased.

* * * * *